(12) United States Patent
Weir

(10) Patent No.: US 11,259,886 B2
(45) Date of Patent: Mar. 1, 2022

(54) METHODS, SYSTEMS, AND DEVICES FOR CONTROLLING MOVEMENT OF A ROBOTIC SURGICAL SYSTEM

(71) Applicant: Ethicon LLC, Guaynabo, PR (US)

(72) Inventor: Michael P. Weir, Blanchester, OH (US)

(73) Assignee: Cilag GmbH International, Zug (CH)

( * ) Notice: Subject to any disclaimer, the term of this patent is extended or adjusted under 35 U.S.C. 154(b) by 435 days.

(21) Appl. No.: 16/185,404

(22) Filed: Nov. 9, 2018

(65) Prior Publication Data

US 2019/0076202 A1 Mar. 14, 2019

Related U.S. Application Data

(62) Division of application No. 14/988,852, filed on Jan. 6, 2016, now Pat. No. 10,154,886.

(51) Int. Cl.

| | |
|---|---|
| *G05B 19/04* | (2006.01) |
| *G05B 19/18* | (2006.01) |
| *A61B 34/37* | (2016.01) |
| *B25J 9/16* | (2006.01) |
| *A61B 34/00* | (2016.01) |
| *A61B 90/00* | (2016.01) |

(Continued)

(52) U.S. Cl.
CPC ............. *A61B 34/37* (2016.02); *A61B 34/25* (2016.02); *A61B 90/361* (2016.02); *B25J 9/1689* (2013.01); *A61B 18/1445* (2013.01); *A61B 2017/00115* (2013.01); *A61B 2017/00128* (2013.01); *A61B 2034/2055* (2016.02); *A61B 2034/2059* (2016.02); *Y10S 901/02* (2013.01); *Y10S 901/18* (2013.01); *Y10S 901/30* (2013.01); *Y10S 901/47* (2013.01)

(58) Field of Classification Search
CPC ...... A61B 18/1445; A61B 2017/00115; A61B 2017/00128; A61B 2034/2055; A61B 2034/2059; A61B 34/25; A61B 34/37; A61B 90/361; B25J 9/1689; Y10S 901/02; Y10S 901/18; Y10S 901/30; Y10S 901/47
See application file for complete search history.

(56) References Cited

U.S. PATENT DOCUMENTS

| | | |
|---|---|---|
| 5,876,325 A | 3/1999 | Mizuno et al. |
| 6,434,416 B1 | 8/2002 | Mizoguchi et al. |

(Continued)

FOREIGN PATENT DOCUMENTS

| | | |
|---|---|---|
| WO | WO-2014151621 A1 | 9/2014 |
| WO | WO-2014151952 A1 | 9/2014 |

OTHER PUBLICATIONS

U.S. Appl. No. 14/988,852, filed Jan. 6, 2016, Michael P. Weir.

(Continued)

*Primary Examiner* — Harry Y Oh
(74) *Attorney, Agent, or Firm* — Mintz Levin Cohn Ferris Glovsky and Popeo, P.C.

(57) ABSTRACT

Various exemplary methods, systems, and devices for controlling movement of a robotic surgical system are provided. In general, a plurality of surgical instruments can be simultaneously in use during performance of a surgical procedure. One or more of the plurality of instruments can be coupled to a robotic surgical system, which can be configured to control movement of the one or more of the plurality of instruments.

21 Claims, 30 Drawing Sheets

(51) Int. Cl.
*A61B 34/20* (2016.01)
*A61B 17/00* (2006.01)
*A61B 18/14* (2006.01)

(56) References Cited

U.S. PATENT DOCUMENTS

| | | | |
|---|---|---|---|
| 6,468,265 B1 | 10/2002 | Evans et al. | |
| 6,587,750 B2 | 7/2003 | Gerbi et al. | |
| 6,837,883 B2 | 1/2005 | Moll et al. | |
| 7,169,141 B2 | 1/2007 | Brock et al. | |
| 7,250,028 B2 | 7/2007 | Julian et al. | |
| 7,265,266 B2 | 9/2007 | Zhu | |
| 7,865,266 B2 | 1/2011 | Moll et al. | |
| 8,831,782 B2 | 9/2014 | Itkowitz | |
| 9,089,353 B2* | 7/2015 | Farritor | A61B 90/30 |
| 9,216,061 B2 | 12/2015 | Mohr | |
| 9,408,670 B2 | 8/2016 | Kwak et al. | |
| 9,931,170 B2 | 4/2018 | Auld | |
| 9,949,798 B2 | 4/2018 | Weir | |
| 2003/0013949 A1 | 1/2003 | Moll et al. | |
| 2006/0074415 A1* | 4/2006 | Scott | A61B 18/1445 606/45 |
| 2006/0258938 A1 | 11/2006 | Hoffman et al. | |
| 2007/0013336 A1 | 1/2007 | Nowlin et al. | |
| 2007/0265495 A1* | 11/2007 | Vayser | A61B 1/045 600/109 |
| 2009/0088634 A1* | 4/2009 | Zhao | A61B 34/20 600/427 |
| 2009/0088897 A1* | 4/2009 | Zhao | G06K 9/3216 700/250 |
| 2009/0202387 A1 | 8/2009 | Dlugos, Jr. et al. | |
| 2009/0326318 A1* | 12/2009 | Tognaccini | A61B 34/37 600/104 |
| 2009/0326556 A1 | 12/2009 | Diolaiti et al. | |
| 2010/0317965 A1* | 12/2010 | Itkowitz | A61B 34/37 600/425 |
| 2010/0318099 A1* | 12/2010 | Itkowitz | A61B 34/30 606/130 |
| 2012/0035764 A1 | 2/2012 | Lipow et al. | |
| 2012/0158013 A1 | 6/2012 | Stefanchik et al. | |
| 2013/0211588 A1* | 8/2013 | Diolaiti | B25J 13/06 700/249 |
| 2013/0331644 A1* | 12/2013 | Pandya | A61B 1/00188 600/102 |
| 2014/0163736 A1 | 6/2014 | Azizian et al. | |
| 2014/0179997 A1 | 6/2014 | von Grunberg et al. | |
| 2014/0229007 A1 | 8/2014 | Kishi | |
| 2015/0018622 A1* | 1/2015 | Tesar | A61B 50/13 600/202 |
| 2016/0183930 A1* | 6/2016 | Herzlinger | A61B 34/37 600/118 |
| 2016/0184032 A1* | 6/2016 | Romo | B25J 9/1694 606/130 |
| 2016/0279799 A1* | 9/2016 | King | B25J 9/1697 |
| 2017/0079731 A1 | 3/2017 | Griffiths et al. | |
| 2017/0189126 A1 | 7/2017 | Weir | |
| 2017/0189131 A1 | 7/2017 | Weir | |
| 2018/0028268 A1 | 2/2018 | Nowlin et al. | |

OTHER PUBLICATIONS

U.S. Appl. No. 14/988,883, filed Jan. 6, 2016, Michael P. Weir.
U.S. Appl. No. 14/988,996, filed Jan. 6, 2016, Michael P. Weir.
U.S. Appl. No. 14/988,980, U.S. Pat. No. 9,949,798, filed Jan. 6, 2016, Michael P. Weir.
[No. Author Listed] "Biomechanics of the Hand," Computational Bioengineering Laboratory at the National University of Singapore, retrieved from <<http://www.bioeng.nus.edu.sg/compbiolab/projects/hand-biomechanics.html>>, dated Apr. 14, 2014 (4 pages).
Cleary et al., State of the art in surgical robotics: clinical applications and technology challenges. Comput Aided Surg. 2001;6(6):312-28.
Green et al., Telepresence Surgery. IEEE Engineering in Medicine and Biology. 1995;324-9.
Hao et al., The collision-free motion of robot with fuzzy neural network, 2010, IEEE, p. 219-222 (Year: 2010).
Kim et al., "A Teleoperated Minimally Invasive Surgical System with an Additional Degree of Freedom Manipulator, 2010", IEEE, (2010), 90-94.
Mack, M. Minimally invasive and robotic surgery. JAMA. Feb. 7, 2001;285(5):568-72.
Pereira et al., "Hand-Held Robotic Device for Laparoscopic Surgery and Training", 2014, IEEE, 1-8.
Roh et al., Development of the SAIT Single-Port Surgical Access Robot—Salve Arm Based on RCM Mechanism, IEEE, 2015.
Staub et al., Human-Compiter Interfaces for Interaction with Surgical Tools in Robotic Surgery, The Fourth IEEE RAS/EMBS International Conference on Biomedical Robotics and Biomechanatronics, Roma, Italy, Jun. 24-27, 2012.
Stoianovici et al., Robotic Tools for Minimally Invasive Urologic Surgery, 2002, Internet, p. 1-17.
Wu et al., "ISB recommendation on definitions of joint coordinate systems of various joints for the reporting of human joint motion—Part II: shoulder, elbow, wrist and hand,"Journal of Biomechanics 38(5): 981-992 (2005).
Zheng et al., Two Robot Arms In Assembly, 1986, IEEE, p. 1230-1235 (Year: 1986).

* cited by examiner

METHODS, SYSTEMS, AND DEVICES FOR CONTROLLING MOVEMENT OF A ROBOTIC SURGICAL SYSTEM

CROSS-REFERENCE TO RELATED APPLICATIONS

The present application claims priority to U.S. patent application Ser. No. 14/988,852 entitled "Methods, Systems, And Devices For Controlling Movement Of A Robotic Surgical System" filed Jan. 6, 2016, which is hereby incorporated by reference in its entirety.

FIELD OF THE INVENTION

The present disclosure relates generally to methods, systems, and devices for controlling movement of a robotic surgical system.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Various robotic systems have been developed to assist in MIS procedures. Robotic systems can allow for more intuitive hand movements by maintaining both natural eye-hand axis. Robotic systems can also allow for more degrees of freedom in movement by including a "wrist" joint on the instrument, creating a more natural hand-like articulation. One drawback with robotic systems, however, is the loss of direct human contact with the tissue. It can be very difficult and expensive to give true force feedback to the surgeon. Another drawback is that robotic systems traditionally only allow the surgeon to control movement of up to two surgical instruments, with any other surgical instruments having to be manually controlled by other medical personnel. It can be difficult for the surgeon and other medical personnel to communicate and synchronize activities of the separately controlled instruments during performance of a surgical procedure.

Accordingly, there remains a need for improved methods, systems, and devices for controlling movement of a robotic surgical system.

SUMMARY

In one embodiment, a surgical system is provided that includes a robotic surgical system and a controller. The robotic surgical system can include a first movable arm configured to have a first surgical instrument removably coupled thereto, can include a second movable arm configured to have a second surgical instrument removably coupled thereto, can have a first mode in which the robotic surgical system is configured to control movement of the first arm such that the first arm and the first surgical instrument removably coupled thereto move relative to the second arm and the second surgical instrument removably coupled thereto, can have a second mode in which the robotic surgical system is configured to control movement of the first arm in coordination with the second arm such that the first arm and the first surgical instrument removably coupled and the second arm and the second surgical instrument removably coupled thereto to simultaneously move in coordination. The controller can be configured to cause the coordinated movement.

The surgical system can have any number of variations. For example, in the second mode, the coordinated movement can maintain a fixed spatial relationship between the first surgical instrument and the second surgical instrument. For another example, the robotic surgical system can be configured to receive a first user selection of which one of a plurality of arms of the robotic surgical system is the first arm, and can be configured to receive a second user selection of which one of the plurality of arms of the robotic surgical system is the second arm. The robotic surgical system can be configured to receive a third user selection switching the first arm from the selected one of the plurality of instruments to another one of the plurality of instruments. For yet another example, the robotic surgical system can be configured to switch between the first and second modes in response to a user command to switch modes. For still another example, in the second mode, the coordinated movement can move at least one of the first and second surgical instruments from one anatomical quadrant of the patient to another anatomical quadrant of the patient. For another example, the first arm can have a sensor coupled thereto. The sensor can be configured to detect an impending collision of the first arm with another arm of the robotic surgical system. The robotic surgical system can include a notification mechanism configured to provide a notification to a user of the robotic surgical system in response to the sensor detecting the impending collision.

In another embodiment, a surgical system is provided that includes an electromechanical arm, a camera, and a controller. The electromechanical arm can be configured to removably couple to a surgical instrument. The electromechanical arm can be configured to move so as to move the surgical instrument removably coupled thereto relative to a patient on which a surgical procedure is being performed. The camera can have a field of view. The controller can be configured to receive an instruction from a user requesting movement of the surgical instrument from a start location outside of the field of view, move the surgical instrument in accordance with the instruction, and provide a constant cue during the movement of the surgical instrument. The cue can change during the movement of the surgical instrument in relation to a location of the surgical instrument relative to the field of view. The controller can be configured to stop the cue when the surgical instrument moves into the field of view.

The surgical system can vary in any number of ways. For example, the cue can be at least one of a visual cue and an auditory cue. For another example, the controller can be configured to repeatedly determine a current bearing of a longitudinal axis of the surgical instrument as the surgical instrument is moved by the electromechanical arm, and the controller can be configured to change the cue during the movement of the surgical instrument based on an intersection of the current bearing with the field of view. For yet another example, after the cue has been stopped, the controller can be configured to receive a second instruction from the user indicating that the user desires to adjust a position the surgical instrument, and, if the surgical instrument moves out of the field of view as a result of the adjusting, provide a notification to the user indicating that the surgical instrument has moved out of the field of view. For still another example, the surgical system can include a display device configured to display an image of the field of view visualized by the camera. The controller can be configured to repeatedly update the image throughout the movement of the surgical instrument.

In another embodiment, a surgical system is provided that includes a first electromechanical arm, a second electromechanical arm, a first sensor attached to the first arm, and a controller configured to be in electronic communication with the first sensor. The first arm can be configured to have a first surgical instrument removably coupled thereto. The first arm can be configured to move so as to adjust a position of the first surgical instrument removably coupled thereto relative to a first surgical target. The second arm can be configured to have a second surgical instrument removably coupled thereto. The second arm can be configured to move so as to adjust a position of the second surgical instrument removably coupled thereto relative to a second surgical target. The first sensor can be configured to detect an impending collision between the first and second arms by determining when the second arm is within a threshold minimum distance of the first arm. The controller can be configured to trigger performance of a remedial action in response to the detected impending collision.

The surgical system can vary in any number of ways. For example, the first sensor can be configured to detect the impending collision using energy emitted by the first sensor. The emitted energy can include at least one of light, electricity, and sound, and/or a maximum range of the emitted energy can define the threshold minimum distance. For another example, the first sensor can include a mechanical extension extending from the first arm. The mechanical extension can be configured to detect the impending collision by coming into contact with the second arm. A size of the mechanical extension can define the threshold minimum distance. For yet another example, triggering performance of the remedial action can include providing a notification to a user of the detection of the impending collision. The notification can include at least one of an audible sound, a visual display on a display device, a haptic signal, and a light. The controller can trigger the notification to be provided before the detected impending collision occurs and/or after the detected impending collision occurs. For still another example, triggering performance of the remedial action can include stopping movement of the first arm. For yet another example, triggering performance of the remedial action can include altering a previously-instructed movement path of the first arm to another movement path of the first arm determined by the controller as avoiding the impending collision. For another example, triggering performance of the remedial action can include changing a configuration of the first arm or a configuration of the second arm. For yet another example, triggering performance of the remedial action can include moving the second arm to avoid the impending collision. For another example, the second arm can have a second sensor coupled thereto, the second sensor can be configured to detect an impending collision between the first and second arms by determining when the first arm is within a threshold minimum distance of the second arm, the controller can be configured to be in electronic communication with the second sensor, and the controller can be configured to trigger performance of a remedial action in response to the impending collision detected by the second sensor. For yet another example, the surgical system can include a user input device configured to receive an input from a user indicating a desired movement of the first instrument removably coupled to the first arm. The controller can be configured to be in electronic communication with the user input device and the first arm, and the controller can be configured to control movement of the first arm based on the input received by the user input device.

In another aspect, a surgical method is provided that in one embodiment includes receiving a user selection of one of a plurality of surgical instruments as a master instrument. The plurality of surgical instruments can be controlled by a robotic surgical system during performance of a surgical procedure on a patient. Each of the plurality of surgical instruments can be coupled to one of a plurality of movable arms of the robotic surgical system. The method can include receiving a user selection of one or more other ones of the plurality of surgical instruments as follower instruments, receiving an input indicating movement of the master instrument, and causing the one or more follower instruments to move in coordination with the movement of the master instrument so as to maintain a fixed spatial relationship between the master instrument and the one or more follower instruments throughout the movement of the master instrument.

The surgical method can vary in any number of ways. For example, the movement of the master instrument can be from one anatomical quadrant of the patient to another anatomical quadrant of the patient. For another example, the plurality of surgical instruments can be located in different anatomical quadrants of the patient. For yet another example, the surgical method can include receiving an input indicating a user-requested change in visualization provided by a visualization device of at least one of the plurality of surgical instruments, and effecting the user-requested change in the visualization provided by the visualization device. The change can be effected simultaneously with the movement of the master instrument and the one or more follower instruments such that the visualization device, the master instrument, and the one or more follower instruments move at the same time, or the change can be effected either before or after the movement of the master instrument and the one or more follower instruments such that the visualization device moves at a different time than the master instrument and the one or more follower instruments. For still another example, the surgical method can include displaying on a display device showing the plurality of surgical instruments an indication of which one of the plurality of surgical instruments has been selected as the master instrument and an indication of which one or more of the plurality of surgical instruments has been selected as the one or more follower instruments. For another example, the robotic surgical system can include a controller that receives the user selection of the master instrument, receives the user selection of the one or more follower instruments, receives the input indicating the movement of the master instrument, and causes the one or more follower instruments to move in coordination with the movement of the master instrument. For yet another example, the robotic surgical system can include a first user input device and a controller in electronic communication with one another, and receiving the input indicating movement of the master instrument can include receiving at the controller an input from the first user input device. The robotic surgical system can include a second user input device in electronic communication with the controller. The second user input device can be associated with a visualization device providing visualization of at least one of the plurality of surgical instruments. The method can include receiving an input at the controller from the second user input device indicating a user-requested change in the visualization provided by the visualization device, and effecting the user-requested change in the visualization provided by the visualization device.

In another embodiment, a surgical method is provided that includes displaying an image on a display device showing a field of view of a camera visualizing a surgical area within a patient, and providing a constant cue to a user positioning a distal working end of a surgical instrument relative to the patient using a robotic surgical system to which the surgical instrument is removably coupled. The distal working end of a surgical instrument can start its movement from outside the field of view. The cue can change over time in relation to a location of the distal working end of the surgical instrument relative to the field of view displayed on the display device. The surgical method can include stopping provision of the cue in response to the distal working end of the surgical instrument entering the field of view displayed on the display device.

The surgical method can have any number of variations. For example, the cue can be at least one of a visual cue and an auditory cue. For another example, the cue can include a light that changes over time in at least one of brightness and color in relation to the location of the distal working end of the surgical instrument relative to the field of view displayed on the display device. For yet another example, the cue can include an icon shown on the display device that changes over time in relation to the location of the distal working end of the surgical instrument relative to the field of view displayed on the display device. For still another example, the cue can include an audible sound that changes over time in relation to the location of the distal working end of the surgical instrument relative to the field of view displayed on the display device. The audible sound changing can include changing a pitch of the sound or changing an amplitude of the sound. For another example, the cue changing over time in relation to the location of the distal working end of the surgical instrument relative to the field of view displayed on the display device can be based on an intersection of the field of view and a trajectory defined by a longitudinal axis of an elongate shaft of the surgical instrument. For still another example, the cue changing over time in relation to the location of the distal working end of the surgical instrument relative to the field of view displayed on the display device can be based on an intersection of the field of view and a trajectory defined by a longitudinal axis of a trocar through which the surgical instrument is advanced into the patient. For another example, the cue can change over time based on at least one of a direction that the distal working end of the surgical instrument is moving in relative to the field of view displayed on the display device, a distance between the distal working end of the surgical instrument and the field of view displayed on the display device, and whether the distal working end of the surgical instrument is moving closer to or farther from the field of view displayed on the display device. For yet another example, the surgical method can include, after the cue has stopped being provided, adjusting a position of the distal working end of the surgical instrument, and, if the distal working end of the surgical instrument moves out of the field of view as a result of the adjusting, providing a notification to the user indicating that the distal working end of the surgical instrument has moved out of the field of view. For still another example, the robotic surgical system can include a plurality of electromechanical arms. The surgical instrument can be removably coupled to one of the arms. The location of the distal working end of the surgical instrument relative to the field of view displayed on the display device can be determined based on a position of the one of the arms to which the surgical instrument is removably coupled.

In another embodiment, a surgical method is provided that includes receiving an input from a user indicating that the user desires to move a surgical instrument currently out of a field of view of a camera visualizing a surgical area of a patient. The surgical instrument can be coupled to an electromechanical arm of a robotic surgical system that moves the surgical instrument relative to the patient. The surgical method can include calculating a bearing of a trajectory line between a trocar, through which the surgical instrument is advanced, and a point in the surgical area being visualized in the field of view. The surgical method can include repeatedly determining a current bearing of a longitudinal axis of the surgical instrument as the surgical instrument is moved by movement of the electromechanical arm, and providing a cue indicative of a difference between the bearing of the trajectory line and the current bearing of the longitudinal axis. The cue can change over time based on an amount of the difference as the surgical instrument moves. The surgical method can include stopping provision of the cue when the difference becomes substantially zero.

The surgical method can have any number of variations. For example, providing the cue can include at least one of providing a visual cue and providing an auditory cue. For another example, the surgical method can include displaying an image on a display device showing the field of view of the camera. For yet another example, the surgical method can include, after the cue has stopped being provided, receiving a second input from the user indicating that the user desires to adjust a position the surgical instrument currently in the field of view of the camera, and, if the surgical instrument moves out of the field of view as a result of the adjusting, providing a notification to the user indicating that the surgical instrument has moved out of the field of view.

In another embodiment, a surgical method is provided that includes moving a first electromechanical arm of a robotic surgical system that includes one or more additional electromechanical arms. Each of the arms can have a surgical instrument coupled thereto. The surgical method can include sensing an impending collision between the moving first arm and one of the one or more additional electromechanical arms using a sensor attached to the first arm, and in response to sensing the impending collision, performing a remedial action that addresses the sensed impending collision prior to occurrence of the sensed impending collision.

The method can vary in any number of ways. For example, performing the remedial action can include providing a notification to a user of the sensed impending collision. The notification includes at least one of an audible sound, a visual display on a display device, a haptic signal, and a light. For another example, performing the remedial action can include stopping the movement of the first arm. For yet another example, the movement of the first arm can be along a predetermined path defined by a user, and performing the remedial action can include changing the predetermined path to avoid the impending collision. For still another example, performing the remedial action can include changing a shape of the first arm or a shape of the one of the one or more additional electromechanical arms.

In another embodiment, a surgical method is provided that includes displaying on a display device an image of a surgical area visualized by a camera. The camera has a field of view defining a perimeter of the visualized surgical area. The surgical method can include providing a signal indicative of a current position of a surgical instrument, which can be located outside the perimeter of the visualized surgical area, relative to the visualized surgical area. The surgical instrument can be coupled to an electromechanical arm of a robotic surgical system. The surgical method can include changing the signal in real time with movement of the electromechanical arm and the surgical instrument coupled thereto relative to the visualized surgical area based on the current position of the surgical instrument relative to the surgical area.

The surgical method can vary in any number of ways. For example, the surgical method can include stopping the signal in response to the surgical instrument moving to a location inside the perimeter of the visualized surgical area. For another example, the surgical method can include determining the current position of the surgical instrument relative to the surgical area based on a position of a longitudinal axis of the surgical instrument relative to the visualized surgical area. The signal can be changed in real time based on an intersection of the longitudinal axis with the visualized surgical area. For yet another example, the surgical method can include determining the current position of the surgical instrument relative to the surgical area based on a position of a longitudinal axis of a trocar, through which the surgical instrument is advanced, with the visualized surgical area. The signal can be changed in real time based on an intersection of the longitudinal axis with the visualized surgical area. For still another example, the signal can be changed in real time based on a proximity of a current position of the surgical instrument to a reference point within of the visualized surgical area. For another example, the signal can be changed in real time based on a proximity of a current position of a trocar, through which the surgical instrument is advanced, to a reference point within the visualized surgical area. For still another example, the surgical method can include calculating the current position of the surgical instrument relative to the surgical area using a controller of the robotic surgical system. For yet another example, the signal can include at least one of an audible sound, a visual signal shown on the display device, a visual signal shown on a second display device, a tactile signal palpable by a user of the robotic surgical system, and an illuminated light. The signal can include at least the audible sound, and changing the signal can include changing a pitch of the sound or changing an amplitude of the sound. The signal can include at least one of the visual signal shown on the display device and the visual signal shown on the second display device, and changing the signal can include changing an appearance of the at least one of the visual signal shown on the display device and the visual signal shown on the second display device. The signal can include at least the illuminated light, and changing the signal can include changing the light in at least one of brightness and color.

In another embodiment, a surgical method is provided that includes receiving a user input at a robotic surgical system. The user input can request movement of a surgical instrument removably and replaceably coupled to a first electrosurgical arm of the robotic surgical system. The surgical method can include causing movement of the first electrosurgical arm in response to the received user input, thereby causing movement of the surgical instrument removably and replaceably coupled to the first electrosurgical arm. The surgical method can include determining in real time with the movement of the first electrosurgical arm whether the first electrosurgical arm is within a threshold minimum distance of another portion of the robotic surgical system, and, in response to determining that the first electrosurgical arm is within the threshold minimum distance, triggering performance of a remedial action to reduce a chance of a collision between the moving first electrosurgical arm and the other portion of the robotic surgical system.

The surgical method can have any number of variations. For example, the performance of the remedial action can include at least one of slowing a speed of the moving first electrosurgical arm, adjusting the movement of the first electrosurgical arm in contradiction to the movement requested by the user input, moving the other portion of the robotic surgical system, and providing a notification to a user indicating that the first electrosurgical arm is within the threshold minimum distance. For another example, the other portion of the robotic surgical system can include a second electromechanical arm of the robotic surgical system that is configured to removably and replaceably couple to a second surgical instrument.

In another embodiment, a surgical method is provided that includes receiving a first user input at a robotic surgical system. The first user input can request movement of a first surgical instrument coupled to a first electromechanical arm of the robotic surgical system. The surgical method can include, in response to the received first user input, moving the first electromechanical arm in a first mode of the robotic surgical system in which the first electromechanical arm moves relative to a second electromechanical arm of the robotic surgical system such that a relative position of the first and second electromechanical arms changes. The surgical method can include receiving a second user input at the robotic surgical system. The second user input can request another movement of the first surgical instrument. The surgical method can include, in response to the received second user input, moving the first electromechanical arm in a second mode of the robotic surgical system in which the other movement of the first electromechanical arm causes corresponding movement of the second electromechanical arm such that the relative position of the first and second electromechanical arms is maintained.

The surgical method can vary in any number of ways. For example, the surgical method can include receiving a third user input at the robotic surgical system. The third user input can set the robotic surgical system in one of the first and second modes. For another example, the robotic surgical system can include one or more additional electromechanical arms. In the first mode, the first electromechanical arm can move relative to each of the one or more additional electromechanical arms. In the second mode, the other movement of the first electromechanical arm can cause corresponding movement of each of the one or more additional electromechanical arms. For yet another example, the robotic surgical system can include a plurality of electromechanical arms in addition to the first electromechanical arm. The surgical method can include receiving a third user input at the robotic surgical system indicating a user choice of which of the plurality of electromechanical arms is the second electromechanical arm that moves with the first electromechanical arm in the second mode.

Non-transitory computer program products (i.e., physically embodied computer program products) are also provided that store instructions, which when executed by one or more processors of one or more computer systems, causes at least one processor to perform operations herein. Similarly, computer systems are also provided that can include one or more processors and one or more memories coupled to the one or more processors. Each of the one or more memories can temporarily or permanently store instructions that cause at least one processor to perform one or more of the operations described herein. In addition, methods can be implemented by one or more processors either within a single computer system or distributed among two or more computer systems. Such computer systems can be connected and can exchange data and/or commands or other instructions or the like via one or more connections, including but not limited to a connection over a network (e.g., the Internet, a wireless wide area network, a local area network, a wide area network, a wired network, etc.), via a direct connection between one or more of the multiple computer systems, etc.

BRIEF DESCRIPTION OF DRAWINGS

This invention will be more fully understood from the following detailed description taken in conjunction with the accompanying drawings, in which.

DETAILED DESCRIPTION

Figure 1:
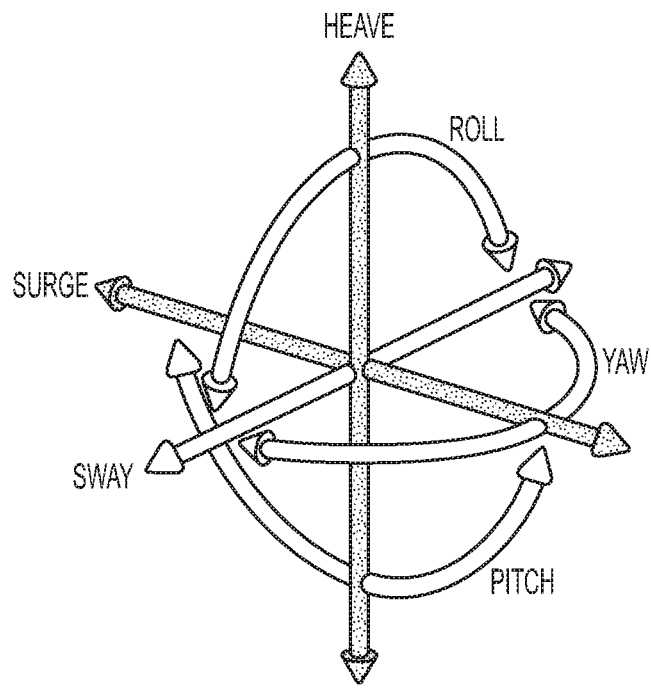
FIG. 1 is a graphical representation of terminology associated with six degrees of freedom.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods, systems, and devices for controlling movement of a robotic surgical system are provided. In general, a plurality of surgical instruments can be simultaneously in use during performance of a surgical procedure. One or more of the plurality of instruments can be coupled to a robotic surgical system, which can be configured to control movement of the one or more of the plurality of instruments. In some embodiments, the robotic surgical system can be configured to control movement of all of the plurality of instruments. In other embodiments, the robotic surgical system can be configured to control movement of at least one of the plurality of instruments, and movement of a remainder of the plurality of surgical instruments can be controlled in another way, e.g., by another robotic surgical system or through manual user control.

During performance of the surgical procedure, movement of the plurality of surgical instruments by the robotic surgical system relative to one or more others of the surgical instruments and/or relative to a surgical site can create any one or more of a variety of challenges. For example, it can be difficult for the robotic surgical system to move one of the surgical instruments from a position out of frame of vision of another one of the surgical instruments configured to provide visualization to a position within the frame of vision because, e.g., the frame of vision can be fixed to a specific surgical area of interest and not to the area from which the one of the surgical instruments is being moved, such as from outside the patient's body. For another example, movement of one or more of the surgical instruments by the robotic surgical system can risk collision between objects, such as between a part of the robotic surgical system (e.g., a part moving to move the surgical instrument) and a non-moving one of the surgical instruments, another part of the robotic surgical system, a mounted light illuminating the surgical area, a surgical table, etc., which can risk damage to one or both of the colliding objects and/or can risk harming the patient. For yet another example, controlling movement of any one or more of the surgical instruments from one location to another using the robotic surgical system can be difficult when the movement is from one anatomical quadrant of a patient to another, e.g., from one quadrant of the patient's abdomen to another quadrant of the abdomen, because in at least some robotic surgical systems each quadrant may have its own reference Cartesian frame. For still another example, when one of the surgical instruments moves, it may move out of a frame of vision of another one of the surgical instruments configured to provide visualization (e.g., a camera), which can make the location of the one of the surgical instruments and/or the surgical area more difficult for a surgeon and/or other medical personnel to assess.

At least some of the methods, systems, and devices for controlling movement of a robotic surgical system provided herein can be configured to facilitate movement of a surgical instrument into a field of view of a camera visualizing a surgical area. In general, a robotic surgical system having a surgical instrument coupled thereto can be configured to signal a user of the robotic surgical system with information regarding a location of the surgical instrument relative to a field of view of a camera visualizing a surgical area, e.g., relative to an area of space currently being visualized by a lens of the camera. The information can allow the user to control movement of the surgical instrument by the robotic surgical system to effectively guide the surgical instrument from out of the camera's field of view and into the camera's field of view. The signal can be configured to change in real time with the surgical instrument's movement based on a position of the surgical instrument relative to the field of view and/or based on a position of an introducer device (e.g., a cannula, a trocar, etc.) through which the surgical instrument is advanced to gain access to a patient's body. The signal may thus facilitate accurate guidance of the surgical instrument to the field of view, may allow for corrective movement of the surgical instrument based on the signal's change (e.g., correct for the instrument being moved off course from intersection with the field of view, etc.), and/or may facilitate "blind" positioning of the surgical instrument by allowing the surgical instrument to be accurately guided to the field of view without the surgical instrument being visualized by the user (direct visualization or indirect visualization on a display device) during the instrument's movement to the field of view. The signal can be configured to be visualized by the user (e.g., a light, text on a display device, an icon on a display device, etc.), to be heard by the user (e.g., an audible tone, a computerized voice, etc.), or to be tactilely felt by the user (e.g., a vibration, heat, cooling, etc.). The signal include one or more signals, and the signal can be visual, auditory, and/or tactile.

At least some of the methods, systems, and devices for controlling movement of a robotic surgical system provided herein can be configured to facilitate detection of collision of a portion of the robotic surgical system with another object. In general, a robotic surgical system can be configured to detect a collision between two objects before the collision happens. Detecting the collision before it occurs may allow the robotic surgical system to trigger performance of a corrective action aimed at preventing the collision from occurring, thereby reducing chances of the collision occurring and, in the event that the collision nevertheless occurs, reduce chances of the colliding objects from being damaged by reducing severity of the collision (e.g., by reducing an impact force between the colliding objects, by reorienting the position of the collided portion of the robotic surgical system prior to the collision, etc.). In an exemplary embodiment, the robotic surgical system can include a movable arm configured to have a surgical instrument coupled thereto, and the robotic surgical system can be configured to, while the arm is moving with the surgical instrument coupled thereto, detect a collision of the arm with another object before the collision occurs and trigger performance of a corrective action to help prevent the collision from occurring.

At least some of the methods, systems, and devices for controlling movement of a robotic surgical system provided herein can be configured to facilitate movement of a surgical instrument between different anatomical quadrants. In general, a robotic surgical system having a surgical instrument coupled thereto can be configured to control movement of a master surgical instrument coupled to the robotic surgical system in response to user input to the robotic surgical system, and to cause corresponding movement of one or more follower surgical instruments coupled to the robotic surgical system. The robotic surgical system may thus facilitate movement of surgical instruments between different anatomical quadrants by allowing instruments to move in correspondence to another surgical instrument and/or may reduce chances of instrument collision since multiple instruments can correspondingly move so as to maintain their spatial relationship. The robotic surgical system can be configured to allow the user to select the follower surgical instruments from among all surgical instruments coupled to the robotic surgical system, which may allow the user to select coordinated instrument movement on an as-needed basis during performance of a surgical procedure, may allow different instruments during the course of a surgical procedure to serve as a master surgical instrument that other instrument(s) follow, and/or may allow zero follower instruments to be selected such that the master surgical instrument can move relative to all the other surgical instruments coupled to the robotic surgical system. In an exemplary embodiment, first and second surgical instruments can be coupled to the robotic surgical system, with the first surgical instrument including a camera. The robotic surgical system can thus be configured to allow the camera to follow movement of the second surgical instrument, e.g., the camera is selected as the follower instrument and the second surgical instrument is selected as the master instrument, which can help maintain visualization of the second surgical instrument during movement thereof. The robotic surgical system can also thus be configured to allow the second surgical instrument to follow movement of the camera, e.g., the second surgical instrument is selected as the follower instrument and the camera is selected as the master instrument, which can allow the second surgical instrument, when visualized by the camera, to remain within the camera's vision during the camera's movement.

Terminology

There are a number of ways in which to describe the movement of components of a surgical system, as well as its position and orientation in space. One particularly convenient convention is to characterize movement in terms of degrees of freedom. The degrees of freedom are the number of independent variables that uniquely identify a component's pose (e.g., location defined by translation and orientation defined by rotation) or configuration. The set of Cartesian degrees of freedom is usually represented by the three translational or position variables, e.g., surge, heave, sway, and by the three rotational or orientation variables, e.g., Euler angles or roll, pitch, yaw, that describe the position and orientation of a component of a surgical system with respect to a given reference Cartesian frame. As used herein, and as illustrated in FIG. 1, the term "surge" refers to forward and backward movement, the term "heave" refers to movement up and down, and the term "sway" refers to movement left and right. With regard to the rotational terms, "roll" refers to tilting side to side, "pitch" refers to tilting forward and backward, and "yaw" refers to turning left and right. In a more general sense, each of the translation terms refers to movement along one of the three axes in a Cartesian frame, and each of the rotational terms refers to rotation about one of the three axes in a Cartesian frame.

Although the number of degrees of freedom is at most six, a condition in which all the translational and orientational variables are independently controlled, the number of joint degrees of freedom is generally the result of design choices that involve considerations of the complexity of the mechanism and the task specifications. For non-redundant kinematic chains, the number of independently controlled joints is equal to the degree of mobility for an end effector. For redundant kinematic chains, the end effector will have an equal number of degrees of freedom in Cartesian space that will correspond to a combination of translational and rotational motions. Accordingly, the number of degrees of freedom can be more than, equal to, or less than six.

With regard to characterizing the position of various components of the surgical system and the mechanical frame, the terms "forward" and "rearward" may be used. In general, the term "forward" refers to an end of the surgical system that is closest to the distal end of the input tool, and when in use in a surgical procedure, to the end disposed within a patient's body. The term "rearward" refers to an end of the surgical system farthest from the distal end of the input tool, and when in use, generally to the end farther from the patient.

The terminology used herein is not intended to limit the invention. For example, spatially relative terms, e.g., "superior," "inferior," "beneath," "below," "lower," "above," "upper," "rearward," "forward," etc., may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "inferior to" or "below" other elements or features would then be "superior to" or "above" the other elements or features. Likewise, descriptions of movement along and around various axes includes various special device positions and orientations. As will be appreciated by those skilled in the art, specification of the presence of stated features, steps, operations, elements, and/or components does not preclude the presence or addition of one or more other features, steps, operations, elements, components, and/or groups described herein. In addition, components described as coupled may be directly coupled, or they may be indirectly coupled via one or more intermediate components.

There are several general aspects that apply to the various descriptions below. For example, at least one surgical end effector is shown and described in various figures. An end effector is the part of a minimally invasive or invasive surgical instrument or assembly that performs a specific surgical function, e.g., forceps/graspers, needle drivers, scissors, electrocautery hooks, staplers, clip appliers/removers, suction tools, irrigation tools, etc. Any end effector can be utilized with the surgical system described herein. Further, in exemplary embodiments, an end effector can be configured to be manipulated by a user input tool. The input tool can be any tool that allows successful manipulation of the end effector, whether it be a tool similar in shape and style to the end effector, such as an input tool of scissors similar to end effector scissors, or a tool that is different in shape and style to the end effector, such as an input tool of a glove dissimilar to end effector graspers, and such as input tool of a joystick dissimilar to end effector graspers. In at least some embodiments, the input tool can be a larger scaled version of the end effector to facilitate ease of use. Such a larger scale input tool can have finger loops or grips of a size suitable for a user to hold. However, the end effector and the input tool can have any relative size.

A slave tool, e.g., a surgical instrument, of the surgical system can be positioned inside a patient's body cavity through an access point in a tissue surface for minimally invasive surgical procedures. Typically, cannulas such as trocars are used to provide a pathway through a tissue surface and/or to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In at least some embodiments, the cannula can have a housing coupled thereto with two or more sealed ports for receiving various types of instruments besides the slave assembly. As will be appreciated by a person skilled in the art, any of the surgical system components disclosed herein can have a functional seal disposed thereon, therein, and/or therearound to prevent and/or reduce insufflation leakage while any portion of the surgical system is disposed through a surgical access port, such as a cannula. The surgical system can also be used in open surgical procedures. As used herein, a surgical access point is a point at which the slave tool enters a body cavity through a tissue surface, whether through a cannula in a minimally invasive procedure or through an incision in an open procedure.

Computer Systems

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and an input device, e.g., a mouse, a trackball, a hand tracker, a gesture recognition device, Kinect, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 2:
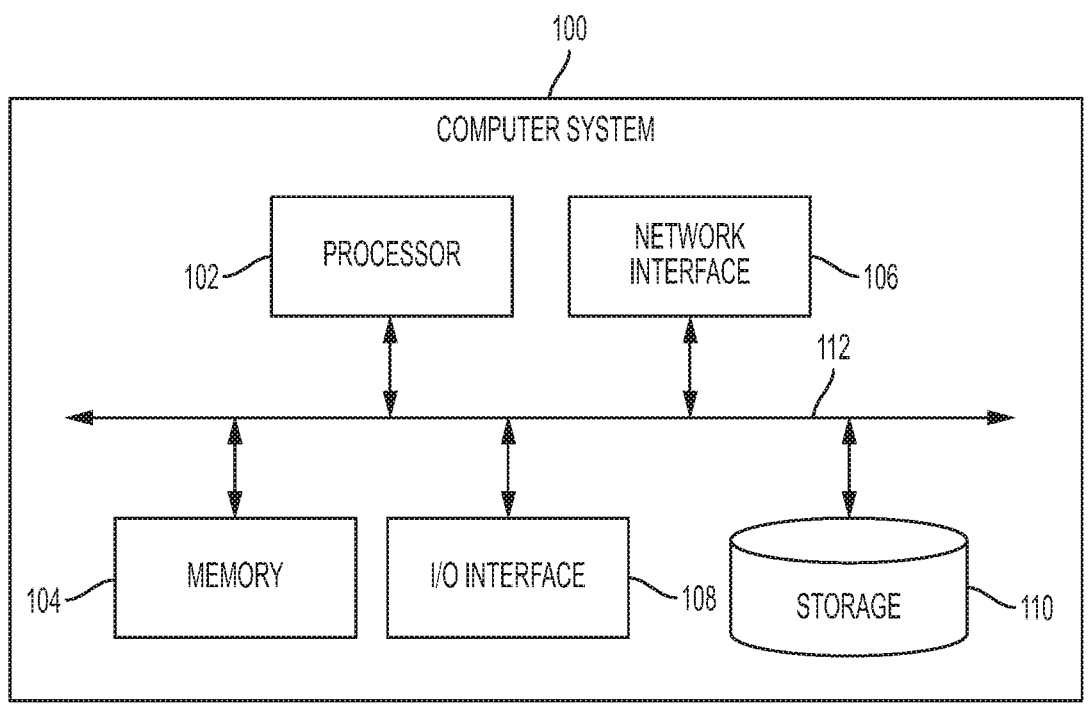
FIG. 2 is a schematic view of one embodiment of a computer system.

FIG. 2 illustrates one exemplary embodiment of a computer system 100. As shown, the computer system 100 can include one or more processors 102 which can control the operation of the computer system 100. "Processors" are also referred to herein as "controllers." The processor(s) 102 can include any type of microprocessor or central processing unit (CPU), including programmable general-purpose or special-purpose microprocessors and/or any one of a variety of proprietary or commercially available single or multi-processor systems. The computer system 100 can also include one or more memories 104, which can provide temporary storage for code to be executed by the processor(s) 102 or for data acquired from one or more users, storage devices, and/or databases. The memory 104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 100 can be coupled to a bus system 112. The illustrated bus system 112 is an abstraction that represents any one or more separate physical busses, communication lines/interfaces, and/or multi-drop or point-to-point connections, connected by appropriate bridges, adapters, and/or controllers. The computer system 100 can also include one or more network interface(s) 106, one or more input/output (IO) interface(s) 108, and one or more storage device(s) 110.

The network interface(s) 106 can enable the computer system 100 to communicate with remote devices, e.g., other computer systems, over a network, and can be, for non-limiting example, remote desktop connection interfaces, Ethernet adapters, and/or other local area network (LAN) adapters. The IO interface(s) 108 can include one or more interface components to connect the computer system 100 with other electronic equipment. For non-limiting example, the IO interface(s) 108 can include high speed data ports, such as universal serial bus (USB) ports, 1394 ports, Wi-Fi, Bluetooth, etc. Additionally, the computer system 100 can be accessible to a human user, and thus the IO interface(s) 108 can include displays, speakers, keyboards, pointing devices, and/or various other video, audio, or alphanumeric interfaces. The storage device(s) 110 can include any conventional medium for storing data in a non-volatile and/or non-transient manner. The storage device(s) 110 can thus hold data and/or instructions in a persistent state, i.e., the value is retained despite interruption of power to the computer system 100. The storage device(s) 110 can include one or more hard disk drives, flash drives, USB drives, optical drives, various media cards, diskettes, compact discs, and/or any combination thereof and can be directly connected to the computer system 100 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 2 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 100 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 100 can also include a web server for generating and/or delivering the web pages to client computer systems.

In an exemplary embodiment, the computer system 100 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Robotic Surgical Systems

The systems, devices, and methods disclosed herein can be implemented using a robotic surgical system. Various embodiments of robotic surgical systems are described in further detail in U.S. Pat. No. 8,831,782 filed Jul. 15, 2013 entitled "Patient-Side Surgeon Interface For A Teleoperated Surgical Instrument," Intl. Pat. Pub. No. WO2014151621 filed Mar. 13, 2014 entitled "Hyperdexterous Surgical System," Intl. Pat. Pub. No. WO2014151952 filed Mar. 13, 2014 entitled "Compact Robotic Wrist," and U.S. Pat. Pub. No. 2012/0158013 filed Dec. 17, 2010 entitled "Surgical System And Methods For Mimicked Motion," which are hereby incorporated by reference in their entireties.

As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

Figure 3:
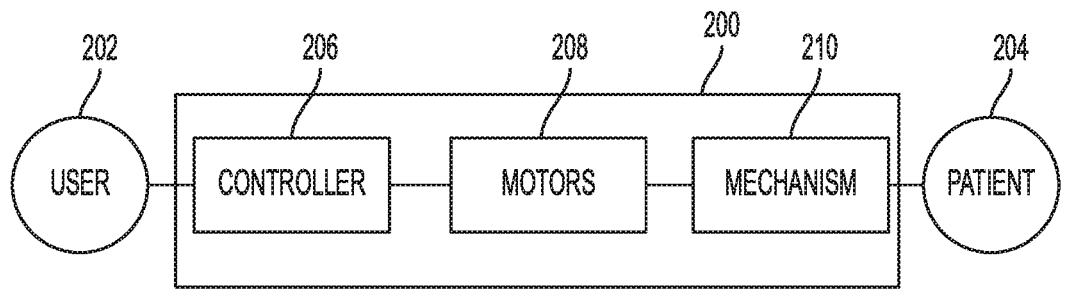
FIG. 3 is a schematic view of one embodiment of a robotic surgical system configured to be operated by a user and to be used during performance of a surgical procedure on a patient.

FIG. 3 illustrates an embodiment of a robotic surgical system 200 configured to be used by a user 202 (e.g., a surgeon, a surgical assistant, etc.) during performance of a surgical procedure on a patient 204. As in this illustrated embodiment, the robotic surgical system 200 can include a controller 206, motors 208, and a movement mechanism 210. The controller 206 can be configured to receive an input from the user 202 requesting movement, relative to the patient 204, of a surgical instrument coupled to the movement mechanism 210. The controller 206 can be configured to cause the motors 208 to drive movement of the movement mechanism 210, thereby causing the movement of the surgical instrument requested by the user 202. Although the illustrated robotic surgical system 200 includes a plurality of motors 208, a robotic surgical system can include a single motor. Similarly, although the illustrated robotic surgical system 200 includes a single controller 206 and a single movement mechanism 210, a robotic surgical system can include a plurality of controllers and/or a plurality of movement mechanisms.

In an exemplary embodiment, the movement mechanism 210 can include an arm. The arm can be configured to move so as to cause movement of a surgical instrument coupled thereto in any one or more of the three translational directions (surge, heave, and sway) and in any one or more of the three rotational directions (roll, pitch, and yaw) in response to control by the controller 206. In an exemplary embodiment, the arm can be configured to provide a plurality of degrees of freedom. More than six degrees of freedom can be provided in a variety of ways, as mentioned above and as will be appreciated by a person skilled in the art. In general, the arm can include a mechanical member configured to move in response to an input to the system 200 from the user 202. The user's input can be configured to cause the controller 206 to transmit an electronic signal to the motors 208 that causes the motors 208 to provide a force (e.g., torque) to the arm, thereby causing movement of the arm. The arm can include a plurality of members jointed together, which can facilitate movement of the arm in a plurality of degrees of freedom via bending, twisting, etc. at various ones of the joints.

The arm can include an electromechanical arm. The electromechanical arm can include one or more mechanical members configured to move in response to an electronic input. Examples of mechanical members that can form the arm include elongate shafts, coupling mechanisms (e.g., clips, magnets, snap fit mechanisms, shaped members configured to seat an instrument therein by interference fir or press fit, clamps, protrusions configured to be seated in corresponding depressions formed in a surgical instrument, depressions configured to receive therein corresponding protrusions extending from a surgical instrument, etc.) configured to removably and replaceably couple a surgical instrument to the arm, and joints (e.g., hinges, gimbals, etc.).

Figure 4:
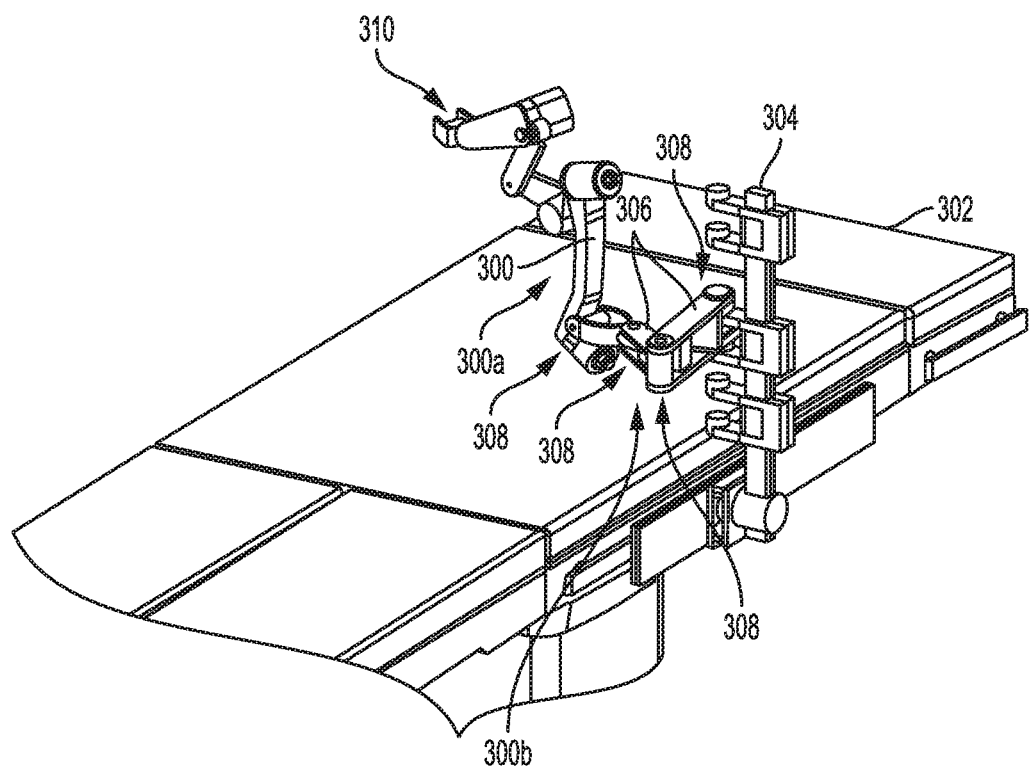
FIG. 4 is a perspective view of one embodiment of an arm of a robotic surgical system, the arm being mounted to a surgical table.
Figure 5:
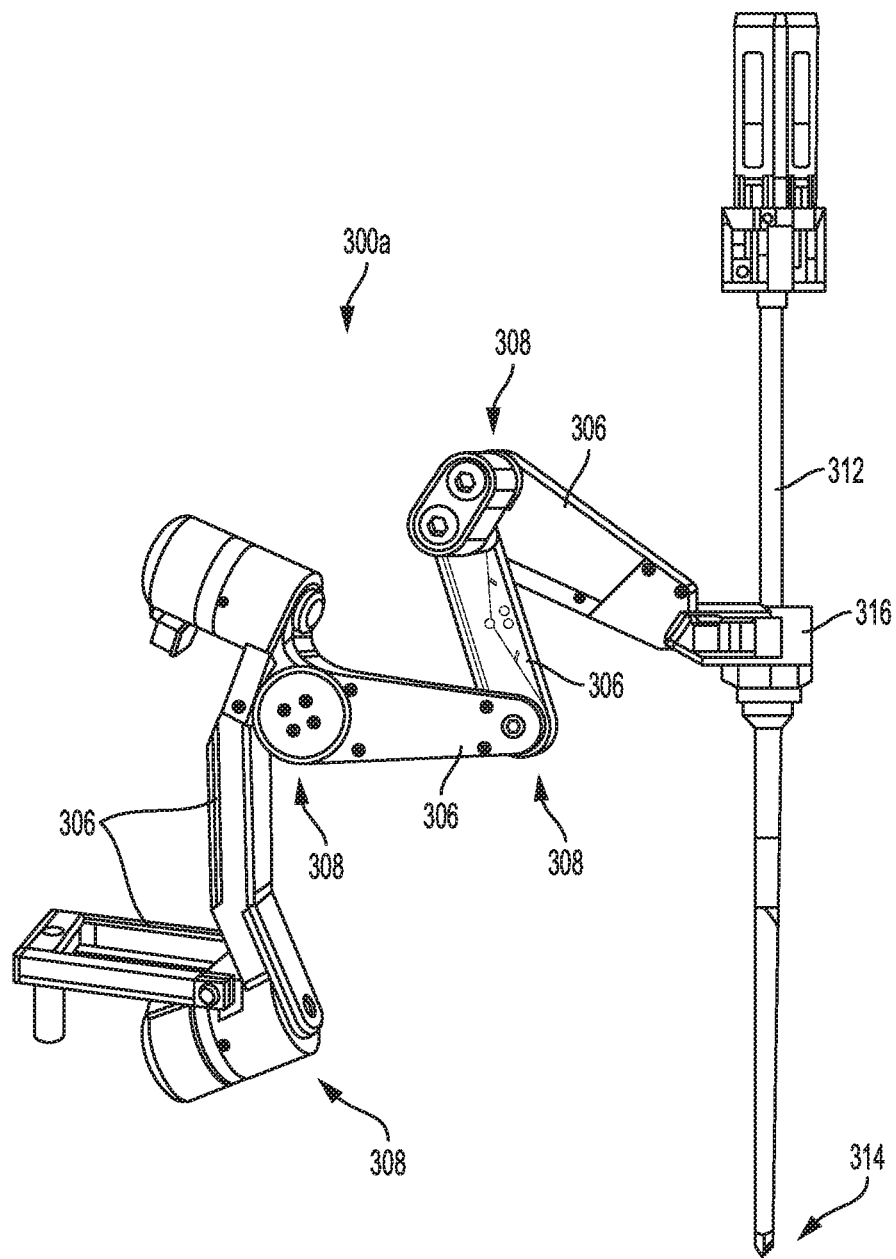
FIG. 5 is a perspective view of an active portion of the arm of FIG. 4.

FIGS. 4 and 5 illustrate an embodiment of an arm 300 in the form of an electromechanical arm. The arm 300 is mounted to a surgical table 302 using a frame 304 in the illustrated embodiment of FIG. 4, but the arm 300 can be mounted to any of a variety of stationary items, a wall, a table, a cart, the ceiling, etc., in any of variety of ways to help stabilize the arm 300 for use during a surgical procedure. The arm 300 can include an active portion 300a configured to be actively controlled, e.g., configured to move in response to electronic input, and a passive portion 300b configured to be passively controlled, e.g., configured to move in response to hand or other manual movement thereof. The passive portion 300b can lack motors or other electrical features, while the active portion 300a can include motors and other electrical features, such as associated with the joints, to facilitate electronic control thereof. In at least some embodiments, an arm can lack a passive portion so as to be configured to be entirely actively controlled. While the active and passive portions 300a, 300b are sometimes referred to herein as components of a single arm, a person skilled in the art will appreciate that the active portion 300a and the passive portion 300b can be separate arms that are matable to each other.

The arm 300 can, as in this illustrated embodiment, include a plurality of mechanical members 306, a plurality of joints 308, and a coupling mechanism 310. Adjacent ones of the mechanical members 306 can be attached together at one of joints 308. In this illustrated embodiment, the active portion 300a of the arm 300 includes five mechanical members 306 and four joints 308, the passive portion 300b of the arm 300 includes two mechanical members 306 and three joints 308, and the arm 300 includes another joint 308 between the active and passive portions 300a, 300b, but arms can have any number of mechanical members and associated joints in its active and passive portions.

As shown in FIG. 5, the arm 300, e.g., the active portion 300a thereof, can be configured to removably and replaceably couple to a surgical instrument 312 via the coupling mechanism 310. A distal end 314 of the instrument 312 can be configured to be advanced into a body of a patient, e.g., through an incision, through a natural orifice, etc. The instrument's distal end 314 can thus include a working end of the instrument 312 configured to facilitate performance of the surgical procedure within the patient. The instrument's distal end 314 can include an end effector, e.g., forceps/graspers, needle drivers, scissors, electrocautery hooks, staplers, clip appliers/removers, suction tools, irrigation tools, etc. As in this illustrated embodiment, the instrument 312 can be advanced into a patient's body through a cannula 316 (e.g., a trocar, an introducer tube, etc.). The coupling mechanism 310 is shown in FIG. 5 coupled to the cannula 316, which has the surgical instrument 312 advanced therethrough.

Aspects of the arm 300 and the frame 304 are further described in previously mentioned Intl. Pat. Pub. No. WO2014151621 filed Mar. 13, 2014 entitled "Hyperdexterous Surgical System" and Intl. Pat. Pub. No. WO2014151952 filed Mar. 13, 2014 entitled "Compact Robotic Wrist."

Figure 6:
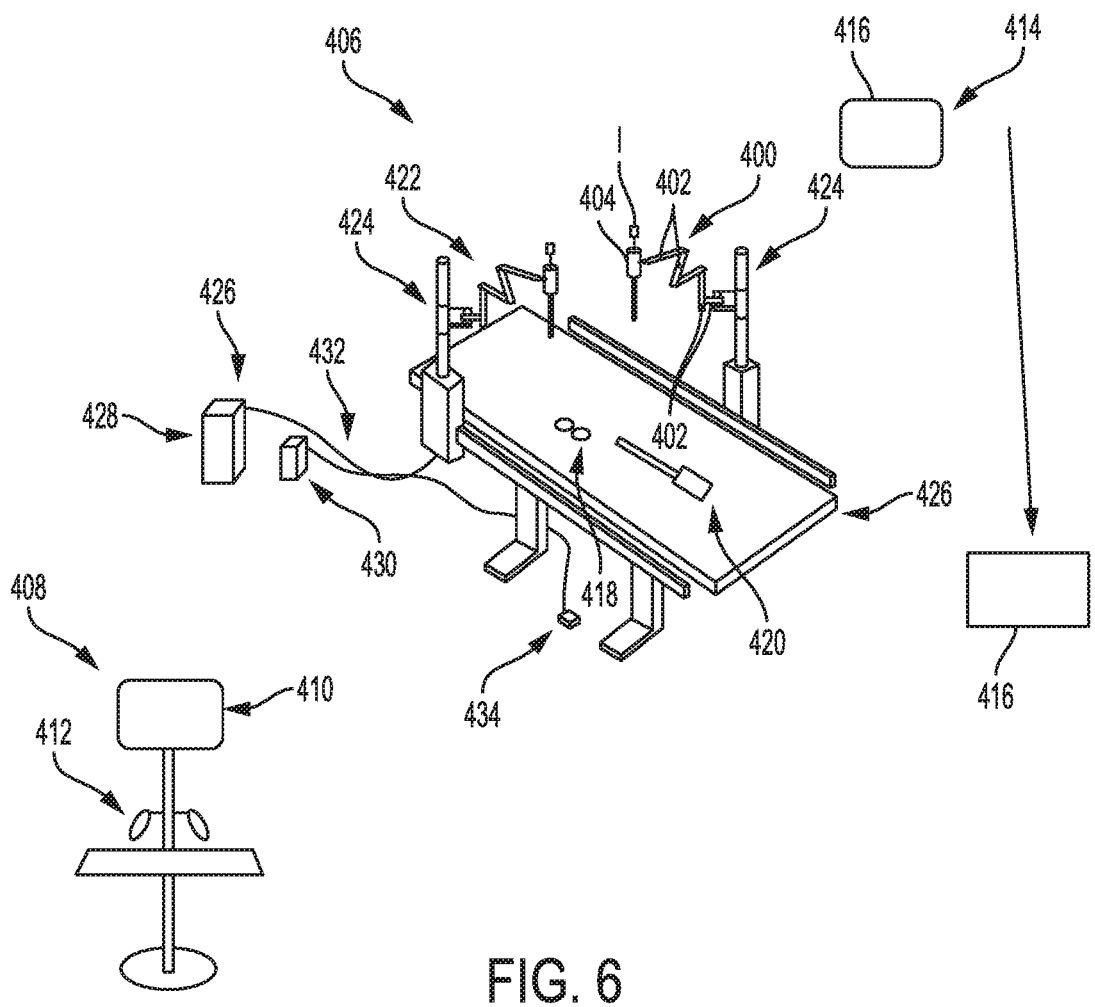
FIG. 6 is a perspective view of one embodiment of a robotic surgical system.

FIG. 6 illustrates another embodiment of an arm 400 in the form of an electromechanical arm. The arm 400 can generally be configured and used similar to the arm 300 of FIGS. 4 and 5. The arm 400 can include a plurality of mechanical members 402, a plurality of joints between adjacent ones of the arms 402, and a coupling mechanism 404 configured to removably and replaceably couple to a surgical instrument I. The arm 400 includes five mechanical members 402 and four joints in this illustrated embodiment, but as mentioned above, arms can have any number of mechanical members and associated joints.

Figure 7:
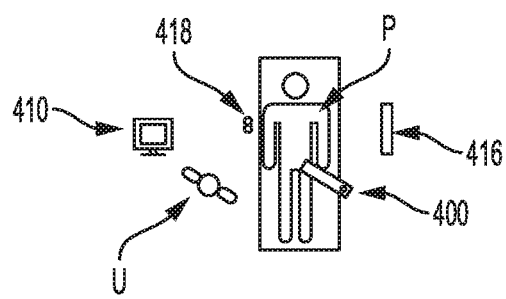
FIG. 7 is a schematic view of one embodiment of the robotic surgical system of FIG. 6 in use during performance of a surgical procedure on a patient.
Figure 8:
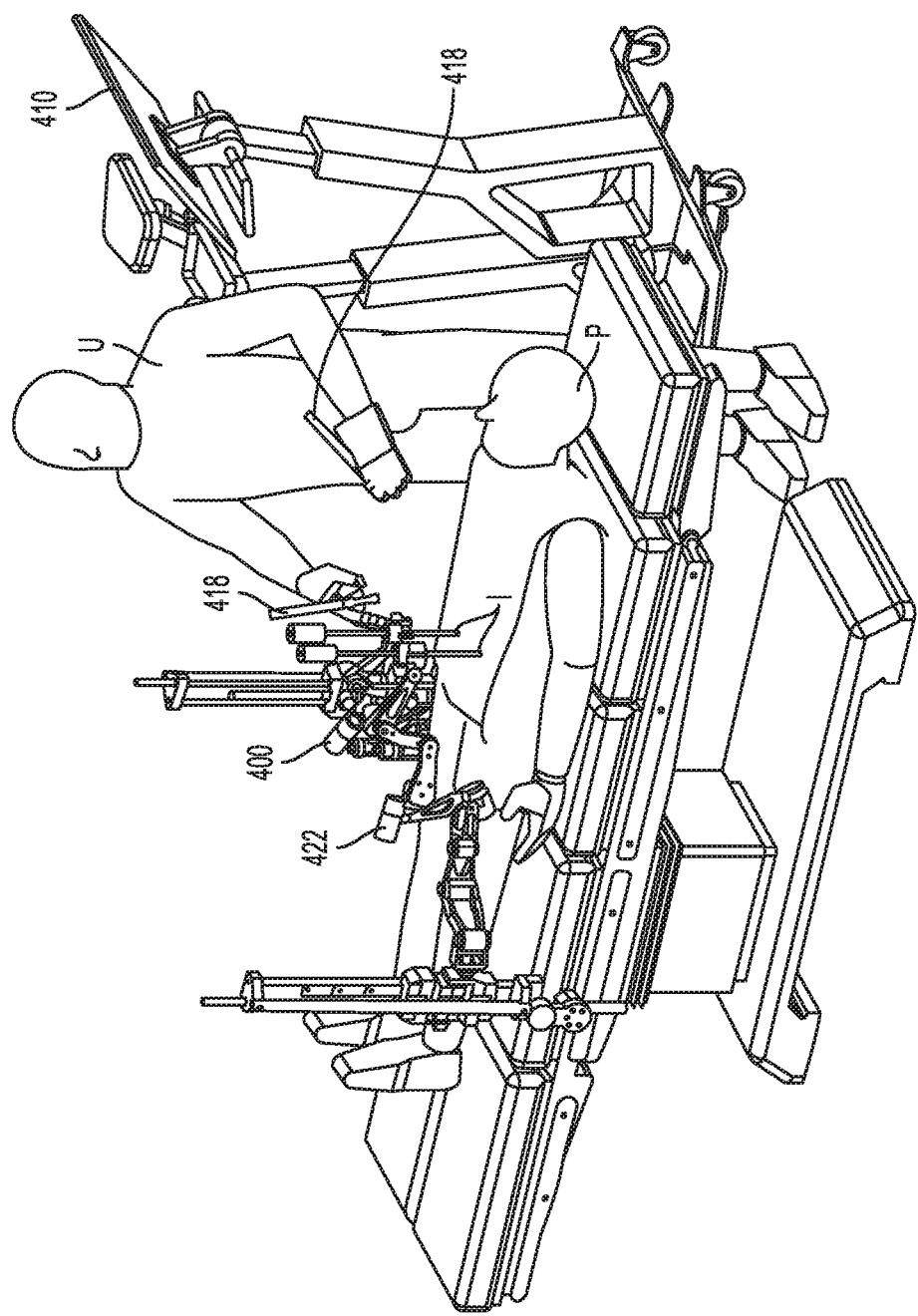
FIG. 8 is a perspective view of the robotic surgical system of FIG. 7 in use during performance of the surgical procedure on a patient.

As shown in FIGS. 6 and 7, the arm 400 can be included in a robotic surgical system 406 configured to facilitate performance of a surgical procedure on a patient P. FIG. 8 shows an example of the system 406 in use. As in this illustrated embodiment, the system 406 can include a user interface sub-system 408 that can include at least one display 410 configured to display information thereon to a user U, at least one user input device 412 configured to receive a user input thereto to control movement of the arm 400, a visualization system 414 that can include at least one display 416 configured to display thereon image(s) of a surgical procedure being performed using the system 406, a freely movable user input device 418 (shown as pinchers in this illustrated embodiment) configured to receive a user input thereto to control movement of the arm 400 and configured to be freely moved around by the user U (e.g., handheld and moved around any space in or near an operating room, etc.), an additional arms 422 that can be configured and used similar to the arm 400, and a control system 426 configured to facilitate control of the arms 400, 422 by translating user inputs to the user input devices 412, 418, e.g., manual movement of a user input device, movement indicated by touch on a touch screen, etc., to one or both of the arms 400, 422 as appropriate. The system 406 in this illustrated embodiment includes two arms 400, 422, but it can include another number of arms, e.g., three, four, etc. The at least one display 410 of the user interface sub-system 408 can be configured as a user input device, e.g., as a touchscreen configured to receive user touch input thereon. The user interface sub-system 408 can be in the same room as the patient P, or it can be in a different room.

The control system 426 can, as in this illustrated embodiment, include at least one computer 428, one or more cables 430, and at least one power supply 432. The computer 428 can include at least one processor (not shown). As mentioned above, at least some embodiments of control systems can be at least partially wireless, in which case at least some of the cables 430 need not be present. The robotic surgical system 406 can include at least one foot pedal 434 coupled to the computer 428 via one of the cables 430, which can allow the foot pedal 434 to serve as a user input device. The robotic surgical system 406 can include at least one knee control (not shown) coupled to the computer 428 via one of the cables 430, similar to a knee control of a sewing machine, which can allow the knee control to serve as a user input device.

The robotic surgical system 406 can include a frame 424 for each of the arms 400, 422. The frames 424 in this illustrated embodiment are each mounted to a surgical table 426, but as mentioned above, frames can be mounted elsewhere. The frame 424 in this illustrated embodiment includes a vertical extension movably coupled to a rail mounted to the table 426. The vertical extension can be configured to move along the rail, thereby facilitating positioning of the arms 400, 422 relative to the patient P.

One or more manually operated surgical instruments 420, e.g., instruments not under the control of the robotic surgical system 406, can be used to perform the surgical procedure being performed on the patient P.

Aspects of the robotic surgical system 406 are further described in previously mentioned Intl. Pat. Pub. No. WO2014151621 filed Mar. 13, 2014 entitled "Hyperdexterous Surgical System."

Figure 9:
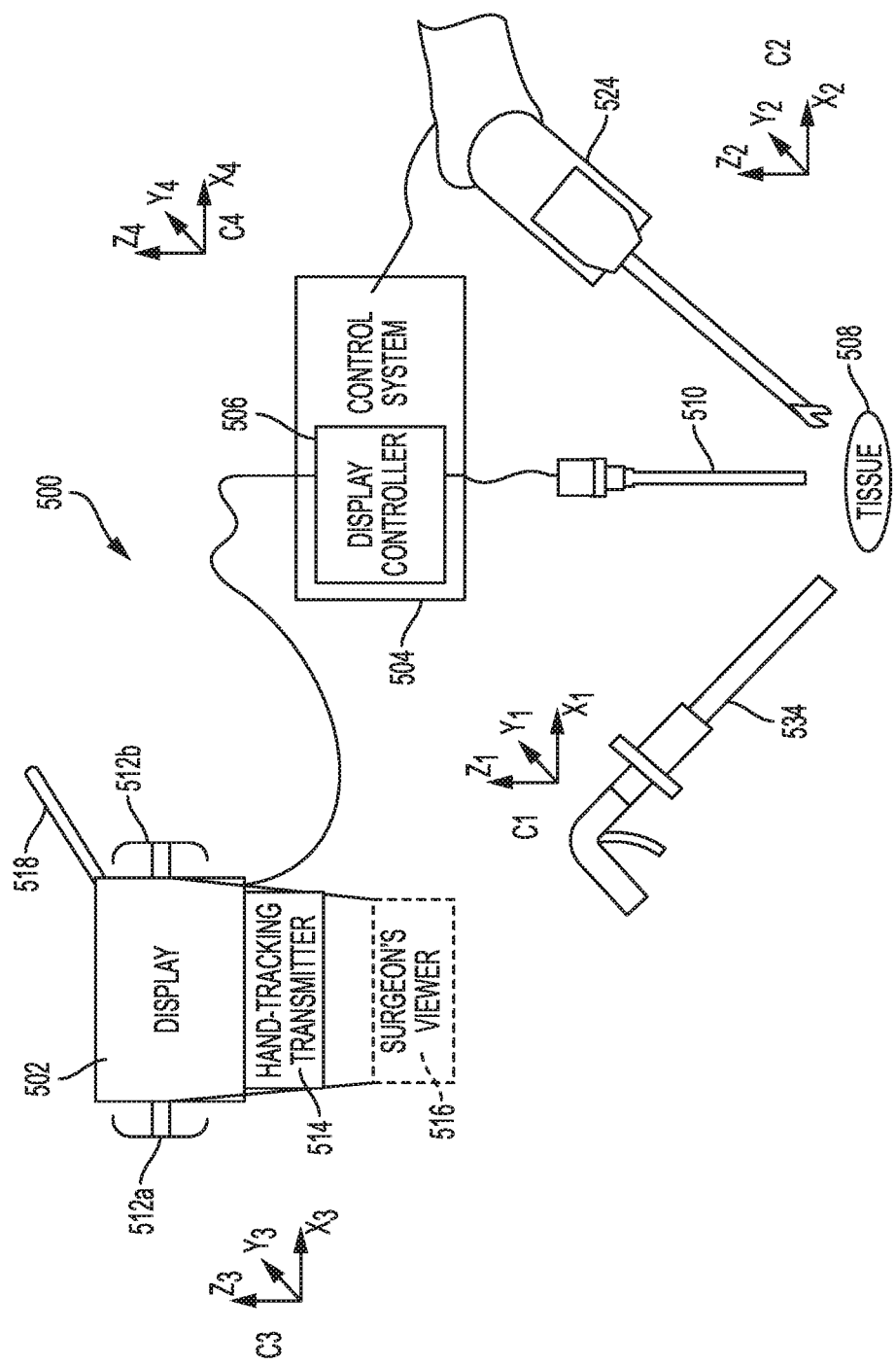
FIG. 9 is a schematic and perspective view of another embodiment of a robotic surgical system.

FIG. 9 illustrates another embodiment of a robotic surgical system 500. As in this illustrated embodiment, the robotic surgical system 500 can include a display 502 and a control system 504 configured to be in electronic communication with the display 502. The display 502 and the control system 504 are in wired electronic communication in this illustrated embodiment, but the electronic communication can be wireless. The control system 504 can include a computer system including a display controller 506 configured to facilitate the display of images on the display 502, such as images of tissue 508 visualized by an endoscope 510 coupled to the control system 504. The display 502 can be coupled to handles 512a, 512b configured to facilitate manual movement of the display 502, a hand-tracking transmitter 514 configured to generate a field (e.g., an electromagnetic field, an optical field (e.g., light beams), etc.), a surgeon's viewer 516 (e.g., glasses, etc.) configured to facilitate three-dimensional (3-D) viewing of 3-D images shown on the display 502, and a boom 518 configured to mount the display 502 to a stable surface (e.g., a wall, a table, etc.). The display 502 can be configured to show two-dimensional (2-D) and/or 3-D images.

Figure 10:
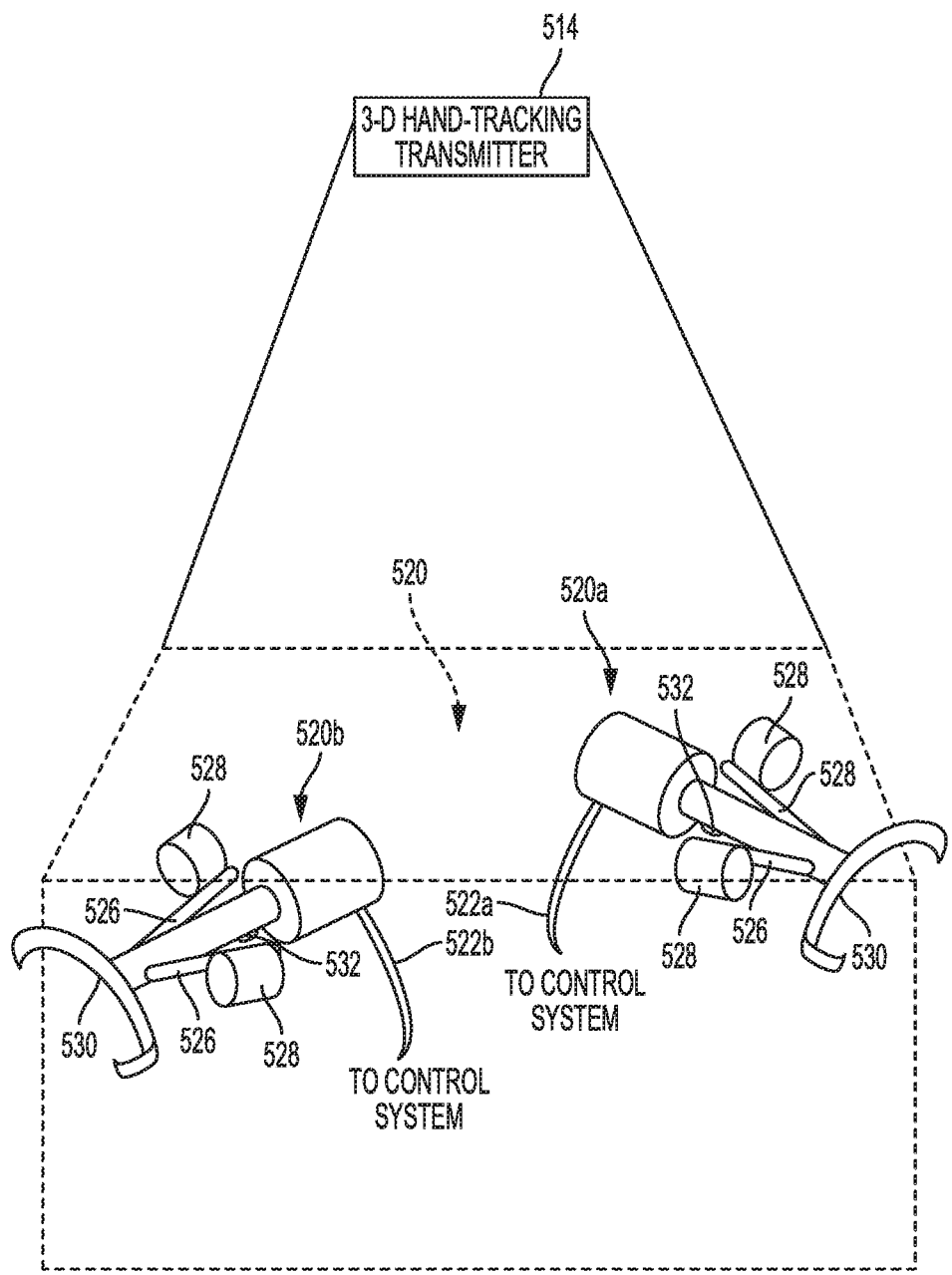
FIG. 10 is a perspective view of one embodiment of a master tool in a field generated by a transmitter of the robotic surgical system of FIG. 9.

Movement of a user-controlled master tool (also referred to herein as a master input device) 520, an embodiment of which is illustrated in FIG. 10, in the field generated by the transmitter 514 can be configured to provide sensed spatial position and orientation information in a 3-D coordinate system. The master tool 520 can be configured to transmit the spatial position and orientation information to the control system 504, such as by cables 522a, 522b. The control system 504, e.g., a processor thereof, can be configured to receive the transmitted spatial position and orientation information and, in response thereto, cause a slave tool 524 to move in accordance with the user's movement of the master tool 520. The robotic surgical system 500 can thus allow control of the slave tool 524 via the master tool 520. The master tool 520 in this illustrated embodiment includes first and second master tool grips 520a, 520b that each include a plurality of levers 526, a plurality of finger loops 528, a palm rest 530, and a mode control button 532, but the master tool 520 can have a variety of other configurations, as will be appreciated by a person skilled in the art. The robotic surgical system 500 can include any number of master tools and any number of slave tools each configured to be controlled by the master tool(s).

One or more manually operated surgical instruments 534 can be used to manipulate the tissue 508 in addition to the slave tool 524 that can manipulate the tissue 508.

FIG. 9 illustrates first, second, third, and fourth coordinate systems C1, C2, C3, C4 representing local coordinates that specify the respective position and orientation of the portion of the system 500 with which they are associated. The first coordinate system C1 is associated with the manually operated surgical instrument 534. The second coordinate system C2 is associated with the slave tool 524. The third coordinate system C3 is associated with a user (not shown) visualizing the display 502, and hence also with the master input device 520 configured to be manipulated by the user. The fourth coordinate system C4 is associated with the control system 506, and hence also with images that the control system 506 causes to be displayed on the display 502. In general, the control system 506 can be configured to map and translate the third coordinate system C3 into the second coordinate system C2, e.g., map and translate movement of the master tool 520 to movement of the slave tool 524. For example, if the user is holding the master input device 520, e.g., one of the first and second master tool grips 520a, 520b, in one of his/her hands and moves that hand to his/her right, thereby moving the held master input device 520 to the right, the control system 506 can be configured to correspondingly cause a working end of the slave tool 524 to move to the right. This movement can be accomplished by the control system 506 causing an arm to which the slave tool 524 is coupled, similar to the arms discussed herein, to move. This movement of the slave tool 523 can "correct" for pivoting of a trocar (not shown) through which the slave tool 524 may be inserted to access the tissue 508.

Aspects of the robotic surgical system 500 are further described in previously mentioned U.S. Pat. No. 8,831,782 filed Jul. 15, 2013 entitled "Patient-Side Surgeon Interface For A Teleoperated Surgical Instrument."

Figure 11:
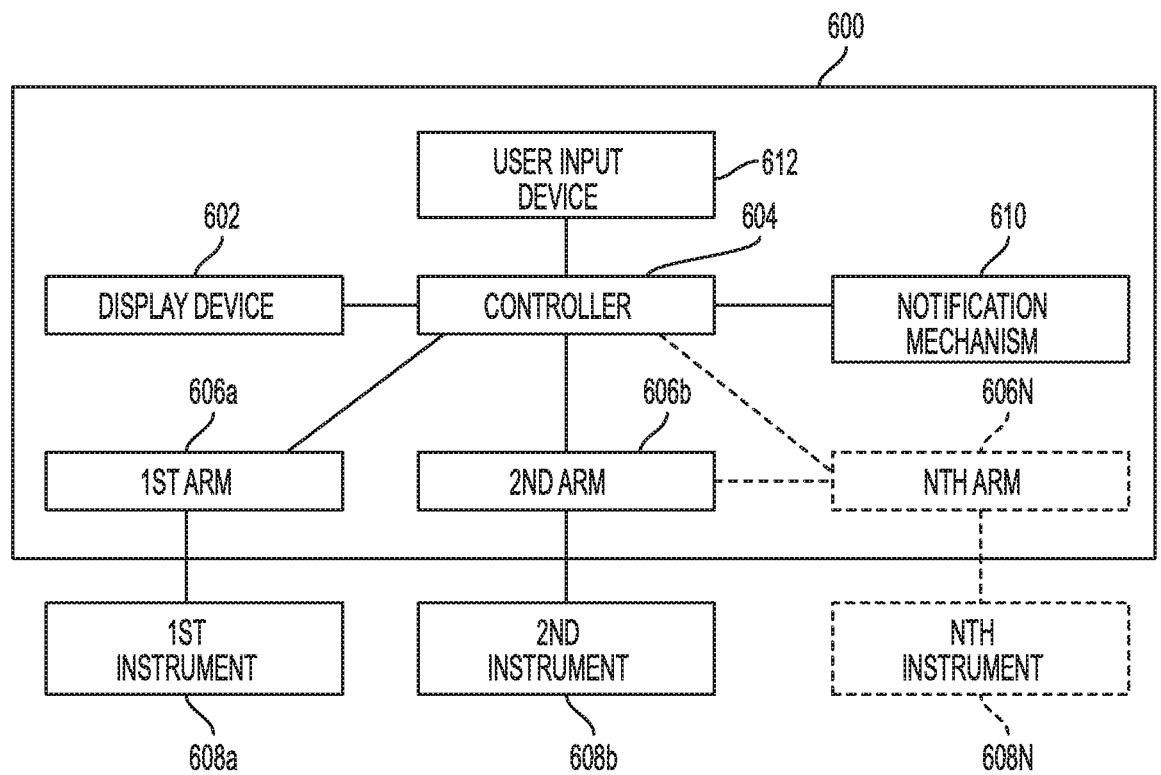
FIG. 11 is a schematic view of another embodiment of a robotic surgical system having a plurality of surgical instruments coupled thereto.

As mentioned above, at least some of the methods, systems, and devices for controlling movement of a robotic surgical system provided herein can be configured to facilitate movement of a surgical instrument into a field of view of a camera visualizing a surgical area. FIG. 11 illustrates one embodiment of such a robotic surgical system 600. The robotic surgical system 600 can generally be configured and used similar to the robotic surgical system 200 of FIG. 3. The robotic surgical system 600 can include a computer system that includes a display device 602, a controller 604, a plurality of movement mechanisms 606a, 606b, 606N, and a notification mechanism 610 (e.g., an IO interface such as a display, a speaker, a light, etc.). In at least some embodiments, the notification mechanism 610 can be omitted, and the robotic surgical system 600 can be configured to provide notifications using another element thereof, as discussed further below. As in this illustrated embodiment, the movement mechanisms 606a, 606b, 606N can each include an electromechanical arm. The robotic surgical system 600 can include at least two movement mechanisms 606a, 606b and, optionally, an additional one or more movement mechanisms for a total of "N" movement mechanisms, where N is greater than or equal to three. Each of the movement mechanisms 606a, 606b, 606N can be configured to couple to one of a plurality of surgical instruments 608a, 608b, 608N, as discussed herein. The controller 604 can be configured to receive an input from a user (not shown) requesting movement, relative to a patient (not shown), of a master one of the surgical instruments 608a, 608b, 608N. The user can provide the input using a user input device 612 (e.g., a master tool), as discussed herein. The controller 604 can be configured to cause motors (not shown) of the robotic surgical system 600 to drive movement of the movement mechanisms 606a, 606b, 606N, as also discussed herein, thereby causing movement of the surgical instruments 608a, 608b, 608N respectively coupled thereto.

In an exemplary embodiment, at least one of the surgical instruments 608a, 608b, 608N can include a camera having a field of view and configured to visualize a surgical area such that the robotic surgical system 600 can be coupled to at least one camera. To facilitate discussion herein, the first surgical instrument 608a in this illustrated embodiment is presumed to include a camera.

Figure 12:
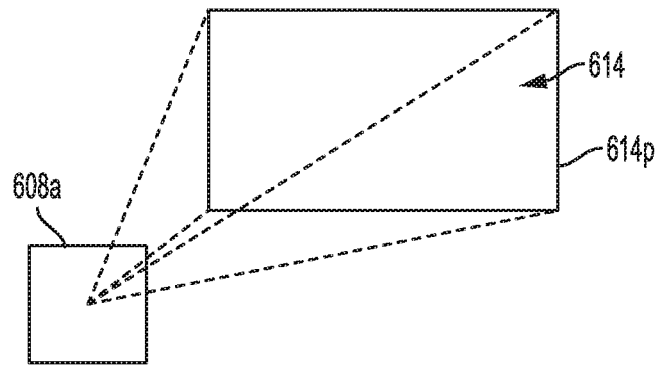
FIG. 12 is a schematic view of a field of view of a camera.

As will be appreciated by a person skilled in the art, as illustrated for example in FIG. 12, a camera (e.g., the first surgical instrument 608a) can define a field of view 614. The field of view 614 can include an area configured to be visible by the camera 608a at any given time as prescribed by the camera's configuration, e.g., by a configuration of a lens of the camera 608a and by a configuration of an image sensor of the camera 608a. The area can be 2-D, or the area can be 3-D such that the area is a volume. As will be appreciated by a person skilled in the art, a camera may only show where something is along a line, with depth or distance being inferred.

The field of view 614 can be defined by a perimeter 614p such that the area visualized by the camera 608a includes an area bounded by the perimeter 614p, with the camera 608a being unable to visualize the area outside the perimeter 614p. A specific size and shape of the perimeter 614p can depend on the camera's configuration. As the camera moves, the specific area of a target being visualized can change as the perimeter 614p surrounds different portions of the target.

For example, different portions of a surgical area can be visualized within the perimeter 614p as the camera 608a moves relative to the surgical area or as the surgical area moves relative to the camera 608a.

The display device 602 can be configured to display an image thereon (which can be a 2-D image or a 3-D image) corresponding to the area visualized by the camera 608a. The image can, as will be appreciated by a person skilled in the art, be an exact image of the visualized area or be a modified image of the visualized area, e.g., be a two-dimensional representation of a three-dimensional area, be black and white instead of color, have reference marks superimposed thereon, etc.

The robotic surgical system 600 can be configured to signal the user of the robotic surgical system 600 with a cue regarding a location of a one of the surgical instruments 608b, 608N relative to the field of view 614 of the camera 608a. The cue can be configured to help the user position the one of the surgical instruments 608b, 608N within the field of view 614 such that the one of the surgical instruments 608b, 608N can be visualized by the user, e.g., in an image on the display device 602. The controller 604 can be configured to extract a volumetric or surface model from the area within the field of view's perimeter 614p as visualized by the camera 608a, which can be used by the controller 604 in providing the cue via the notification mechanism 610.

The cue can have a variety of configurations. The cue can include any one or more of an audible signal, a visual signal, and a tactile signal. Examples of an audible signal include a buzzing sound, a series of beeps, a speaking computerized voice, etc. Examples of a visual signal include a constantly illuminated light, a blinking light, an icon shown on the display device 602 and/or on another display device, text shown on the display device 602 and/or on another display device, etc. Examples of a tactile signal include a vibration (such as of a portion of the robotic surgical system 600, e.g., a vibration of the user input device 612, etc.), a temperature change (such as heating or cooling of a portion of the robotic surgical system 600, e.g., a temperature change of at least a portion of the user input device 612, etc.), etc. Providing more than one type of cue, e.g., an auditory signal and a visual signal, a tactile signal and an audible signal, etc. may help ensure that the user receives the cue. For example, providing an audible signal with at least one other type of signal may help ensure that the user receives the cue if the user is being subjected to other noise (e.g., instrument motors, talking medical personnel, etc.) that may drown out the audible signal. For another example, providing a visual signal with at least one other type of signal may help ensure that the user receives the cue if the visual signal is provided outside the user's current line of sight. For yet another example, providing a color-based visual signal with at least one other type of signal may help ensure that a colorblind user who may have difficulty with the visual signal receives at least one of a non-color dependent audible signal and non-color dependent tactile signal.

The controller 604 can be configured to cause the notification mechanism 610 to provide the cue, e.g., by transmitting a signal thereto. In at least some embodiments, the notification mechanism 610 can include a plurality of notification mechanisms with each one of the notification mechanisms being coupled to one of the arms 608a, 608b, 608N, such as each of the arms 608a, 608b, 608N having a light mounted thereon, etc. As mentioned above, in embodiments in which the notification mechanism 610 is omitted, another portion of the robotic surgical system 600 can be configured to provide the cue, such as the display device 602 being configured to display the cue thereon.

The controller 604 can be configured to cause the notification mechanism 610 to constantly provide the cue, e.g., constantly illuminate a light, constantly display a visible icon, text, etc. on the display device 602, constantly sound an audible signal, etc., as long as the one of the surgical instruments 608b, 608N whose location relative to the field of view 614 is at issue is not located within the field of view 614. The constant providing of the cue can include the cue being configured in its normal state to repeatedly turn on and off, such as in the case of a blinking light or a series of audible beeps. The controller 604 can be configured to stop providing the cue when the one of the surgical instruments 608b, 608N whose location relative to the field of view 614 is at issue is located at least partially within the field of view 614. Constant provision of the cue may thus help the user controlling movement of the one of the surgical instruments 608b, 608N whose location relative to the field of view 614 is at issue, e.g., the user handling the user input device 612, to determine when that surgical instrument has entered the field of view 614 because the cue has stopped.

The cue can be configured to indicate to the user whether the current movement of the surgical instrument at issue will cause the instrument to enter the field of view 614. The controller 604 can be configured to change the cue during provision of the cue, thereby providing the information to the user regarding whether the instrument's current movement will cause the instrument to enter the field of view 614. The change in the cue may facilitate the user's determination of how, or whether, to continue the instrument's movement, e.g., in continuing to manipulate and provide input to the user input device 612. In the case of an audible signal, the cue can change in one or more ways including, e.g., changing an amplitude of the sound, changing a pitch of the sound, changing a loudness of the sound, changing a modulation of the sound, changing a chord (major versus minor), using binaural displacement, providing tones more or less frequently, etc. In the case of a visual signal, the cue can change in one or more ways including, e.g., changing physical location of the visual cue on the display screen on which it is displayed, changing color, changing brightness, changing hue, changing saturation, using temporal modulation, blinking a light more or less frequently, etc. In the case of a tactile signal, the cue can change in one or more ways including, e.g., changing vibration strength, becoming colder, becoming hotter, etc.

A first type of change in the cue can indicate that the instrument's current movement is moving the instrument toward being in the field of view 614, and a second type of change in the cue can indicate that the instrument's current movement is moving the instrument away from being in the field of view 614. For example, for an audible signal, the first type can include the sound becoming quieter and the second type can include the sound becoming louder. For another example, for an audible signal, the first type can include beeps being sounded more frequently (e.g., with less "dead" space between the beeps) and the second type can include beeps being sounded less frequently (e.g., with more "dead" space between the beeps). For yet another example, for an audible signal, the first type can include a higher pitched sound and the second type can include a lower pitched sound. For another example, for a visual signal, the first type can include the cue becoming brighter in color and the second type can include the cue becoming duller in color. For still another example, for a visual signal, the first type can include a light blinking faster and the second type can include the light blinking slower. For another example, for a visual signal, the first type can include a light transitioning toward one color and the second type can include the light transitioning toward another color. For yet another example, for a tactile signal, the first type can include a faster vibration and the second type can include a slower vibration. For another example, for a tactile signal, the first type can include cooling and the second type can include heating. For yet another example, for a tactile signal, the first type can include a temperature change toward an ambient temperature and the second type can include a decrease in temperature.

The change can represent a single parameter or a plurality of parameters. One example of the single parameter includes a simple better/worse signal with the first type of change indicating that the instrument's current movement is moving the instrument toward being in the field of view 614 ("better") and a second type of change indicating that the instrument's current movement is moving the instrument away from being in the field of view 614 ("worse"). The change in the cue indicating the better/worse parameter may facilitate the user guiding the instrument in a way to achieve the "better" cue. Another example of the single parameter includes an indication as to whether a current direction of the instrument is leading the instrument toward being in the field of view 614 or is moving the instrument away from being in the field of view 614. In other words, the cue can be configured to indicate to the user whether the instrument's current bearing should be adjusted in order to better aim the instrument toward the field of view 614. Another example of the single parameter includes an indication as to how much distance remains between the surgical instrument and the field of view 614. The change in the cue indicating the direction parameter may facilitate user decision-making in controlling movement of the instrument, such as the user deciding to move the instrument slower as the instrument approaches the field of view 614, the user deciding to make more radical trajectory adjustments of the instrument the farther the instrument is from entering the field of view 614, etc. The change representing a plurality of parameters can include multiple ones of the single parameters, e.g., better/worse and direction; better/worse, direction, and remaining distance; etc.

Figure 13:
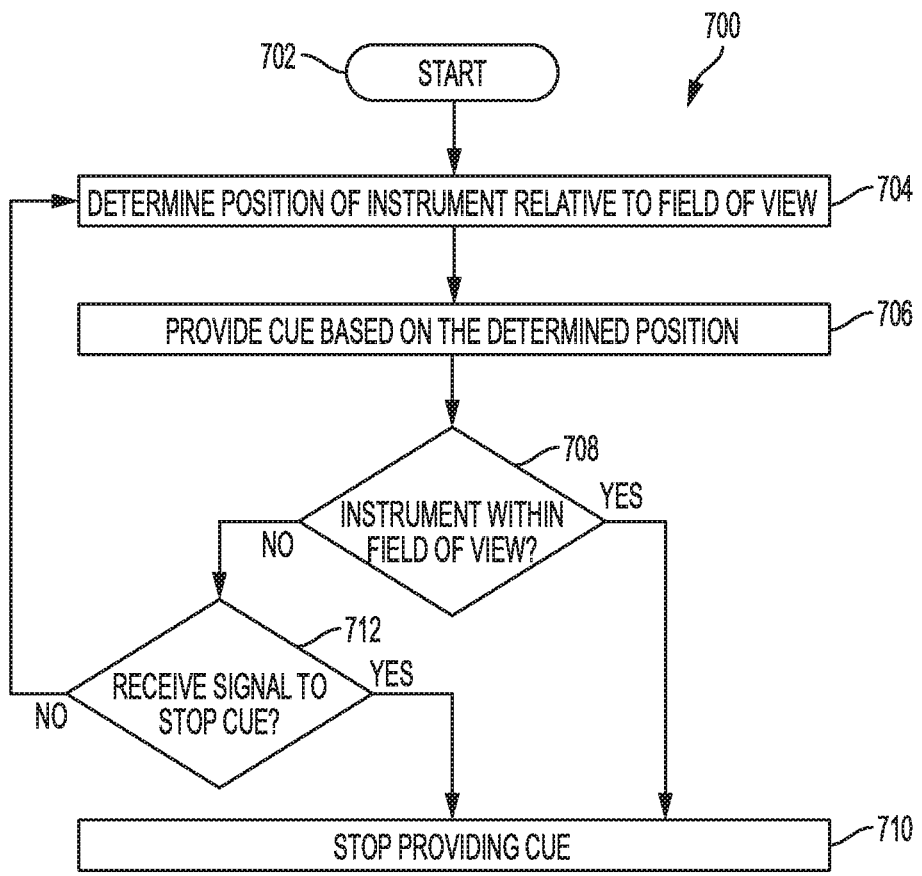
FIG. 13 is a flowchart of one embodiment of a process of providing a cue.

FIG. 13 illustrates one embodiment of a process 700 of the controller 604 providing a cue based on a location of one of the instruments 608b, 608N relative to the field of view 614, e.g., based on the direction and distance from the one of the instruments 608b, 608N (such as an end effector thereof) to the nearest point on the field of view 614, whether the field of view 614 be 2-D or 3-D. For ease of discussion of FIG. 13, the second instrument 608b is considered to be the instrument at issue. The process 700 can start 702 in any of a variety of ways. One example of the start 702 includes the user providing an input to the robotic surgical system 600 indicating that the user desires to track the location of the second instrument 608b relative to the field of view 614, e.g., the user input device 612 can include a tracking control mechanism (not shown), e.g., a button, lever, etc., configured to be manipulated by the user similar to the mode control button discussed herein; the display device 602 can be configured to receive a touch input thereto; an IO interface (not shown), such as a keyboard, coupled to the controller 604 can be configured to receive user input thereto; etc. The start 702 can thus be on-demand. Another example of the start 702 includes when the second surgical instrument 608b moves from being within the field of view 614 to outside the field of view 614. The start 702 can thus be automatic. Yet another example of the start 702 includes the second surgical instrument 608b being advanced into a trocar (not shown) through which the second surgical instrument 608b gains access to a patient's body, which is also an example of the start 702 being automatic.

After the start 702 of the process 700, the controller 604 can be configured to determine 704 a current position of the surgical instrument 608b at issue relative to the field of view 614. The current position can be determined in a variety of ways. For example, the position of the instrument 608b can be based on a trajectory of the instrument 608b as defined by a longitudinal axis of the instrument 608b, e.g., a longitudinal axis of an elongate shaft of the instrument 608b, etc., since the instrument's longitudinal axis can indicate a direction of the instrument's movement. For another example, the position of the instrument 608b can be based on a trajectory of the instrument 608b as defined by a longitudinal axis of a trocar through which the instrument 608b is being advanced, since the instrument's movement can be limited by the trocar, e.g., by a cannulated elongate portion of the trocar through which the instrument 608b is being advanced. For yet another example, the position of the instrument 608b can be based on a position of the second arm 606b to which the second surgical instrument 608b is coupled, since the instrument's movement is controlled via the second arm 606b. The controller 604 can be configured to provide 706 a cue based on the determined current position.

The process 700 can be iterative as long as the surgical instrument 608b is not within the field of view 614. After providing the cue, the controller 604 can be configured to determine 708 whether the instrument 608b is within the field of view 608b, e.g., by analyzing the camera image of the field of view 614, by comparing a coordinate of the instrument's current position with a coordinate map corresponding to the field of view 614, etc. If the instrument 608b is determined 708 to be within the field of view 614, the controller 604 can be configured to stop 710 providing the cue. If the instrument 608b is determined 708 to not be within the field of view 614, the controller 604 can be configured to continue providing the cue unless the controller 604 receives 712 a signal to stop providing 706 the cue. The signal to stop 710 providing the cue can be input by the user similar to the user being able to start 702 the process 700. The user may want to stop the cue if, for example, the instrument 608b will be remaining in its current position while others of the instruments 608a, 608N are manipulated and/or while other aspects of the surgical procedure are being performed. If a signal to stop providing 706 the cue is not received 712, then the controller 704 can be configured to again determine 704 a current position of the instrument 608b relative to the field of view 614 and continue providing 706 the cue, with the cue being changed as needed based on the most recently determined 704 current position of the instrument 608b.

Figure 14:
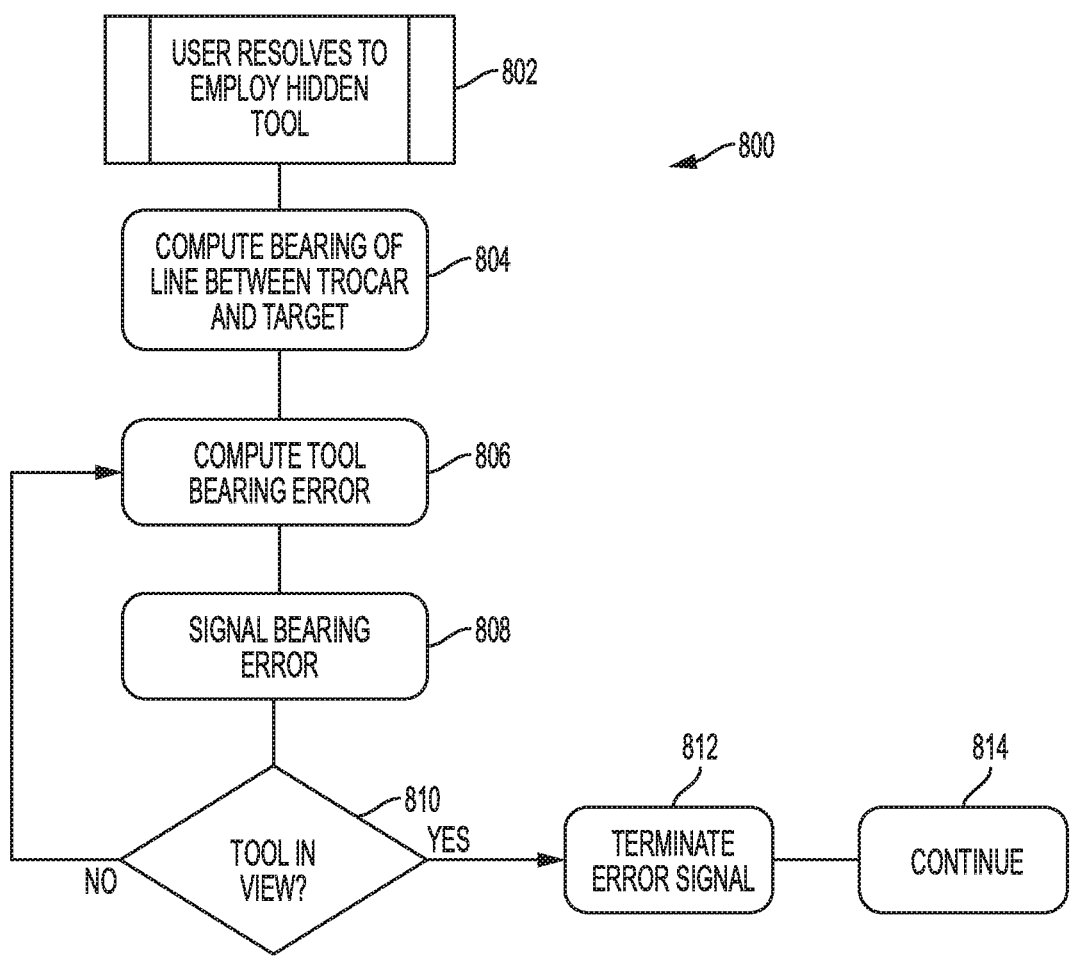
FIG. 14 is a flowchart of another embodiment of a process of providing a cue.

FIG. 14 illustrates another embodiment of a process 800 of the controller 604 providing a cue based on a location of one of the instruments 608b, 608N relative to the field of view 614. The process 800 of FIG. 14 generally corresponds to the process 700 of FIG. 13. In the illustrated embodiment of FIG. 14, the process 800 involves advancement of the instrument 608b at issue through a trocar. The process 800 of FIG. 14 can start 802 by the user deciding to employ a hidden one of the surgical instruments 608b, 608N, which for ease of discussion of FIG. 14, will be considered to be the second surgical instrument 608b. The user can signal this decision to the controller 604 in any of a variety of ways, e.g., actuating the tracking control mechanism, inserting the instrument 608b into a trocar, etc. The controller 604 can be configured to compute 804 a bearing of a line between the trocar and the target, e.g., the field of view 614. The line can include a trajectory line of the trocar, which can, as discussed herein, be defined by a longitudinal axis of the trocar. The computing 804 can include calculating a direction of a line between a pivot point (e.g., virtual center, insertion point, etc.) of the trocar and a reference point in the field of view 614. The line may, but usually will not coincide with the longitudinal axis of the trocar until the user makes it so by providing an input to the system. The controller 604 can be configured to compute 806 a tool bearing error indicative of the instrument's current offset from intersection with the field of view 614, e.g., a current offset of the bearing of the line from the field of view 614 as defined by its perimeter 614p. For example, the tool bearing error can be based on an angular offset of the bearing of the line from a centerpoint of the field of view 614 as defined by the perimeter 614p. In embodiments in which the bearing of the line is determined based on a trajectory line of the instrument 608b as defined by a longitudinal axis of the instrument 608b, the tool bearing error can be similarly computed. For another example, the tool bearing error can be based on an angular offset of the bearing of the line from a centerpoint of a line joining a pair of instrument working ends visible within the field of view 614. For yet another example, the tool bearing error can be based on an angular offset of the bearing of the line from a point along the camera's trajectory that is nearest to a working end of any surgical instrument present within the field of view 614. For yet another example, the tool bearing error can be based on an angular offset of the bearing of the line from a first intersection of the line with a surface within the field of view 614.

The controller 604 can be configured to signal 808 the computed bearing error by providing a cue. If the movement of the instrument 608b has moved the instrument to be in the field of view 614, e.g., if the controller 604 determines 810 that the instrument 608b is within the field of view 614, then the controller 604 can be configured to terminate 812 the provided signal. The surgical procedure can then continue 814. If the movement of the instrument 608b has not moved the instrument to be in the field of view 614, then the controller 604 can be configured to again compute 806 the tool bearing error and again signal 808 the computed bearing error, with the cue being changed if needed based on the re-computed tool bearing error. The process 800 can thus be iterative.

Figure 15:
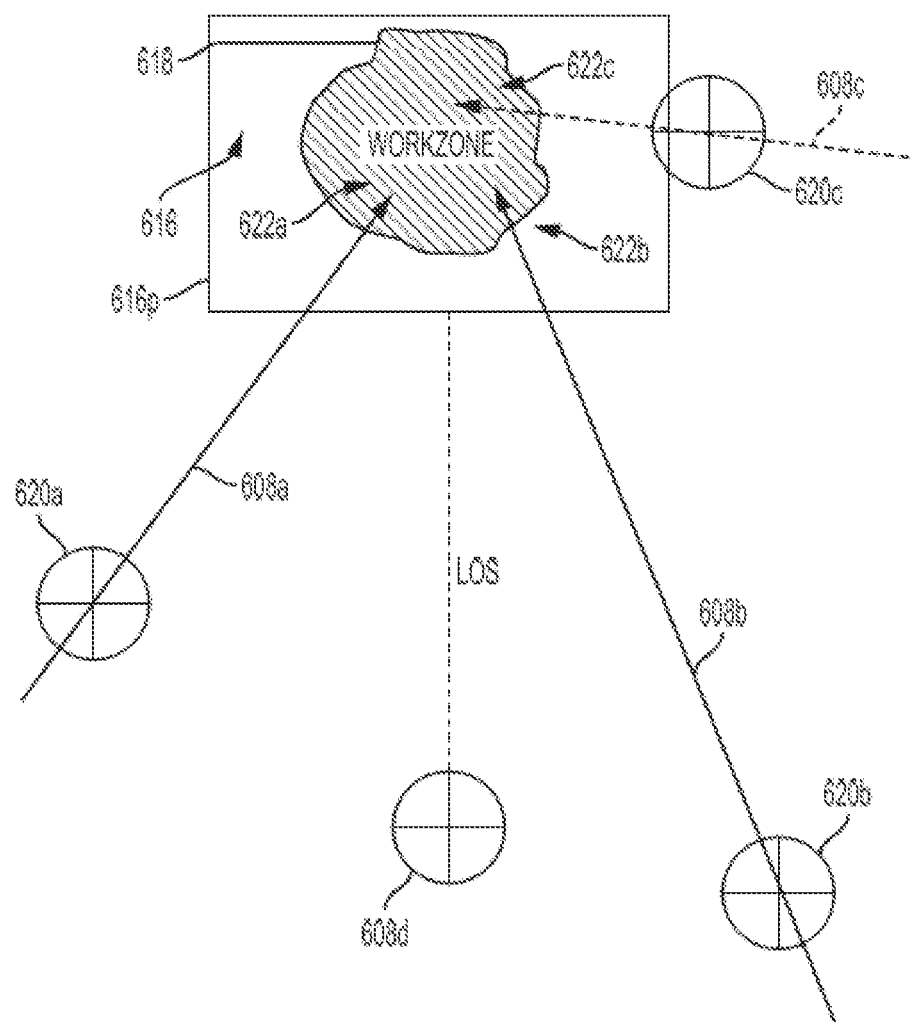
FIG. 15 is a schematic view of one embodiment of use of the robotic surgical system and the plurality of surgical instruments of FIG. 11.
Figure 16:
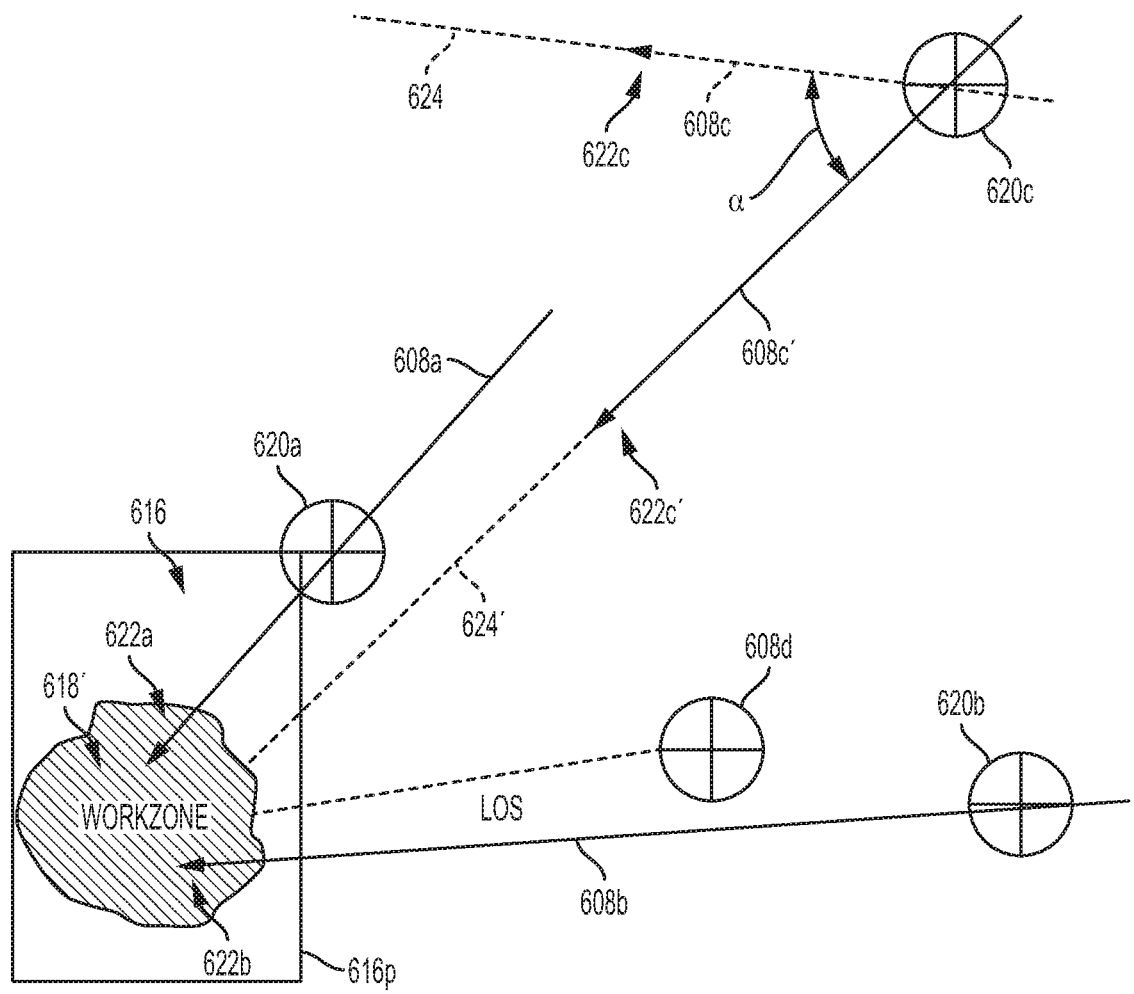
FIG. 16 is a schematic view of the use of the robotic surgical system and the plurality of surgical instruments of FIG. 15 at a time subsequent to a time of FIG. 15.
Figure 17:
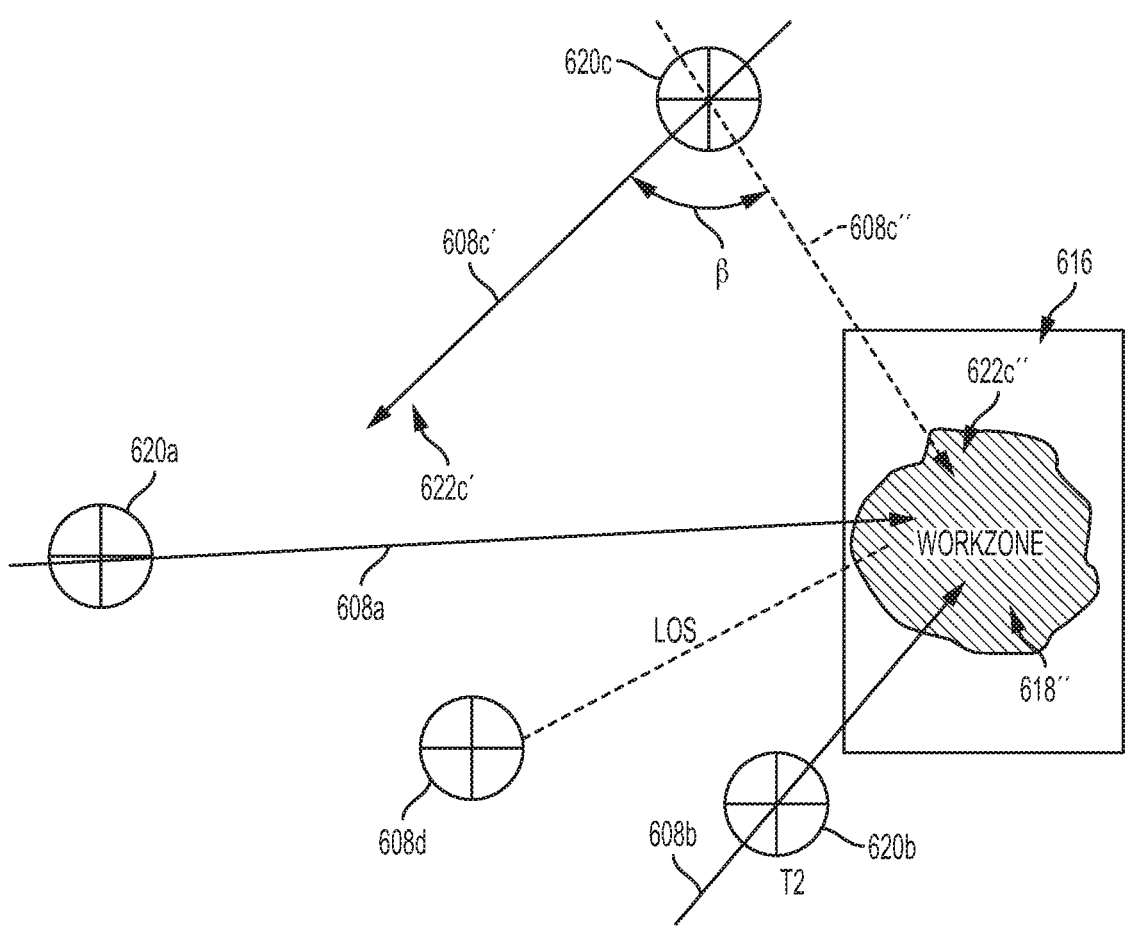
FIG. 17 is a schematic view of the use of the robotic surgical system and the plurality of surgical instruments of FIG. 16 at a time subsequent to a time of FIG. 16.

FIGS. 15-17 illustrate one embodiment of a performance of a surgical procedure in which a robotic surgical system can be configured to provide a cue based on a location of a surgical instrument relative to a field of view of a camera. The performance of the surgical procedure is described with respect to the robotic surgical system 600 of FIG. 11, but this and other embodiments of performing a surgical procedure can be performed using other robotic surgical systems described herein. The surgical procedure can begin by preparing the patient for surgery and making one or more appropriately sized incisions at a desired location, as will be appreciated by a person skilled in the art. The surgical procedure can, as in this illustrated embodiment, include a minimally invasive procedure in which one or more access devices, trocars in this illustrated embodiment, can be positioned in any one or more of the incision(s) to provide access to the surgical site. In other embodiments, the surgical procedure can be an open procedure.

To facilitate discussion herein of this illustrated embodiment in FIGS. 15-17, the plurality of surgical instruments coupled to the robotic surgical system 600 via the "N" number of arms is presumed to include four surgical instruments, with a fourth one of the surgical instruments 608d being presumed to include a camera. The robotic surgical system 600 is accordingly presumed for purposes of discussing this illustrated embodiment to include at least four arms, with each of the plurality of surgical instruments 608a, 608b, 608c, 608d being coupled to one of the arms. The camera 608d can have a line of sight (LOS), e.g., a central axis of a 3-D field of view, and can define a field of view 616. FIGS. 15-17 illustrate the surgical instruments 608a, 608b, 608c, 608d relative to an insufflated patient of substantial curvature, convex out of the page.

Once the patient is prepared for surgery, each of the plurality of surgical instruments 608a, 608b, 608c, 608d can be positioned relative to a patient in any of a variety of ways, as will be appreciated by a person skilled in the art. As shown in FIG. 15, the camera 608d can be positioned such that its field of view 616 surrounds a target surgical area 618, also referred to herein as a workzone. In other words, the workzone 618 can be contained with the field of view's perimeter 616p. As also shown in FIG. 15, the first surgical instrument 608a can be advanced through a first trocar 620a inserted into the patient such that a distal end 622a of the first surgical instrument 608a (e.g., a working end of the first surgical instrument 608a) is located at a desired location, such as within the workzone 618 as in this illustrated embodiment, the second surgical instrument 608b can be advanced through a second trocar 620b inserted into the patient such that a distal end 622b of the second surgical instrument 608b (e.g., a working end of the second surgical instrument 608b) is located at a desired location, such as within the workzone 618 as in this illustrated embodiment, and the third surgical instrument 608c can be advanced through a third trocar 620c inserted into the patient such that a distal end 622c of the third surgical instrument 608c (e.g., a working end of the third surgical instrument 608c) is located at a desired location, such as within the workzone 618 as in this illustrated embodiment.

FIG. 16 illustrates the surgical procedure at a time subsequent to the time of FIG. 15. In FIG. 16, surgical attention has shifted downward and to the left as reflected by the workzone 618' being shifted in position downward and to the left of the workzone 618 of FIG. 15. The locations through which the surgical instruments 608a, 608b, 608c, 608d have been inserted into the patient, e.g., incisions through which the instruments have been directly inserted (as with the camera 608d) or trocars 620a, 620b, 620c positioned in incisions and through which the instruments have been inserted (as with the first, second, and third instruments 608a, 608b, 608c), remain the same as in FIG. 15. The camera 608d has been angularly adjusted in position such that its field of view 616 surrounds the shifted workzone 618', and the first and second instruments 608a, 608b have been angularly adjusted within their respective trocars 620a, 620b such that their respective distal ends 622a, 622b are positioned to desired locations within the shifted workzone 618'. The third surgical instrument 608c, shown by the dotted line in FIG. 16, is at the same position as in FIG. 15 with its distal end 622c located outside the camera's field of view 616.

The third surgical instrument 608c can be angularly adjusted at an angle α such that the surgical instrument 608c', represented by a solid line in FIG. 16, is directed toward the field of view 616. As the third surgical instrument 608c is moved from its position in FIG. 15 in response to a user's input to the user input device 612, the controller 604 can be configured to cause the notification mechanism 610 to provide a cue to the user indicative of the third surgical instrument's location relative to the field of view 616 in its shifted position shown in FIG. 16. As discussed herein, the controller 604 can be signaled to begin providing the cue by the user providing an input to the robotic surgical system 600 indicating that the user desires to track the location of the third instrument 608c relative to the field of view 616, or the controller 604 be configured to automatically begin providing the cue in response to the third surgical instrument 608c be adjusted in position by the user. As also discussed herein, the controller 604 can be configured to provide the cue based on a trajectory 624 of the third surgical instrument 608c moving toward an adjusted trajectory 624' that aligns the third surgical instrument 608c to intersect with the field of view 616 and the shifted workzone 618'. The third instrument's trajectory in this illustrated embodiment is based on a longitudinal axis of the third trocar 620c through which the instrument 608c is advanced, although as mentioned herein, the trajectory can be based on a longitudinal axis of the third surgical instrument 608c. The controller 604 can thus provide the cue to the user in real time with the third surgical instrument's movement from its initial trajectory 624 so as to facilitate positioning of the third surgical instrument 608c at the adjusted trajectory 624' along which the third surgical instrument 608c can be advanced to enter the camera's field of view 616 and hence be able to be visualized by the user. For example, in beginning to move the third surgical instrument 608d from its position in FIG. 15, the user can cause the third surgical instrument 608d to move with a quick circular motion, which can help the user quickly discover the adjusted trajectory 624' based on the changing cue during the circular motion. The user can then more slowly move the third surgical instrument 608c to more finely find the adjusted trajectory 624' and move the third surgical instrument 608c therealong to move the third surgical instrument's distal end 622c' in to view within the field of view 616. For another example, the user can slowly move the third surgical instrument 608c from its position in FIG. 15 in a side-to-side sweeping motion to help locate the adjusted trajectory 624'.

Once the distal end 622c' of the third surgical instrument 608c enters the field of view 616, the controller 604 can be configured to stop the cue, as discussed herein.

FIG. 17 illustrates the surgical procedure at a time subsequent to the time of FIG. 16. In FIG. 17, the workzone 618" has shifted in position upward and to the right of the workzone 618' of FIG. 16. The locations through which the surgical instruments 608a, 608b, 608c, 608d have been inserted into the patient remain the same as in FIGS. 15 and 16. The camera 608d has been angularly adjusted in position such that its field of view 616 surrounds the second shifted workzone 618", and the first and second instruments 608a, 608b have been angularly adjusted within their respective trocars 620a, 620b such that their respective distal ends 622a, 622b are positioned to desired locations within the second shifted workzone 618". The third surgical instrument 608c, shown by the solid line in FIG. 17, is at the same position as in FIG. 16 with its distal end 622c' located outside the camera's field of view 616. The third surgical instrument 608c can be angularly adjusted at an angle β such that the surgical instrument 608c", represented by a dotted line in FIG. 17, is directed toward the field of view 616. Similar to that discussed above regarding claim 16, as the third surgical instrument 608c is moved from its position in FIG. 16 in response to a user's input to the user input device 612, the controller 604 can be configured to cause the notification mechanism 610 to provide a cue to the user indicative of the third surgical instrument's location relative to the field of view 616 in its shifted position shown in FIG. 17. Once the distal end 622c" of the third surgical instrument 608c enters the field of view 616, the controller 604 can be configured to stop the cue, as discussed herein.

Figure 18:
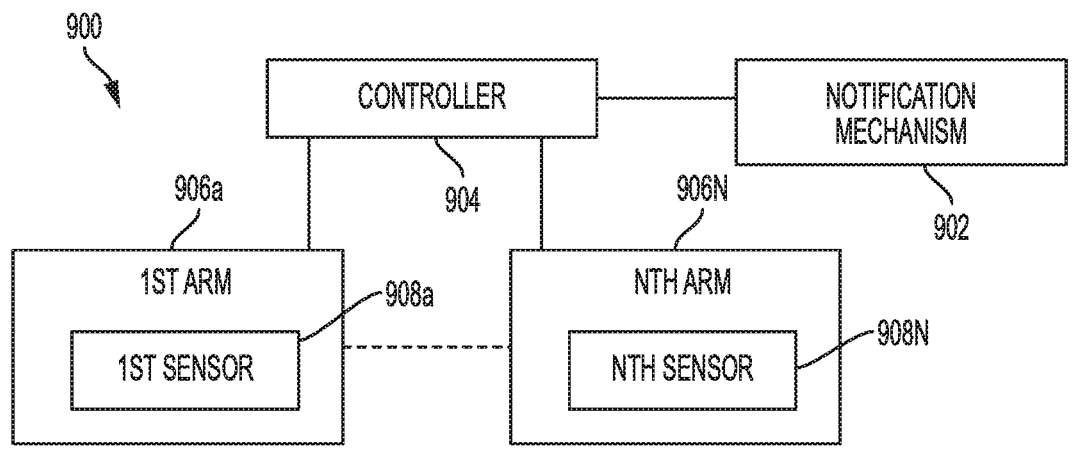
FIG. 18 is a schematic view of another embodiment of a robotic surgical system.

As mentioned above, at least some of the methods, systems, and devices for controlling movement of a robotic surgical system provided herein can be configured to facilitate detection of collision of a portion of the robotic surgical system with another object. FIG. 18 illustrates one embodiment of such a robotic surgical system 900. The robotic surgical system 900 can generally be configured and used similar to the robotic surgical system 200 of FIG. 3. The robotic surgical system 900 can include a computer system that includes a display device (not shown), a controller 904, a plurality of movement mechanisms 906a, 906N, and a notification mechanism 902 (e.g., an IO interface such as a display, a speaker, a light, etc.). In at least some embodiments, the notification mechanism 902 can be omitted, and the robotic surgical system 900 can be configured to provide notifications using another element thereof, as discussed further below. As in this illustrated embodiment, the movement mechanisms 906a, 906N can each include an electromechanical arm. The robotic surgical system 900 can include at least one movement mechanism 906a and, optionally, an additional one or more movement mechanisms for a total of "N" movement mechanisms, where N is greater than or equal to two. Each of the movement mechanisms 906a, 906N can be configured to couple to one of a plurality of surgical instruments (not shown), as discussed herein. The controller 904 can be configured to receive an input from a user (not shown) requesting movement, relative to a patient (not shown), of a master one of the surgical instruments 906a, 906N. The user can provide the input using a user input device (not shown) (e.g., a master input device), as discussed herein. The controller 904 can be configured to cause motors (not shown) of the robotic surgical system 900 to drive movement of the movement mechanisms 906a, 906N, as also discussed herein, thereby causing movement of the surgical instruments respectively coupled thereto.

As in this illustrated embodiment, each of the movement mechanisms 906, 906N can have at least one sensor 908a, 908N attached thereto. The sensors 908a, 908N can be configured to facilitate the detection of a collision of the one of the movements mechanisms 908a, 908b to which it is coupled with another object before the collision occurs. The sensors 908a, 908N can be configured to be in electronic communication with the controller 904. In this illustrated embodiment, each of the movement mechanisms 906a, 906N has a sensor attached thereto. In other embodiments, at least one but less than all of the "N" movement mechanisms 906a, 906N can have a sensor attached thereto, which may help reduce monetary cost of the system 900, may reduce processing demands on the controller 904, and/or may account for at least one of the "N" movement mechanisms being unlikely to move during performance of a surgical procedure (e.g., if the movement mechanism will have a surgical instrument coupled thereto that is unlikely to move during performance of a surgical procedure).

The sensors 908a, 908N can be attached to their respective movement mechanisms 906a, 906N in any of a variety of ways. In at least some embodiments, the sensors 908a, 908N can be directly attached to their respective movement mechanisms 906a, 906N, such as with magnet(s), with adhesive, by being embedded therein, etc. In at least some embodiments, the sensors 908a, 908N can be directly attached to their respective movement mechanisms 906a, 906N by being attached to a casing of the movement mechanism, such as a shroud or a drape. The casing can be configured to serve a cosmetic purpose (e.g., improve aesthetics of the system 900), to facilitate branding (e.g., by having a hospital name, manufacturer name, etc. printed thereon), and/or to serve a functional purpose (e.g., facilitate cleaning of the system 900 by allowing removal of the casing for replacement with either the same or a different casing for subsequent use of the system 900, carry electrical conductor(s), carry fluid conductor(s), etc.). In embodiments in which one or more of the sensors 909a, 908N are attached to a casing instead of directly to a movement mechanism, the detected collision may be between the casing and another object (e.g., another casing, another one of the arms, medical personnel, etc.) but is considered herein to be between the other object and the movement mechanism that includes the casing.

The sensors 908a, 908N can have any of a variety of configurations. In some embodiments, each of the sensors 908a, 908N can be of a same type as each other, which may facilitate assembly of the system 900 and/or may facilitate programming and/or processing of the controller 904. In other embodiments, one or more of the sensors 908a, 908N can have a type different from any of the others of the sensors 908a, 908N, which may allow collisions to be detected in two or more different ways and thereby help increase chances of a collision being prevented.

One type of sensor for the sensors 908a, 908N includes an energy probe configured to probe space with energy. One type of energy probe includes a light probe. The light probe can be passive, in which the sensor is configured to look for light from other sources, or active, in which the sensor is configured to look for light from its own source.

A passive light probe can be configured to sense light emitted by sources, such as other light probes. The passive light probe can also be configured to emit light configured to be sensed by other light probes. The light configured to be sensed by the light probe and the light configured to be emitted by the light probe can be light visible by the human eye or can be light, such as infrared light, that is not visible to the human eye. The light can have any of a variety of wavelengths and can be selected for compatibility with transmission windows in the sensor materials. The more light sources and detectors used may help increase a confidence in detected light and/or increase chances of detecting an impending collision. The fewer light sources and detectors used, the more cost effective the system may be. Each of the light probes can be associated with a light protection zone, with energy emitted and collected through the protection zone using diffusing fibers. Alternatively, the light probes as microstructured reflector arrays may distribute light generally away from the surface to which it is attached when illuminated by a beam parallel thereto, with returned or received light being collected and directed to a collocated detector similar to that which may occur with diffusing fibers.

The controller 904 can be configured to determine from the light sensed by the passive light probe whether a collision is impending. For example, when the light detected by the sensor is equal to or greater than a predetermined threshold amount of light, the controller 904 can be configured to determine that a possible collision is imminent. In other words, when a light sensed by the sensor is bright enough, the source of the sensed emitted light can be considered to be close to the arm to which the sensor is attached to indicate a possible impending collision. For another example, when the light detected by the sensor is increasing at a rate that is equal to or greater than a predetermined rate of increase, the controller 904 can be configured to determine that a possible collision is imminent. In other words, the source of the sensed emitted light can be considered to be becoming closer to the arm having the light probe attached thereto (by movement of the light source and/or by movement of the arm having the sensor attached thereto) such that a collision may be imminent. For yet another example, when the light detected by the sensor is increasing at a rate that is equal to or greater than a predetermined rate of increase and the light sensed by the sensor is bright enough, the controller 904 can be configured to determine that a possible collision is imminent.

An active light probe can be configured similar to a passive light probe but instead of being configured to sense light emitted by other light probes can be configured to sense its own light as reflected back thereto. The controller 904 can be configured to determine from the light sensed by the active light probe whether a collision is impending. For example, when the light detected by the sensor is equal to or greater than a predetermined threshold amount, the controller 904 can be configured to determine that a possible collision is imminent. In other words, when a light sensed by the sensor is bright enough, the object that reflected the light back to the sensor can be considered to be close to the arm to which the sensor is attached to indicate a possible impending collision. For another example, when the light detected by the sensor is increasing at a rate that is equal to or greater than a predetermined rate of increase, the controller 904 can be configured to determine that a possible collision is imminent. In other words, the object that reflected the light back to the sensor can be considered to be becoming closer to the arm having the light probe attached thereto (by movement of the light source and/or by movement of the arm having the sensor attached thereto) such that a collision may be imminent. For yet another example, when the light detected by the sensor is increasing at a rate that is equal to or greater than a predetermined rate of increase and the light sensed by the sensor is bright enough, the controller 904 can be configured to determine that a possible collision is imminent.

Another type of energy probe for the sensors 908a, 908N includes an electrical probe. In at least some embodiments, the electrical probe can include a transmission line. For example, the electrical probe can be configured to radiate energy from a leaky transmission line routed along a movement mechanism or along the casing of the movement mechanism, and the electrical probe can be configured to observe driving point characteristics of the leaky transmission line. The controller 904 can be configured to use time-domain reflectometry (TDR) to determine, based on the observed driving point characteristics, whether a possible collision is imminent. The controller 904 may accomplish this determination, for example, by considering a possible collision to be imminent when a magnitude of the detected reflections is equal to or greater than a predetermined threshold amount. For another example of the electrical probe configured as a transmission line, the electrical probe can include an array of low-efficiency antenna. The controller 904 can be configured to determine a standing wave ratio (SWR) of the transmission line, as the SWR will vary as objects are at different distances from the sensor. When the SWR is determined to be equal to or greater than a predetermined threshold amount, the controller 904 can determine that a possible collision is imminent.

In at least some embodiments, the electrical probe can include a conductive layer with respect to a common ground, such as a casing of a movement mechanism having a conductive outer layer with respect to a common ground. The controller 904 can be configured to determine current in the sensor's drive electrode, synchronous to the sensor's own signal (e.g., I and Q components thereof). Capacitance increases with decreasing distance, so the current flow will change accordingly. Thus, based on the determined current, the controller 904 can be configured to determine whether a possible collision is imminent. When the determined current has changed by more than a predetermined threshold amount, the controller 904 can determine that a possible collision is imminent. In other words, the higher the capacitance, the closer the nearby object and thus the more likely a collision may occur.

Another type of energy probe for the sensors 908a, 908N includes a sonic probe. The sonic probe can be passive, in which the sensor is configured to listen for sound from other sources, or active, in which the sensor is configured to listen for sound from its own source.

A passive sonic probe can be configured to sense sound emitted by sources, such as other sonic probes. The passive sonic probe can also be configured to emit sound configured to be sensed by other sonic probes. The sound configured to be sensed by the sonic probe can be a sound that is inaudible to a human, which may help prevent the sound from distracting medical personnel performing a surgical procedure. Sounds at subaudible frequencies can have a wavelength that is long enough for a single transducer to be used and can have a nearly omnidirectional radiation pattern. At superaudible frequencies, the movement mechanism and/or the casing thereon may be multiple wavelengths long. A single transducer may thus not be effective for these larger size systems. Multiple transducers may thus be used to account for the multiple wavelength size of an arm and/or casing by having phases and amplitudes to provide a radiating and sending pattern that covers the entire size.

The controller 904 can be configured to determine from the sound sensed by the passive sonic probe whether a collision is impending. For example, when the sound detected by the sensor is equal to or greater than a predetermined threshold amount of sound, the controller 904 can be configured to determine that a possible collision is imminent. In other words, when a sound sensed by the sensor is loud enough, the source of the sensed emitted sound can be considered to be close to the arm to which the sensor is attached to indicate a possible impending collision. For another example, when the sound detected by the sensor is increasing at a rate that is equal to or greater than a predetermined rate of increase, the controller 904 can be configured to determine that a possible collision is imminent. In other words, the source of the sensed emitted sound can be considered to be becoming closer to the arm having the sonic probe attached thereto (by movement of the sound source and/or by movement of the arm having the sensor attached thereto) such that a collision may be imminent. For yet another example, when the sound detected by the sensor is increasing at a rate that is equal to or greater than a predetermined rate of increase and the sound sensed by the sensor is loud enough or has a high enough dB level, the controller 904 can be configured to determine that a possible collision is imminent.

An active sonic probe can be configured similar to a passive sonic probe but instead of being configured to sense sound emitted by other sound probes can be configured to sense its own sound as reflected back thereto. The controller 904 can be configured to determine from the sound sensed by the active sonic probe whether a collision is impending. For example, when the sound detected by the sensor is equal to or greater than a predetermined threshold amount, the controller 904 can be configured to determine that a possible collision is imminent. In other words, when a sound sensed by the sensor is loud enough or has a high enough dB level, the object that reflected the sound back to the sensor can be considered to be close to the arm to which the sensor is attached to indicate a possible impending collision. For another example, when the sound detected by the sensor is increasing at a rate that is equal to or greater than a predetermined rate of increase, the controller 904 can be configured to determine that a possible collision is imminent. In other words, the object that reflected the sound back to the sensor can be considered to be becoming closer to the arm having the sonic probe attached thereto (by movement of the sound source and/or by movement of the arm having the sensor attached thereto) such that a collision may be imminent. For yet another example, when the sound detected by the sensor is increasing at a rate that is equal to or greater than a predetermined rate of increase and the sound sensed by the sensor is loud enough or has a high enough dB level, the controller 904 can be configured to determine that a possible collision is imminent.

Frequency has an inverse relationship to wavelength, so sounds being detected or emitted at higher frequencies have shorter wavelengths. It is thus more likely at higher frequencies that multiple transducers may be needed to account for the multiple wavelength size of an arm and/or casing when passive sonic probes are used. Thus, for higher frequencies, active sonic probes may be desired over passive sonic probes since a lower number of sonic probes may be needed.

Regardless of the type of energy probe used, the controller 904 can be configured to coordinate operations to reduce interference from the different energies involved in the case of multiple energy probes in use. For example, frequency channels, codes, or time slots could be assigned to different ones of the energy probes, and the controller 904 can thus be able to identify the various energy probes and energies sensed thereby. In at least some embodiments, the energy probe can be configured to include its own processing capability, such as by a sensor being included on a microchip that also includes a microprocessor, such that the energy probe can be configured to communicate sensed data and/or collision determination to the controller 904 only when the microprocessor determines that a possible collision is imminent. For example, the microprocessor can, similar to radio communications, be configured to use spread spectrum techniques, token passing, listen-before-talk, etc.

Another type of sensor for the sensors 908a, 908N includes a matter probe configured to probe space with matter. The matter probe contacting another object can be indicative of a possible imminent collision, e.g., possible imminent contact of the object with the movement mechanism to which the matter probe is attached. The matter probe can be configured to not disrupt overall functioning of the robotic surgical system 900. For example, the matter that probes space can be relatively small and/or exert a force that is not high enough to disrupt the overall functioning of the robotic surgical system 900.

One type of matter probe includes a mechanism extension that extends from a surface to which it are attached, e.g., from a surface of a movement mechanism or a casing thereof. The mechanism extension can be in the form of an elongate whisker that can be attached to the surface in any of a variety of ways, e.g., with adhesive, by plugging into a socket on the surface, etc. The whisker can have only one end thereof attached to the surface, or the whisker can have both its ends attached to the surface so as to form an arch. In an exemplary embodiment, a plurality of mechanism extensions can be attached to a movement mechanism and can extend in different directions therefrom, thereby helping to prevent a collision from occurring in any direction in which the movement mechanism moves or in any direction that an object approaches the movement mechanism.

The mechanism extension can have a variety of configurations. The mechanism extension can be flex-sensitive, such as through resistive, piezo, or optical sensing. The mechanism extension can be static, or, the mechanism extension can be configured to microscopically vibrate. The vibration may increase chances of contact of the mechanism extension with an object near the movement arm to which the mechanism extension is attached. The mechanism extension can be a standalone element, or the mechanism extension can be part of an array or strip including a plurality of mechanism extensions. The array or strip can be configured to attached as a unit to the surface, which may facilitate assembly and/or replacement.

The mechanical extension can extend a distance from the surface to which it is attached. The distance can define a threshold distance. An object more than the threshold distance away from the movement mechanism to which the mechanical extension is attached will not contact the mechanical extension, and the mechanical extension will thus not sense the object. An impending collision will thus not be detected between the object and the movement mechanism having the mechanical extension attached thereto. An object that is at a distance equal to or less than the threshold distance will contact the mechanical extension, and the mechanical extension will thus sense the object. An impending collision can thus be detected between the object and the movement mechanism having the mechanical extension attached thereto. Thus, the more the mechanical extension extends from the surface to which it is attached, the larger the threshold distance, and thus the more sensitive the system 900 will be to impending collisions.

The controller 904 can be configured to determine from a signal from the mechanism extension whether a collision is impending. For example, the mechanism extension can be configured to transmit a signal to the controller 904 in response to the mechanism extension contacting another object. In response to receipt of the signal from the mechanism extension, the controller 904 can determine that a collision is impending. In some embodiments, the mechanism extension can be configured to transmit the signal to the controller 904 only when the mechanism extension contacts an object, which may help conserve resources of the mechanism extension and/or the controller 904. In other embodiments, the mechanism extension can be configured to transmit the signal to the controller 904 at regular intervals, with the signal being a binary signal either indicating "yes," the mechanism extension contacted an object since the last transmitted signal, or "no," the mechanism extension has not contacted the object since the last transmitted signal. This continuous transmission of signals may allow the controller 904 to determine whether the movement mechanism has moved away from the object of potential collision, e.g., is a "no" signal is received after a "yes" signal. For another example, the mechanism extension can be configured to have a degree of bend that can be communicated to the controller 904. Based on the degree of bend of the mechanism extension, the controller 904 can determine whether the mechanism extension has contacted an object, such as by comparing the received degree of bend to a preset default degree of bend of the mechanism extension. If the received degree of bend is more than a predetermined amount above or below the preset degree of bend, the controller 904 can be configured to determine that the mechanism extension contacted an object and that a collision is imminent. For yet another example, the mechanism extension can be conductive, can be configured to be excited with a low, safe level of voltage, and can be configured to detect electrical contact with an object. The controller 904 can determine than a collision is impending based on the detected electrical contact. For still another example, the controller 904 can be configured to determine from signals received from each of a plurality of mechanism extensions attached to the same movement mechanism a direction of an object with which the movement mechanism may possibly imminently collide, such as by the varying electrical currents received from the different ones of the mechanism extensions and/or by the varying degrees of bend received from the different ones of the mechanism extensions. The controller 904 can thus be configured to determine an imminent collision based on a pattern of mechanism extension signals.

Another type of matter probe includes a cushion attached to a surface of a movement mechanism or a casing thereof. The cushion can be attached to the surface in any of a variety of ways, e.g., with adhesive, by being sprayed onto the surface, etc. In an exemplary embodiment, a plurality of cushions can be attached to a movement mechanism (directly or indirectly via a casing) and can extend in different directions therefrom, thereby helping to prevent a collision from occurring in any direction in which the movement mechanism moves or in any direction that an object approaches the movement mechanism.

The cushion can have a variety of configurations. The cushion can be, for example, in the form of a rib, a belt similar to a torpedo belt, a balloon, a foam, etc. The cushion as a balloon can be filled with any of a variety of materials, such as a liquid such as saline, a gas such as air, and a foam such as a reticulated foam. The cushion as a foam can be formed by, for example, molding the foam with materials and process conditions that yield a fused outer surface such that the foam need not be inside a balloon or have an outer coating. A cushion can have a single segment or chamber, or a cushion can have a plurality of segments or chambers.

The cushion can be pressurized or non-pressurized. A pressurized cushion can be pressurized in any of a variety of ways. For example, the cushion can be coupled to a pressure or inflation source provided in the movement mechanism or casing thereof to which the cushion is attached. A non-pressurized cushion can be non-pressurized in any of a variety of ways. For example, the cushion (e.g., a cushion of reticulated foam) can include a small leak (e.g., by including a small hole therein) configured to equalize internal and external pressure and thereby avoid slow pressure-driven dimensional changes that could occur with temperature and aging while still being responsive to more rapid changes associated with contact. For another example, a balloon, bladder, or other outer coating of a cushion can be sufficiently porous to allow slow pressure equalization and thereby be sensitive to pressure changes rather than the absolute value of its internal pressure.

The cushion can be configured to deform in response to a force applied thereto. Contact of the cushion with an object can be determined based on a pressure applied to the cushion, e.g., by an amount of the cushion's shape deformation. The controller 904 can be configured to determine from a signal from the cushion whether a collision is impending, where the signal is indicative of the pressure applied to the cushion. The controller 904 can be configured to determine that the higher the pressure, the more likely and/or the sooner a collision may occur.

The controller 904 of the robotic surgical system 900 can be configured to trigger performance of a remedial action (also referred to herein as a corrective action) in response to the controller 904 determining that a possible collision may occur based on information sensed by the sensors 908*a*, 908N. The remedial action can be configured to help prevent the collision from occurring. The collision may thus be avoided entirely, or the collision's adverse effects may be mitigated in the event that the collision cannot be avoided, such as because one or more of the colliding objects are moving too quickly to avoid collision after the detection of possible collision therebetween. Because the controller 904 can be configured to receive data sensed by the sensors 908*a*, 908N in real time with performance of a surgical procedure, the controller 904 can be configured to cause the remedial action to be performed during the surgical procedure and either prevent the collision entirely or at least reduce adverse effects of the collision should it nevertheless occur.

The remedial action can have a variety of configurations. For example, the remedial action can include any one or more of slowing a movement speed of the movement mechanism associated with the detected impending collision, adjusting the movement the movement mechanism associated with the detected impending collision in contradiction to the movement thereof requested by a user input to the robotic surgical system 900 requesting movement of the surgical instrument coupled to that movement mechanism, moving the object with which the movement mechanism associated with the detected impending collision may collide, and providing a notification to a user indicating that the movement mechanism associated with the detected impending collision is subject to an impending collision. The controller 604 can be configured to cause the notification mechanism 902 to provide the notification, e.g., by transmitting a signal thereto, to the user similar to that discussed above regarding the notification mechanism 610 providing a cue. The notification can include any one or more of an audible signal, a tactile signal, and a visual signal. The audible, tactile, and visual signals can be similar to the audible, tactile, and visual signals discussed above regarding the cue. As mentioned above, in embodiments in which the notification mechanism 902 is omitted, another portion of the robotic surgical system 900 can be configured to provide the notification, such as a display device of the system 900 being configured to display the notification thereon. In at least some embodiments, the controller 604 can be configured to not cause the notification mechanism 902 to provide the if the user's instrument manipulation remains unhindered by the remedial action(s), which may help avoid additional cognitive load on the user. In such instances, only when no mitigation is possible and a desired movement cannot be fulfilled because of irreducible collisions, the controller 604 can be configured to cause the notification mechanism 902 to provide the notification.

Figure 19:
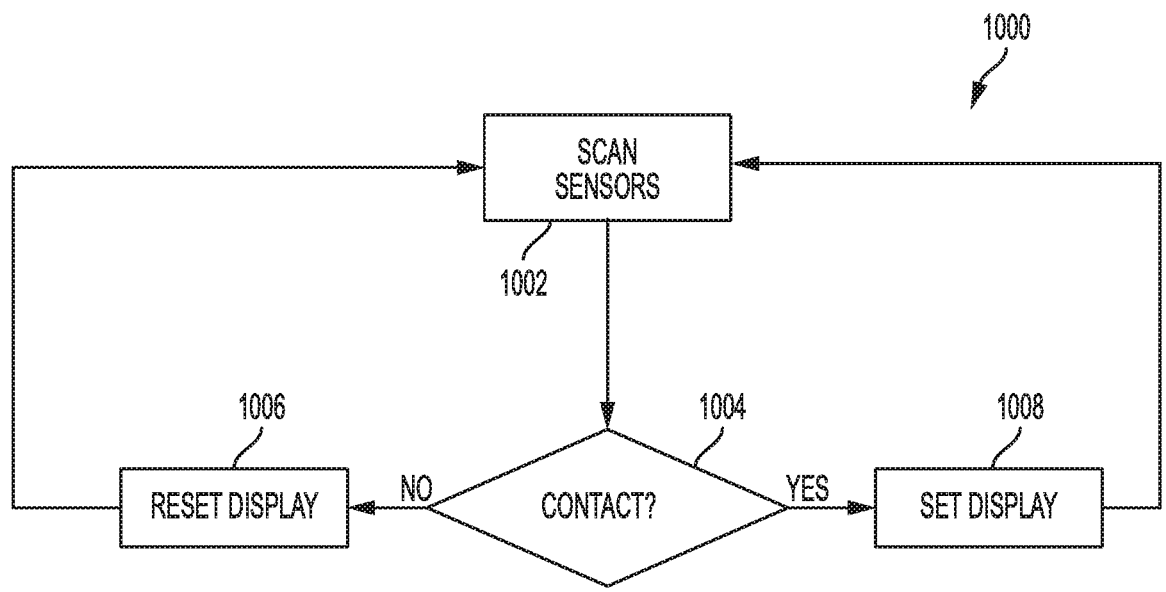
FIG. 19 is a flowchart of one embodiment of a process of detecting a possible collision in a robotic surgical system using one or more sensors.

FIG. 19 illustrates one embodiment of a process 1000 of the controller 904 triggering a remedial action based on data sensed by the sensors 908*a*, 908N. The controller 904 can be configured to scan 1002 the sensors 908*a*, 908N for signals. The scanning 1002 can be continuous, or the controller 904 can periodically query the sensors 908*a*, 908N at regular, predetermined intervals. Continuous scanning 1002 may facilitate the identification of potential collisions before they occur. Periodic scanning 1002 may help conserve system resources. The sensors 908*a*, 908N can all be continuously scanned 1002, can all be periodically scanned 1002 (at the same or different intervals from one another), or at least one of the sensors 908*a*, 908N can be continuously scanned 1002 and a remainder of the sensors 908*a*, 908N can be periodically scanned 1002.

The scanning 1002 can include the controller 904 sending a query to each of the sensors 908*a*, 908N requesting a reply. Alternatively, the sensors 908*a*, 908N can be configured to transmit sensed data to the controller 904 without receiving a request for the data from the controller 904.

Based on data received from the sensors 908*a*, 908N, the controller 904 can determine 1004 whether contact is imminent between one of the movement mechanisms 906*a*, 906N and another object. The determining 1004 can involve any number of different types of analysis, as discussed above. If contact is determined 1004 as not being imminent, the controller 904 can reset 1006 and continue scanning 1002. The resetting 1006 can include resetting a clock that counts time for when the next scanning 1002 should occur and/or can include resetting a display to stop providing notification of an impending collision previously detected. In other embodiments, as mentioned above, the notification mechanism 902 and/or other aspect of the system 900 can instead or also provide the notification instead of the display.

If contact is determined 1004 as being imminent, the controller 904 can cause 1008 the display to provide notification of the detected impending collision. The notification on the display can include, for example, text such as "First Arm Contact," "First Arm Reports Contact," "First Arm Impending Contact," "Second Arm Contact At Joint Three," "Second Arm Reports Medial Contact," "Contact For First Trocar's Instrument," "Second Arm Contact From Above," "Second Arm Contact From Left," a message indicating a modification of the instrument pose determined by the system 900 that would allow the instrument to avoid the collision and resume uninhibited movement such as a message of "Rotate right tool slightly clockwise or push it left to eliminate external collisions," etc., and/or an image such as a 3-D graphical indicator (e.g., a colored wedge, pyramidal frustum, etc.) overlaid on the instrument tip indicating how the instrument's pose can be revised to avoid the collision with a size or other attribute of the indicator indicating the relative merit (freedom attained) of the revised pose since the user can be free to adjust one instrument having an overlaid image but not another instrument having another overlaid image, etc. As mentioned above, the notification mechanism 902 and/or other aspect of the system 900 can instead or also provide the notification instead of the display. The notification includes a visual display in this illustrated embodiment, but as mentioned above, the notification can include any one or more of visual, tactile, and audible signals.

After determining 1004 that a collision is imminent, the controller 904 can cause a clock that counts time to be reset for when the next scanning 1002 should occur.

Figure 20:
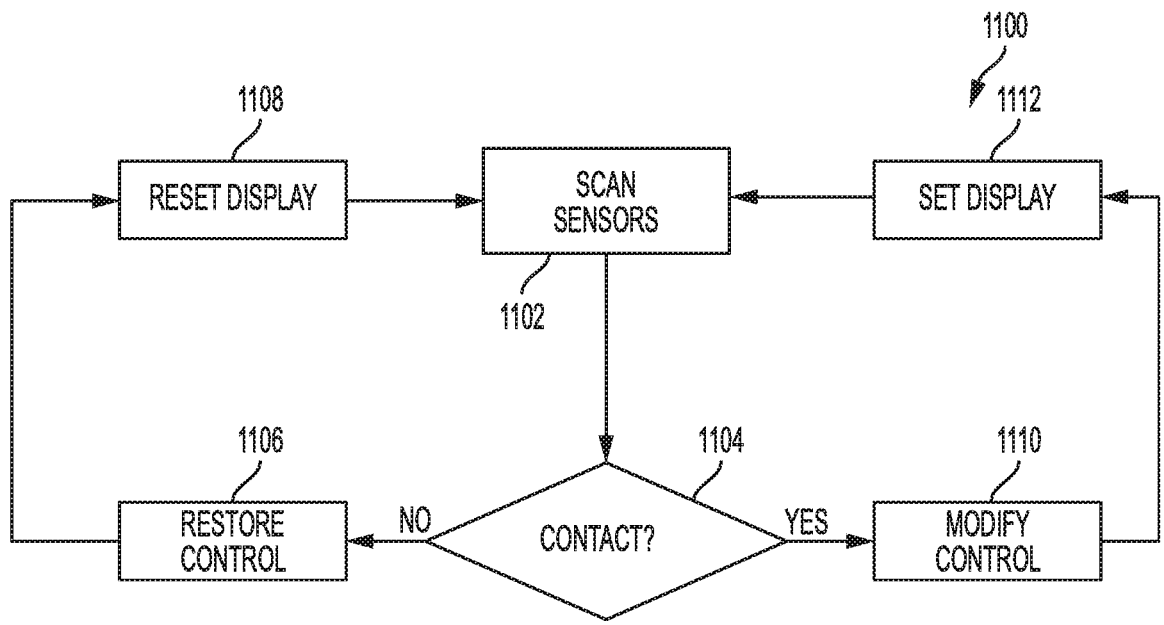
FIG. 20 is a flowchart of another embodiment of a process of detecting a possible collision in a robotic surgical system using one or more sensors.

In the illustrated embodiment of FIG. 19, the remedial action triggered by the controller 904 in response to a detected impeding collision, which may be provided before, concurrent with, and/or after the collision occurs, includes the providing of a notification. FIG. 20 illustrates another embodiment of a process 1100 of the controller 904 triggering a remedial action based on data sensed by the sensors 908*a*, 908N, with the remedial action including providing of a notification and causing an adjustment of the robotic surgical system 900. This adjustment may prevent the detected possible collision from occurring at all, even if the user controlling the system 900 does not take any specific action in order to prevent the collision.

In the process 1100 of FIG. 20, the controller 904 can be configured to scan 1102 the sensors 908a, 908N for signals similar to the scanning 1002 discussed above. Based on data received from the sensors 908a, 908N, the controller 904 can determine 1104 whether contact is imminent between one of the movement mechanisms 906a, 906N and another object, similar to that discussed above regarding the determining 1004.

If contact is determined 1104 as not being imminent, the controller 904 can restore control 1106 and can reset 1108 similar to the resetting 1006 discussed above. The restoration 1106 of control can include allowing movement of the movement mechanisms 906a, 906N to be controlled via user input device, which may either be maintaining control via the user input device or to stop automatic control in the event of a previously detected imminent collision. Additionally or alternatively, the restoration 1106 of control can include returning a movement mechanism that was moved in response to a previously detected imminent collision back to its pre-detected collision position. The movement mechanism may have been moved to a mechanically disadvantageous position and/or may have moved close to another object. Returning the movement mechanism to its previous position may thus allow the movement mechanism to be moved from the mechanically disadvantageous position and/or move the movement mechanism away from the other object it moved closed to and may have thus increased its chances of colliding therewith.

The restoration 1106 of control occurs before the resetting 1108 in this illustrated embodiment, but the resetting 1108 can occur first, or the resetting 1108 and the restoring 1106 can be concurrent. After the restoration 1106 of control and the resetting 1108, the scanning 1102 can continue.

If contact is determined 1104 as being imminent, the controller 904 can cause 1110 automatic movement of a portion of the robotic surgical system 900 to help prevent the impending collision and/or mitigate adverse effects of the collision should it occur. The automatic movement can include any one or more of at least one of changing a shape of the movement mechanism associated with the sensor associated with the detected impending collision, changing a shape of the movement mechanism that may potentially collide with the movement mechanism associated with the sensor associated with the detected impending collision, slowing a speed of the movement mechanism associated with the sensor associated with the detected impending collision (which may include stopping the movement entirely), adjusting the movement of the movement mechanism associated with the sensor associated with the detected impending collision in contradiction to the movement requested by user input to the robotic surgical system 900, and moving the other portion of the robotic surgical system 900 that may collide with the movement mechanism associated with the sensor associated with the detected impending collision. Changing a shape of a movement mechanism can include, for example, bending the movement mechanism, such as bending the movement mechanism at any one or more joints of the movement mechanism.

Also, referring again to FIG. 20, if contact is determined 1104 as being imminent, the controller 904 can cause 1112 the display to provide notification of the detected impending collision, similar to the setting 1008 of the display discussed above. The modification 1110 of control occurs before the setting 1112 in this illustrated embodiment, but the setting 1112 can occur first, or the setting 1112 and the modifying 1110 can be concurrent. After the modifying 1110 of control and the setting 1112, the scanning 1102 can continue.

Figure 21:
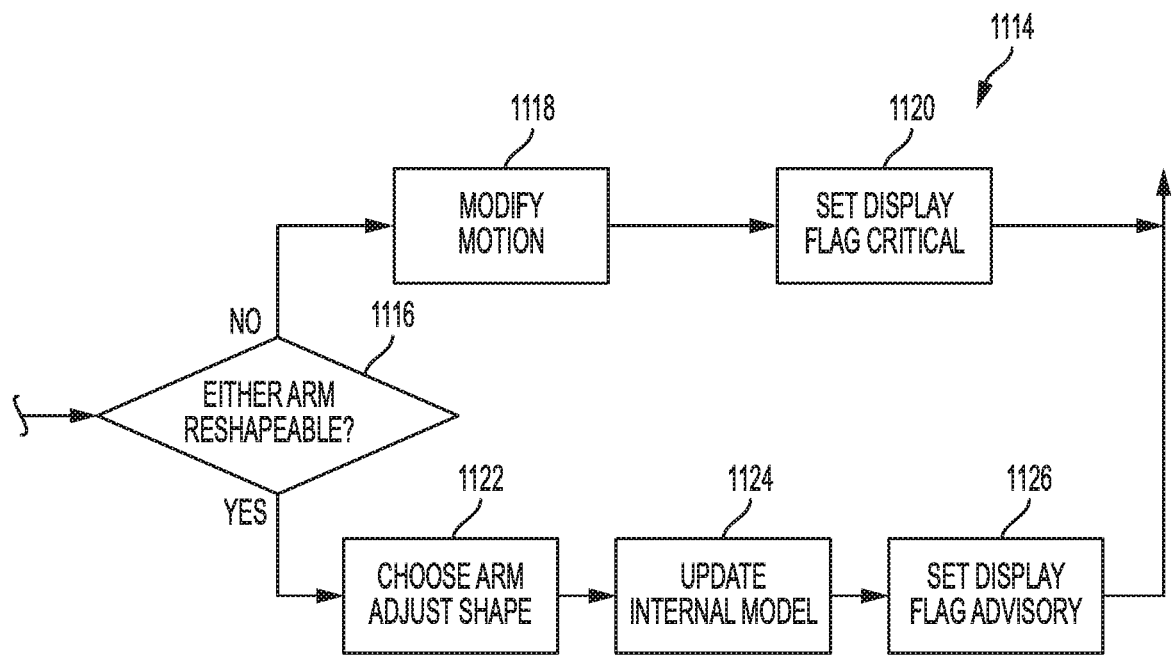
FIG. 21 is a flowchart of one embodiment of a process of reacting to a detection of a possible collision in a robotic surgical system.

FIG. 21 illustrates one embodiment of a process 1114 of the controller 904, in response to determining 1104 that contact is imminent, causing a change in shape of a movement mechanism in the event that the two objects that may imminently collide include two of the movement mechanisms 906a, 906N. The controller 904 can determine that two of the movement mechanisms 906a, 906N are the subject of the imminent collision in any of a variety of ways, such as by receiving signals indicative of a potential collision from each of the two movement mechanisms' sensors 908a, 908N simultaneously, thereby indicating that the collision is likely with each other. A person skilled in the art will appreciate that signals may not be received exactly simultaneously but nevertheless be considered to be received simultaneously due to factors such as very small delays in controller 904 processing capability. For another example, a reflected sound received by a movement mechanism can have a different characteristic pattern if reflected back from another movement mechanism than from another object such as a person.

If contact is determined 1104 as being imminent, the controller 904 can determine 1116 if either of the two of the movement mechanisms 906a, 906N at issue are configured to change shape. The determination 1116 can include, for example, looking up the two of the movement mechanisms 906a, 906N at issue in a lookup table that indicates a shape changing capability for each of the movement mechanisms 906a, 906N in the system 900 with a binary true/false value. A movement mechanism can be configured to change shape by bending at one or more points along a length thereof, such as if the movement mechanism includes a plurality of joints or if the movement mechanism includes a flexible elongate shaft.

If neither of the two of the movement mechanisms 906a, 906N at issue are configured to change shape, the controller 904 can cause 1118 automatic movement of a portion of the robotic surgical system 900 and/or the provision of a notification, as discussed above. The notification can include notice 1120 to the user that a critical collision condition exists as a reflection that movement mechanism shape cannot be adjusted.

If only one of the two of the movement mechanisms 906a, 906N at issue is configured to change shape, the controller 904 can cause that one of the movement mechanisms 906a, 906N to change shape.

If both of the two of the movement mechanisms 906a, 906N at issue is configured to change shape, the controller 904 can change the shape of both of the two of the movement mechanisms 906a, 906N at issue. Alternatively, the controller 904 can be configured to choose 1122 one of the two of the movement mechanisms 906a, 906N at issue to change in shape. Changing the shape of only one of the movement mechanisms 906a, 906N at issue may help prevent the movement mechanism whose shape is changed from risking collision with another object it may move closer to as a result of the shape change. The controller 904 can be configured to choose 1112 one of the two of the movement mechanisms 906a, 906N at issue in any of a variety of ways. For example, the controller 904 can be configured to determine from an electronic model of the robotic surgical system 900 that reflects a current position of each of the movement mechanisms 906a, 906N which one of the two movement mechanisms 906a, 906N at issue is less likely to risk collision with another object it may move closer to as a result of the shape change, such as by determining which of the two movement mechanisms 906a, 906N at issue is farther away from objects adjacent thereto. The controller 904 can cause 1122 the chosen one of the two movement mechanisms 906a, 906N at issue to change in shape.

The controller 904 can update 1124 the model to reflect the caused shape change and can provide 1126 a notification, as discussed above. The notification can include an advisory notice to the user that a shape of a movement mechanism shape has been adjusted. The updating 1124 occurs before the setting 1126 in this illustrated embodiment, but the setting 1126 can occur first, or the setting 1126 and the updating 1124 can be concurrent.

As mentioned above, at least some of the methods, systems, and devices for controlling movement of a robotic surgical system provided herein can be configured to facilitate movement of a surgical instrument between different anatomical quadrants. The robotic surgical system can generally be configured and used similar to the robotic surgical system 200 of FIG. 3. The robotic surgical system can include a computer system that includes a display device, a controller, and a plurality of movement mechanisms. The robotic surgical system can include at least two movement mechanisms and, optionally, an additional one or more movement mechanisms for a total of "N" movement mechanisms, where N is greater than or equal to three. Each of the movement mechanisms can be configured to couple to one of a plurality of surgical instruments, as discussed herein. The controller can be configured to receive an input from a user requesting movement, relative to a patient, of a one of the surgical instruments. The user can provide the input using a user input device (e.g., a master tool), as discussed herein. The controller can be configured to cause motor(s) of the robotic surgical system to drive movement of the movement mechanism having the one of the surgical instruments coupled thereto, as also discussed herein, thereby causing movement of the one of the surgical instruments in accordance with the user's input.

The robotic surgical system can have first and second modes of operation. In the first mode of operation, the robotic surgical system can be configured to only move the one of the surgical instruments that the user requests movement of via the input device. The first mode may therefore allow the one of the surgical instruments to move relative to all other surgical instruments coupled to the robotic surgical system via the other movement mechanisms. In other words, in the first mode, movement of the surgical instrument changes the surgical instrument's spatial positioning relative to the others of the surgical instruments. In the second mode of operation, the robotic surgical system can be configured to move the one of the surgical instruments that the user requests movement of via the input device in addition to one or more of the other surgical instruments coupled to the robotic surgical system. The second mode may therefore allow the two or more of the surgical instruments that are moved to maintain a relative position relative to each other. In other words, in the second mode, the multiple surgical instruments that move maintain a fixed spatial relationship to one another.

The robotic surgical system can be configured to selectively move between the first and second modes in response to a user input to the robotic surgical system, e.g., an input via the user input device such as a pressing of a "mode" button thereon. The robotic surgical system can thus be configured to allow the user to decide when an input to move a surgical instrument should move only that surgical instrument and when the surgical instrument should move in conjunction with one or more other surgical instruments. In at least some embodiments, in addition to the robotic surgical system being configured to selectively move at least from the first mode to second mode in response to the user input, the robotic surgical system can be configured to automatically move from the second mode to the first mode. The automatic movement can occur after the robotic surgical system receives the user input requesting movement of the surgical instrument such that the next user input requesting movement of the surgical instrument will move only that surgical instrument unless the user manually provides another input moving from the first mode to the second mode. The automatic movement from the second mode to the first mode may help prevent inadvertent coordinated movement of surgical instruments, which may be more likely to occur when user inputs requesting movement of the surgical instruments are separated by enough time for the user to possibly forget that the robotic surgical system is in the second mode.

When the robotic surgical system is in the first mode, the robotic surgical system can be configured to move the surgical instrument that is next instructed by the user to move relative to the others of the surgical instruments, and when the robotic surgical system is in the second mode, the robotic surgical system can be configured to move the surgical instrument that is next instructed by the user to be moved and to correspondingly move the others of the surgical instruments. The robotic surgical system can thus be configured in a simple manner in which a specific one of the surgical instruments is not pre-selected as a "master" tool that others of the surgical instruments follow as "slave" tools follow, nor are any one or more of the surgical instruments pre-selected as "slave" tools since instead all surgical instruments move in conjunction with the master tool. Such a configuration may be useful when a surgical instrument including a camera is desired to always move in conjunction with another surgical instrument to keep the other surgical instrument within the camera's field of view. In other embodiments, the robotic surgical system can be configured to allow user pre-selection of a one of the surgical instruments as the master tool. The user may thus have more flexibility in deciding how surgical instruments should move since different ones of the surgical instruments can be the master tool at different times during performance of a surgical procedure. Selection of a surgical instrument as the master tool can be accomplished in any of a variety of ways, such as via the user input device or via an IO device coupled to the robotic surgical system. In addition or alternative to the robotic surgical system being configured to allow user pre-selection of the master tool, the robotic surgical system can be configured to allow user pre-selection of one or more of the surgical instruments as slave tools. The user may thus have more flexibility in deciding how surgical instruments should move since different ones of the surgical instruments can move in conjunction with the master tool at different times during performance of a surgical procedure. Selection of surgical instruments as slave tools can be accomplished in any of a variety of ways, such as via the user input device or via an IO device coupled to the robotic surgical system.

In at least some embodiments, when a camera is one of a plurality of surgical instruments in use in a surgical procedure being performed using the robotic surgical system, the camera can be automatically selected by the robotic surgical system as a slave tool. The camera can thus be ensured to move in coordination with other surgical instrument(s) being moved, thereby helping to keep the camera trained on the instrument(s) being moved. No portion of the camera will typically be within the camera's field of view, so automatically designating the camera as a slave tool may facilitate selection the camera as a slave tool in embodiments in which tools selected for coordinated movement are selected based on their visibility on a display.

In at least some embodiments, when a camera is one of a plurality of surgical instruments in use in a surgical procedure being performed using the robotic surgical system, the camera can be selected by a user as either a master tool or a slave tool. The camera's movement may thus be more in the control of the user. Since no portion of the camera will typically be within the camera's field of view, in embodiments in which tools selected for coordinated movement are selected based on their visibility on a display, the camera can be selected in another way, such as by selecting a "camera" icon on the display or by selecting the camera from a list of surgical instruments currently in use that is provided on the display. In embodiments in which a list of surgical instruments currently in use is provided on a display, whether or not one of the surgical instruments includes a camera, one or more instruments can be selected for movement from the list, such as by checking a check box next to selected one(s) of the instruments or by clicking on text, icon, picture, etc. identifying an instrument.

In at least some embodiments, when a camera is one of a plurality of surgical instruments in use in a surgical procedure being performed using the robotic surgical system, the camera can be configured to be controlled using a first user input device and the other surgical instrument(s) can be configured to be controlled using a second user input device. The camera can thus be configured to be controlled independent of the other surgical instrument(s), which may facilitate zooming in/out and/or other field of view changes during movement of any of the other surgical instrument(s), which may help keep the moving instrument(s) within the camera's field of view. One example of first and second input devices includes two hand held devices, one operated by a user's left hand and another operated by the user's right hand. Another example of first and second input devices includes a handheld device operated by a user's hand and a foot-operated device operated by the user's foot.

Figure 22:
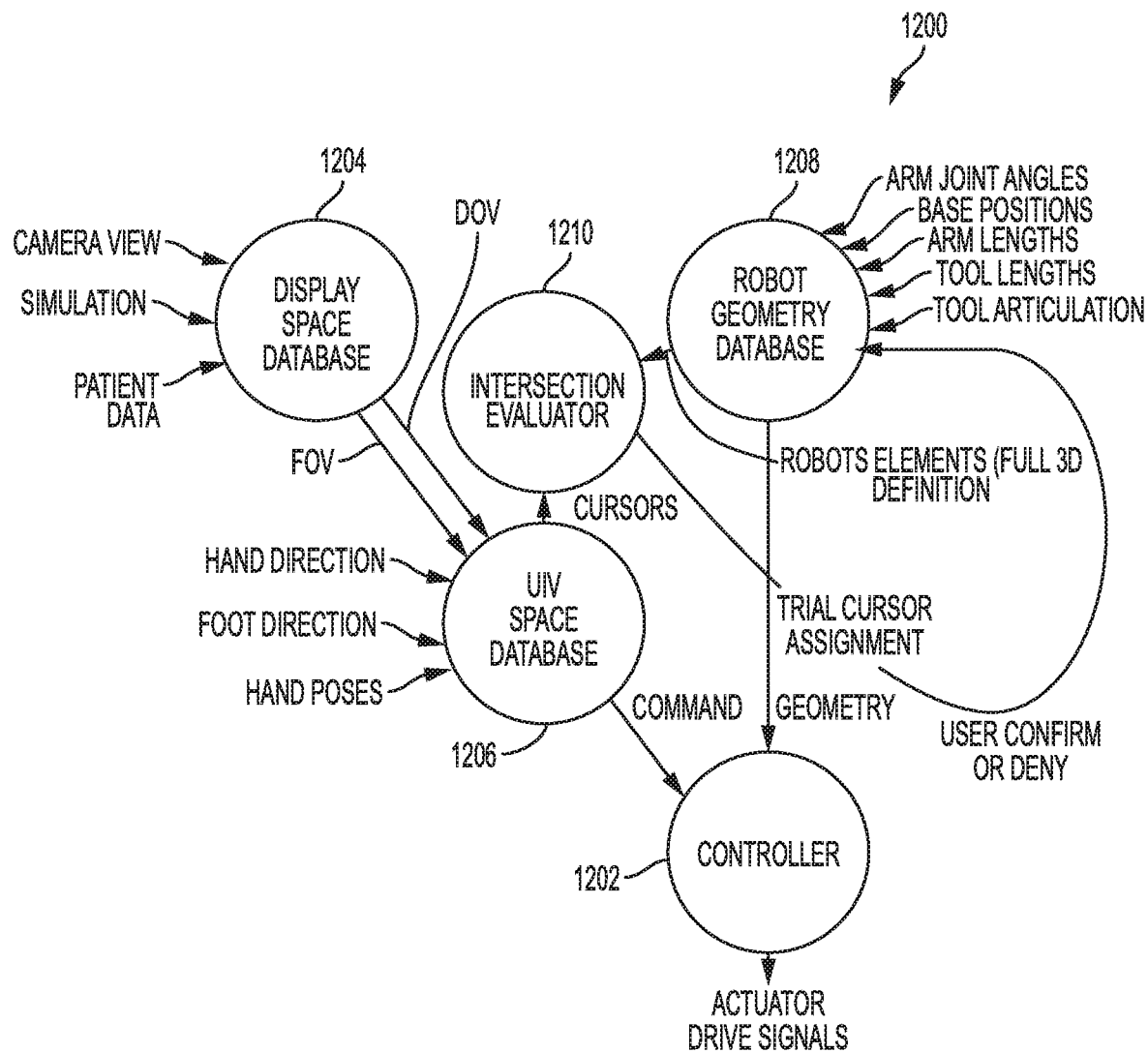
FIG. 22 is a schematic view of another embodiment of a robotic surgical system.

FIG. 22 illustrates one embodiment of a robotic surgical system 1200 configured to facilitate movement of a surgical instrument between different anatomical quadrants. The robotic surgical system 1200 can generally be configured and used similar to the robotic surgical system 200 of FIG. 3. For ease of illustration, only some portions of the system 1200 are shown in FIG. 22. The robotic surgical system 1200 can include a computer system that includes a display device (not shown), a controller 1202, and a plurality of movement mechanisms (not shown) each configured to removably couple to one of a plurality of surgical instruments (not shown). As in this illustrated embodiment, the robotic surgical system 1200 can include a display space database 1204, a user input device (UID) database 1206, and a robot geometry database 1208. The databases 1204, 1206, 1208 are shown an individual databases in this illustrated embodiment, but any one or more of the databases 1204, 1206, 1208 can be combined together.

The display space database 1204 can be configured to receive and store camera view data indicative of a field of view of a camera coupled to the robotic surgical system 1200 via a movement mechanism thereof, patient data indicative of data related to a patient (e.g., anatomical data, etc.) to have or having a surgical procedure performed thereon using the robotic surgical system 1200, and simulation data indicative of a simulated surgical procedure performed on the patient before commencement of an actual surgical procedure on the patient.

The UID database 1206 can be configured to receive and store input from each user input device coupled to the robotic surgical system 1200, such as poses of user input devices configured to be operated by hand as well as any other signals such as the state of various switches they may provide, the values of signals provided by foot-operated user input devices, and can be configured to receive and store field of view (FOV) data and direction of view (DOV) data from the display space database 1204. The UID database 1206 can be configured to provide command data to the controller 1202 indicative of input the robotic surgical system 1200 receives from a user input device so the controller 1202 can actuate the user input device signal. In other words, so the controller 1202 can cause appropriate action to be taken in response thereof, e.g., move between the first and second modes, cause movement of one or more surgical instruments in accordance with in the user input. The UID database 1206 can be configured to provide cursor data to an intersection evaluator 1210 configured to facilitate association of a cursor of a cursor that may be overlaid on an image with objects in the image itself. The intersection evaluator 1210 is shown as a separate element from the controller 1202 in this illustrated embodiment, but the controller 1202 can perform the functions of the intersection evaluator 1210.

The robot geometry database 1208 can be configured to receive and store joint angles of the movement mechanisms, positions of a base or frame of the robotic surgical system 1202, lengths of the movement mechanisms, lengths of the surgical instruments coupled to the movement mechanisms, and data regarding articulation of the surgical instruments coupled to the movement mechanisms. The robot geometry database 1208 can be configured to provide data stored therein to the intersection evaluator 1210 to facilitate association of cursors with objects such as any one or more of instruments, patient anatomy, and derived entities. The robot geometry database 1208 can be configured to provide data stored therein to the controller 1202 to facilitate various processing operations of the controller 1202. The robot geometry database 1208 can be configured to receive cursor data from the intersection evaluator 1210, e.g., from the controller 1202, thereby allowing non-geometric or "meta" data to be included in the data reflective of the robot surgical system's configuration. The cursor data can include identification of which one of the surgical instruments coupled to the movement mechanisms is the master tool and which one or more of the surgical instruments coupled to the movement mechanisms are the slave tools that follow the movement of the master tool when the robotic surgical system 1200 is in the second mode.

Figure 23:
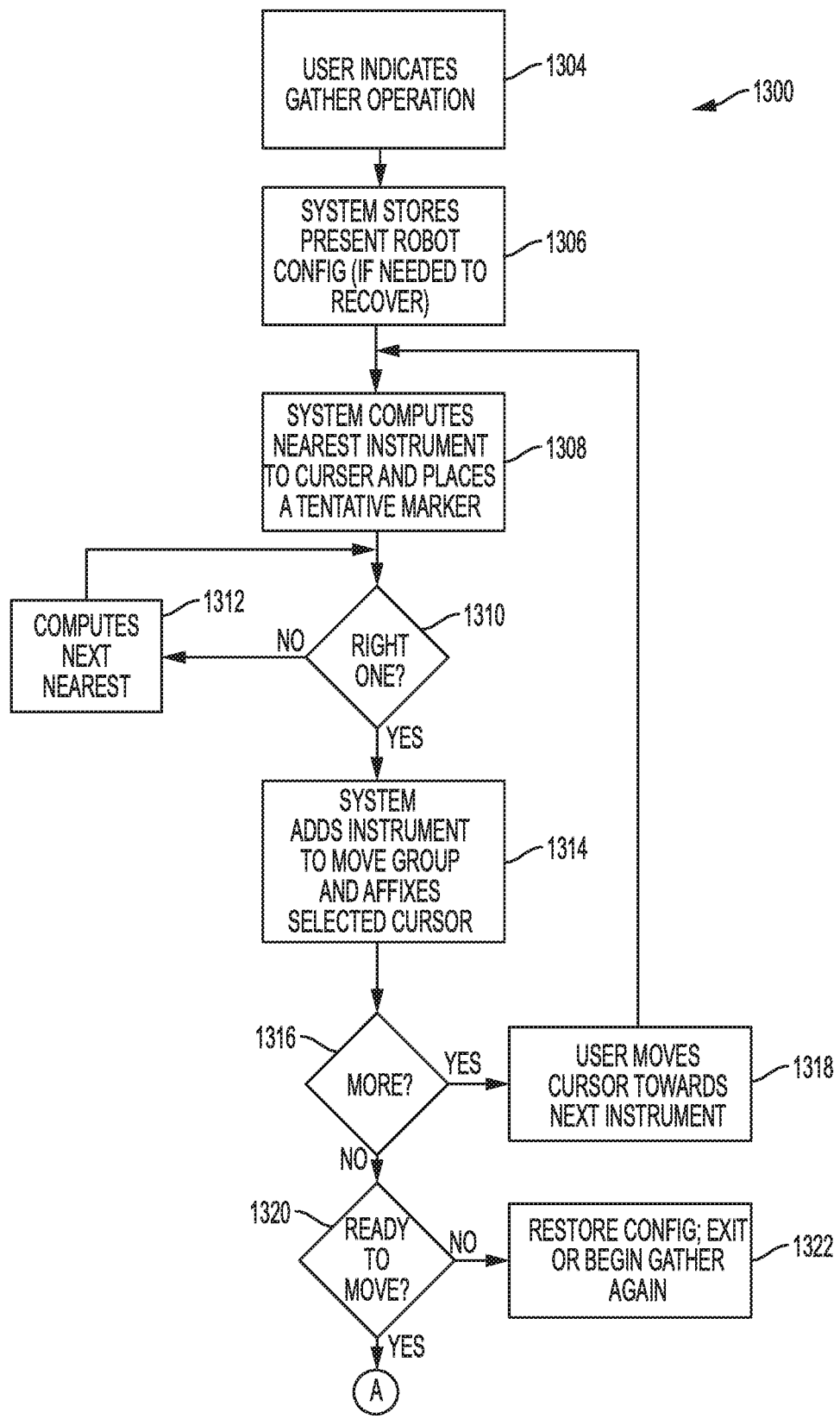
FIG. 23 is a flowchart showing one embodiment of a first portion of a process of a robotic surgical system facilitating movement of a surgical instrument between different anatomical quadrants.
Figure 24:
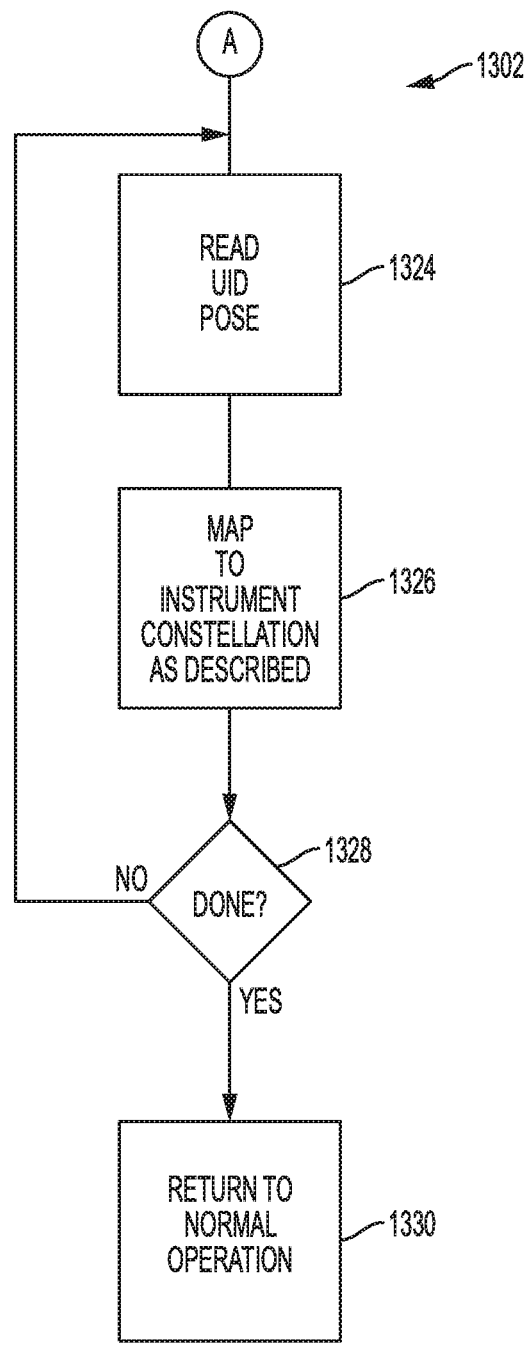
FIG. 24 is a flowchart showing a second portion of the process of FIG. 23.

FIGS. 23 and 24 illustrate one embodiment of a process of a robotic surgical system facilitating movement of a surgical instrument between different anatomical quadrants. A first portion 1300 of the process in FIG. 23 is generally a "gathering" process in which one or more surgical instruments coupled to the robotic surgical system (e.g., removably coupled to one or more movement mechanisms of the robotic surgical system) are selected as tools to move in conjunction with one another to maintain fixed spatial positioning therebetween, e.g., the slave tool(s) are gathered. A second portion 1302 of the process in FIG. 24 is generally a "follow" process in which the selected one or more instruments are moved in accordance with user-instructed movement.

A user of the robotic surgical system can indicate 1304 that the gathering process 1300 should begin. The user can provide the indication 1304 in any of a variety of ways, as discussed above. In response to the indication 1304, the robotic surgical system (e.g., a controller thereof) can store 1306 a present configuration of the robotic surgical system, e.g., store a present configuration of the movement mechanisms thereof. The stored 1306 present configuration may be used by the system in the event that the user would like to restore positioning of the surgical instruments coupled to the system to their position prior to the movement of the selected tool(s) that occurs later in the follow process 1302.

The robotic surgical system (e.g., the controller thereof) can suggest 1308 one of the surgical instruments to the user as a first tool for movement. The suggestion 1308 can, as in this illustrated embodiment, be based on where a user-controlled cursor is currently positioned on a display screen coupled to the robotic surgical system. A one of the surgical instruments closest to the cursor can be the suggested 1308 one of the instruments. The robotic surgical system (e.g., the controller thereof) can cause a marker (e.g., an "X," a dot, a bullseye, a quatrefoil, a square, etc.) to be visible on the screen that identifies the suggested 1308 one of the instruments. The user can provide an input to the system (e.g., via a user input device) indicating 1310 whether the suggested 1308 one of the instruments is an instrument that the user would like to move. If not, the robotic surgical system (e.g., the controller thereof) can suggest 1312 another one of the surgical instruments. As in this illustrated embodiment, the next suggested 1312 one of the surgical instruments can be a one of the surgical instruments that is next nearest to the cursor's current position. Once the suggested 1308 instrument is an instrument that the user would like to move, the robotic surgical system (e.g., the controller thereof) can add 1314 the selected instrument to a "move group" that includes all instruments selected as tools to move. The robotic surgical system (e.g., the controller thereof) can cause a marker (e.g., an "X," a dot, a bullseye, a quatrefoil, a square, etc.) to be visible on the screen that identifies the added 1314 one of the instruments. The marker used to identify a suggested 1308 instrument can be different than the marker used to identify an added 1314 instrument, which may help the user easily visually identify selected tools.

A location of where the marker is overlaid on the image of the selected instrument can be determined in any of a variety of ways. The camera image on the display has a plurality of pixels that each corresponds to a particular direction of incoming light. When the cursor is placed within the camera's field of view on the display, the user is specifying a direction in the field of view, which generally corresponds to a direction with respect to an elongate shaft of the camera. The robotic surgical system (e.g., the controller thereof) can compute a first line from the camera's lens in the direction of the field of view and a second line along a longitudinal axis of the selected instrument's elongate shaft (which can be known due to the known geometry of the movement mechanism to which the selected instrument is coupled). An articulated end effector at a distal end of the selected instrument's elongate shaft can, in at least some embodiments, be accounted for by adding a bend to a distal end of the second line. The first and second lines can be in three dimensions. The robotic surgical system (e.g., the controller thereof) can find where the first line comes closest to the second line and place the cursor at that location. The marker can thus not only mark the selected instrument but a location on the selected instrument. The robotic surgical system can allow the user to adjust a position of the marker on the selected instrument, such as by dragging and dropping of the marker.

The first added 1314 instrument can serve as a master tool. The user can indicate 1316 whether or not the user would like to select another one of the instruments, such as by moving 1318 the cursor toward another one of the surgical instruments. If no further tools are selected, the selected one tool can move on its own, e.g., with the robotic surgical system operating in the first mode. If one or more additional tools are selected and added 1314 to the group, the selected tools can all move in accordance with the user-instructed movement of the master tool, e.g., with the robotic surgical system operating in the second mode.

Once the user has selected all of the tools, the user can choose 1320 to continue to the follow process 1302, e.g., choose to move the selected tool(s), or to cancel 1322 the tool selections. The cancellation 1322 can allow the user to either start the tool selection process again or cancel the second mode and perform some other aspect of the surgical procedure. The user's choice 1320 can be indicated in any of a variety of ways, such as via the user input device. Examples of cancelling 1322 include the user moving the cursor on the display screen to select a "cancel" icon thereon. In this illustrated embodiment, the user choosing 1320 to proceed with movement of the selected tool(s) is indicated by the user providing 1324 an input to the robotic surgical system indicating desired movement of the master tool (e.g., providing an input to the user input device). The robotic surgical system (e.g., the controller thereof) can cause 1326 movement of the master tool and any selected slave tools in accordance with the provided 1324 input such that the selected slave tool(s) move in correspondence to the master tool's movement. To facilitate this coordinated movement, the robotic surgical system (e.g., the controller thereof) can map the master tool and the selected slave tool(s) to an electronic constellation defined by the coordinate systems of each of the master tool and the selected slave tool(s) and including points representative of the tools' locations. The electronic constellation can correspond to the configuration of the robotic surgical system mentioned above. The user can provide 1328 additional movement instructions to cause movement of the selected tool(s). After all movement of the selected instrument(s) desired by the user has been accomplished, the robotic surgical system (e.g., the controller thereof) can end 1330 the process and allow other aspects of the surgical procedure to be performed, which may include one or more additional gather/follow processes.

Figure 25:
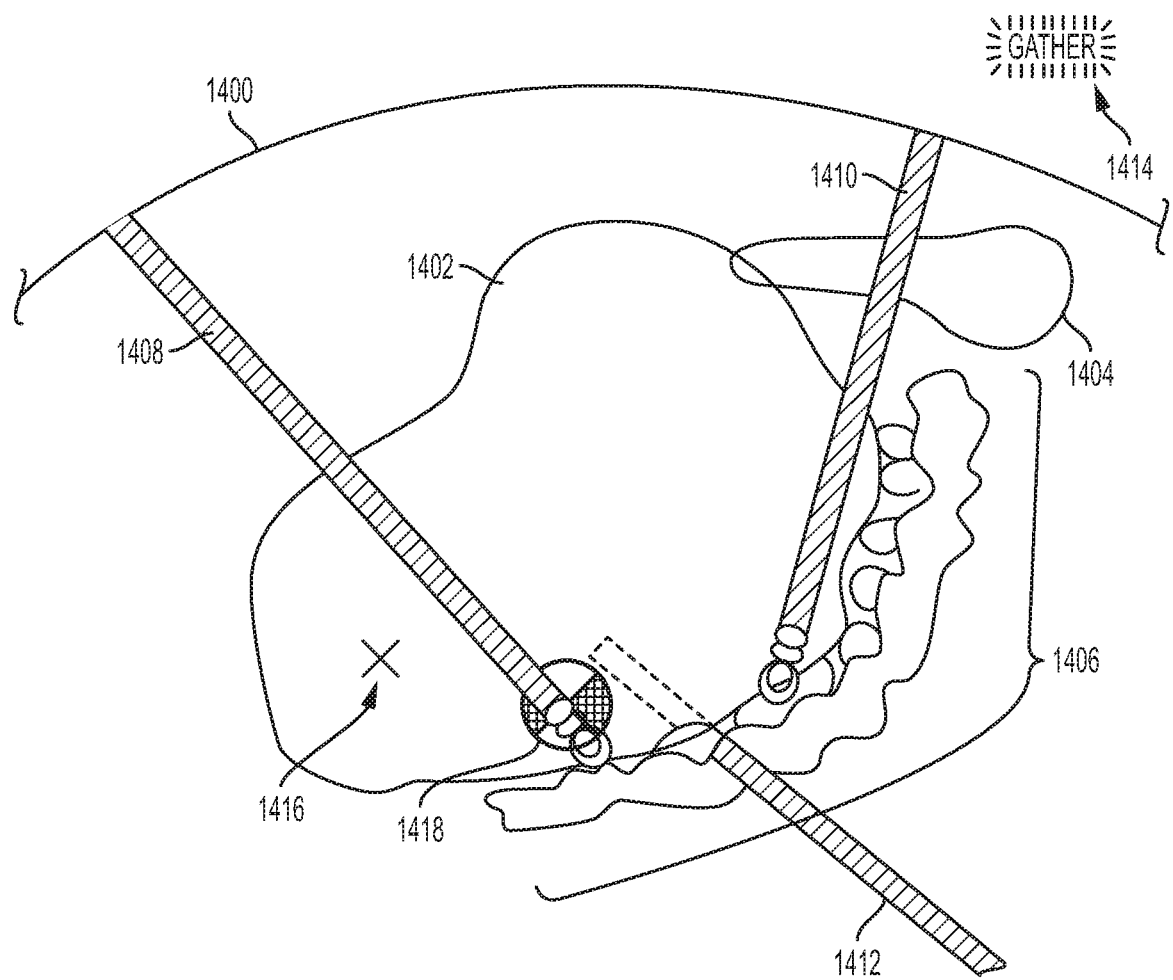
FIG. 25 is a schematic view of one embodiment of a display showing a visualized surgical space.

FIG. 25 illustrates one embodiment of a display that can be shown on a display screen of a robotic surgical system to facilitate movement of a surgical instrument between different anatomical quadrants. In this illustrated embodiment, a field of view 1400 of a camera (not shown) visualizing a patient has therein an omentum 1402 of the patient, a spleen 1404 of the patient, and an area 1406 including a small intestine, large intestine, vascular cascade, and arches of the patient. Three surgical instruments, a first grasper 1408, a second grasper 1410, and a suction/irrigation probe 1412, have been positioned relative to the patient and are also in the field of view 1400. The display includes a marker 1414 thereon indicating that the robotic surgical system is in a "gather" mode, e.g., is at a start of the gathering process 1300 of FIG. 23. The marker 1414 includes emphasized (glowing) text in this illustrated embodiment, but the marker 1414 can have any of a variety of configurations, e.g., different text, an icon, etc. The display in this illustrated embodiment also has a cursor 1416 and a first tool identifying marker 1418 thereon. The cursor 1416 is an "X" in this illustrated embodiment, but the cursor 1416 can have any of a variety of configurations, e.g., a dot, an hourglass, an arrow, etc. The first tool identifying marker 1418 in this illustrated embodiment is a CG (center of gravity) symbol, but the cursor 1416 can have any of a variety of configurations, e.g., a solid dot, a triangle in outline, an "S," an arrow, etc. The cursor 1416 and the first tool identifying marker 1418 can be used as discussed above regarding the gathering process 1302 of FIG. 23. In FIG. 25, the slave tool identifying marker 1418 has been positioned on the display at the one of the surgical instruments 1408, 1410, 1412 closest to the current position of the cursor 1416 to indicate a suggested one of the surgical instruments 1408, 1410, 1412 as a tool for movement.

Figure 26:
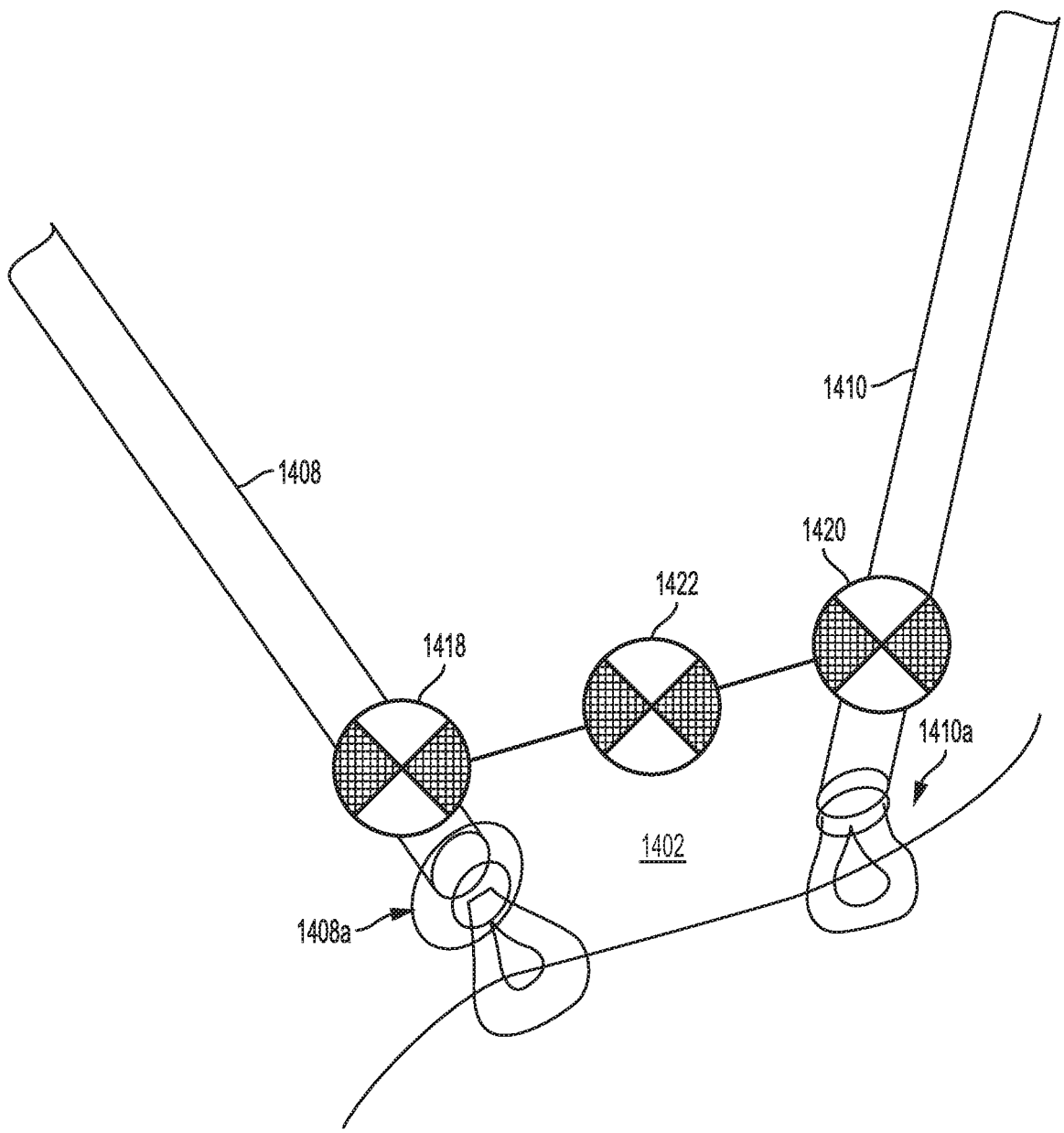
FIG. 26 is a schematic view of the display of FIG. 25 at a subsequent point in time.

FIG. 26 shows the display of FIG. 25 at a subsequent point in time and in a zoomed-in view. FIG. 16 also shows a wrist mechanism 1408a, 1410a of the first and second graspers 1408, 1410. In this illustrated embodiment, the first tool identifying marker 1418 remains on the first grasper 1408, thereby indicating that the first grasper 1408 has been selected by the user as a tool for movement, and a second tool identifying marker 1420 is on the second grasper 1410, thereby indicating that the user also selected the second grasper 1410 as a tool for movement. The second tool identifying marker 1420 is CG symbol in this illustrated embodiment, but as mentioned above, tool identifying markers can have other configurations. The display in this example also has thereon a central marker 1422 positioned on the display at a center point of the markers 1418, 1420 of all the selected tools 1408, 1410. For two selected instruments, the central marker 1422 can be at a midpoint between the two markers 1418, 1420. For three or more selected instruments, the central marker can be at a geometric centroid of the markers of selected instruments.

The central marker 1422 represents a reference point of movement for all the selected tools 1408, 1410 during movement of the selected tools 1408, 1410. The location of the markers 1418, 1420 on their respective tools 1408, 1410 thus has meaning for the upcoming coordinated movement of the selected tools 1408, 1410. The central marker 1422 may help the user visualize possible coordinated movement before the movement occurs. Because the robotic surgical system can know the location and orientation of each of the surgical instruments in use due to knowing the geometry of the movement mechanisms to which the surgical instruments are coupled, the robotic surgical system can map the selected ones of the surgical instruments 1408, 1410 to a common (shared) coordinate system. The central marker 1422 can be placed based on the common coordinate system.

In at least some embodiments, instead of using the calculated reference point represented on the display by the central marker 1422, the robotic surgical system can be configured to allow the user to select the reference point, such as by moving the cursor to a location on the display and clicking at that location.

Figure 27:
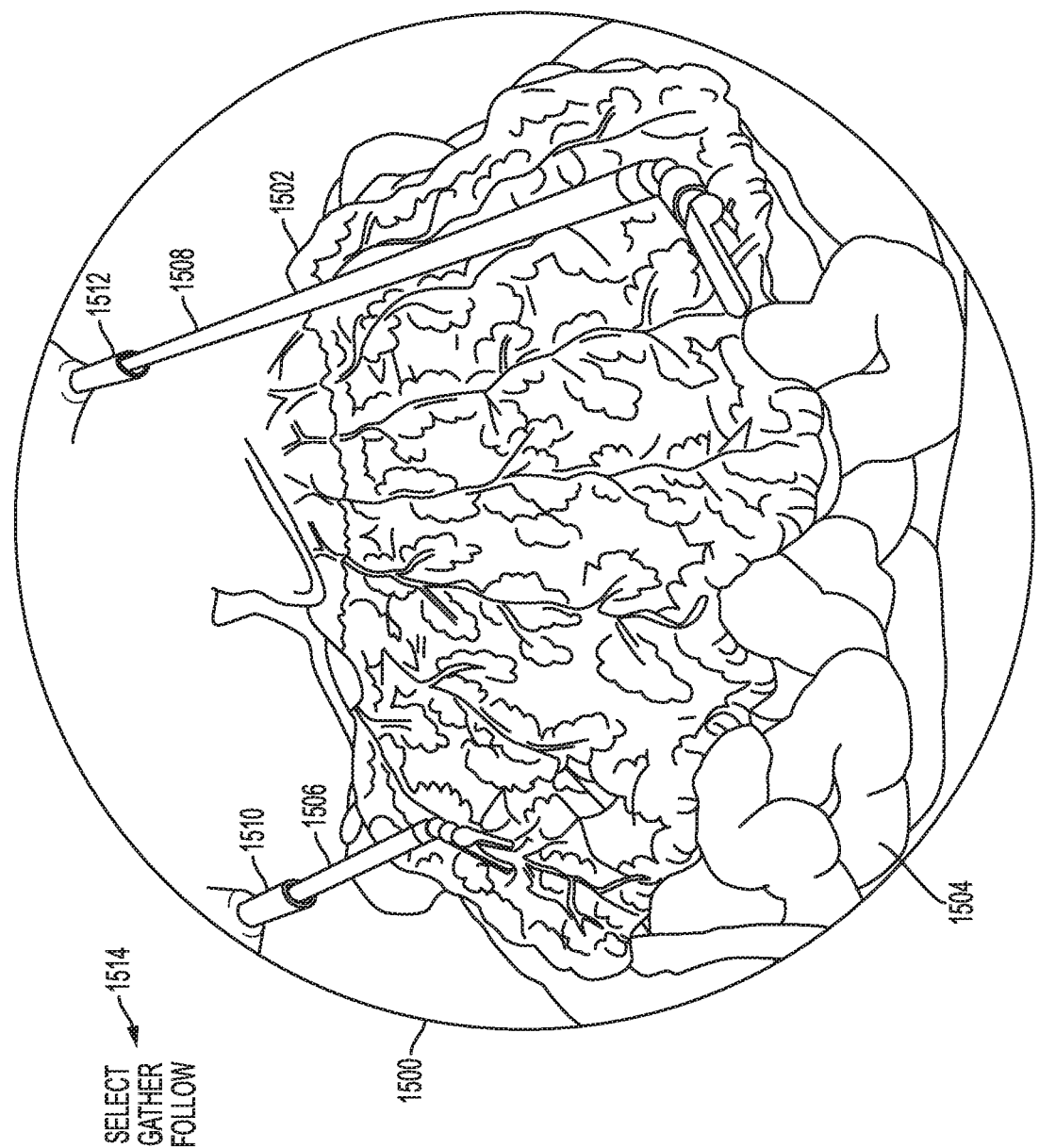
FIG. 27 is a schematic view of another embodiment of a display showing a visualized surgical space.

FIG. 27 illustrates another embodiment of a display that can be shown on a display screen of a robotic surgical system to facilitate movement of a surgical instrument between different anatomical quadrants. In this illustrated embodiment, a field of view 1500 of a camera (not shown) visualizing a patient has therein an omentum 1502 of the patient and an intestine 1504 of the patient. Two surgical instruments, a first grasper 1506 and a second grasper 1508, have been positioned relative to the patient and are also in the field of view 1500. First and second trocars 1510, 1512 through which the first and second graspers 1506, 1508 have respectively been advanced into the patient are also in the field of view 1500.

As in this illustrated embodiment, the display includes a legend 1514 thereon indicating select, gather, and follow modes in which the robotic surgical system can operate. The legend 1514 includes a list of text in this illustrated embodiment, but the legend 1514 can have other configurations, e.g., include other text, include icons, etc. The legend 1514 can appear at any location on the display. The select mode generally corresponds to a beginning portion of the gather process 1300 of FIG. 23, the gather mode generally corresponds to a remaining portion of the gather process 1300 of FIG. 23, and the follow mode generally corresponds to the follow process 1302 of FIG. 24. None of the select, gather, and follow modes are currently active, as indicated by the modes all being shown in shaded text. With the select, gather, and follow modes all being inactive, the display may be used by a user in any of a number of ways, such as for visualization of surgical space, for adjustment of the field of view 1500, etc.

Figure 28:
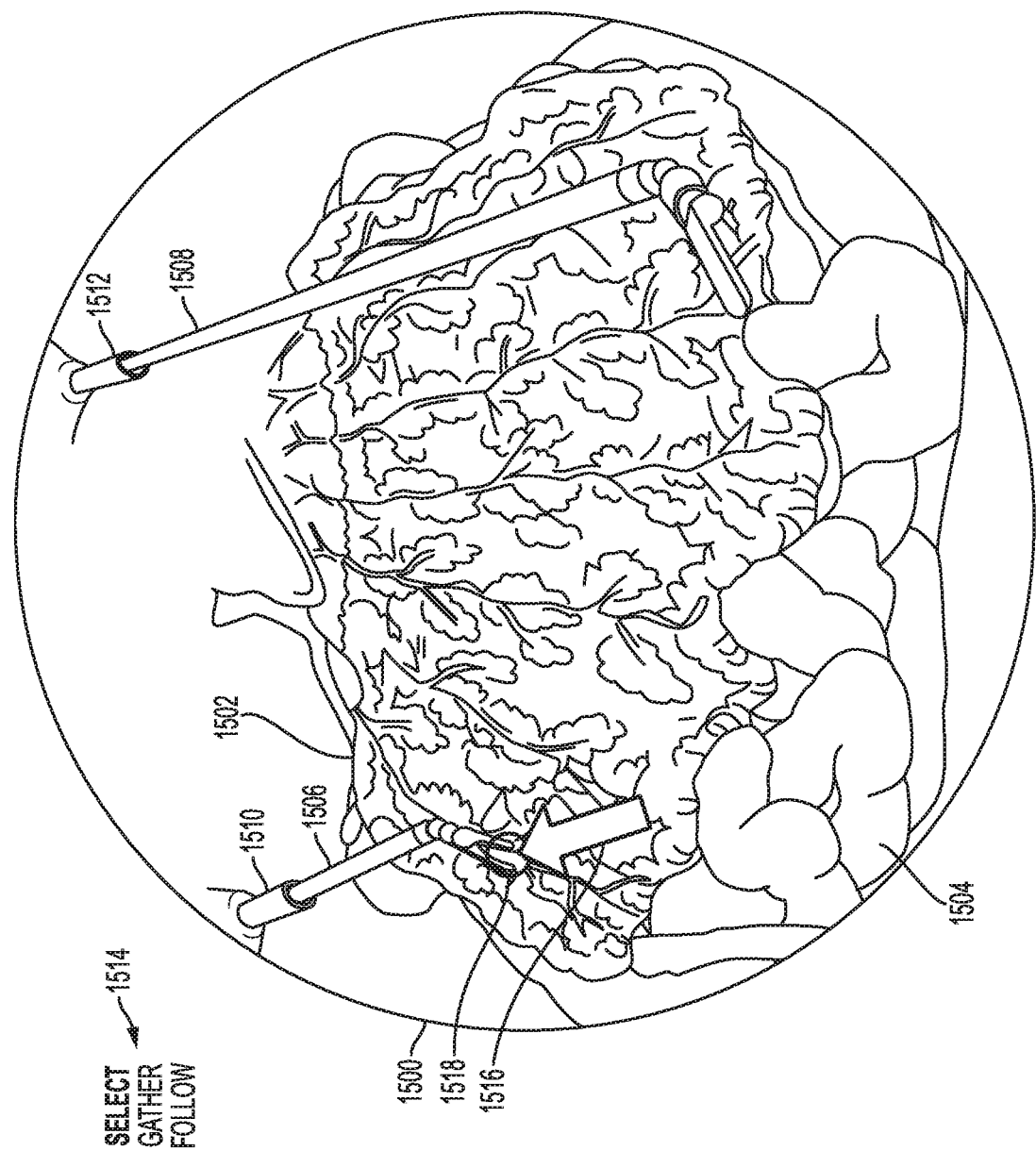
FIG. 28 is a schematic view of the display of FIG. 27 at a subsequent point in time.

FIG. 28 shows the display of FIG. 27 at a subsequent point in time. Select mode is now active, as indicated by the text "SELECT" being bolded in the legend 1514. Select mode generally reflects a mode for identifying of instruments to participate in a coordinated move. In at least some embodiments, only a selected one of the select, follow, and gather modes may appear in the legend 1514, e.g., the text "SELECT" may remain while the text "GATHER" and "FOLLOW" disappears. Select mode being activated generally corresponds to the indication 1304 of FIG. 23 and can be accomplished in any of a variety of ways, such as by the user positioning a cursor 1516 on the text "SELECT" and clicking thereon. FIG. 28 shows the cursor 1516 thereon and a suggested one of the instruments 1506, 1508 that is closest to the cursor 1516 marked with a first marker 1518. This suggestion generally corresponds to the suggesting 1308 of FIG. 23.

Figure 29:
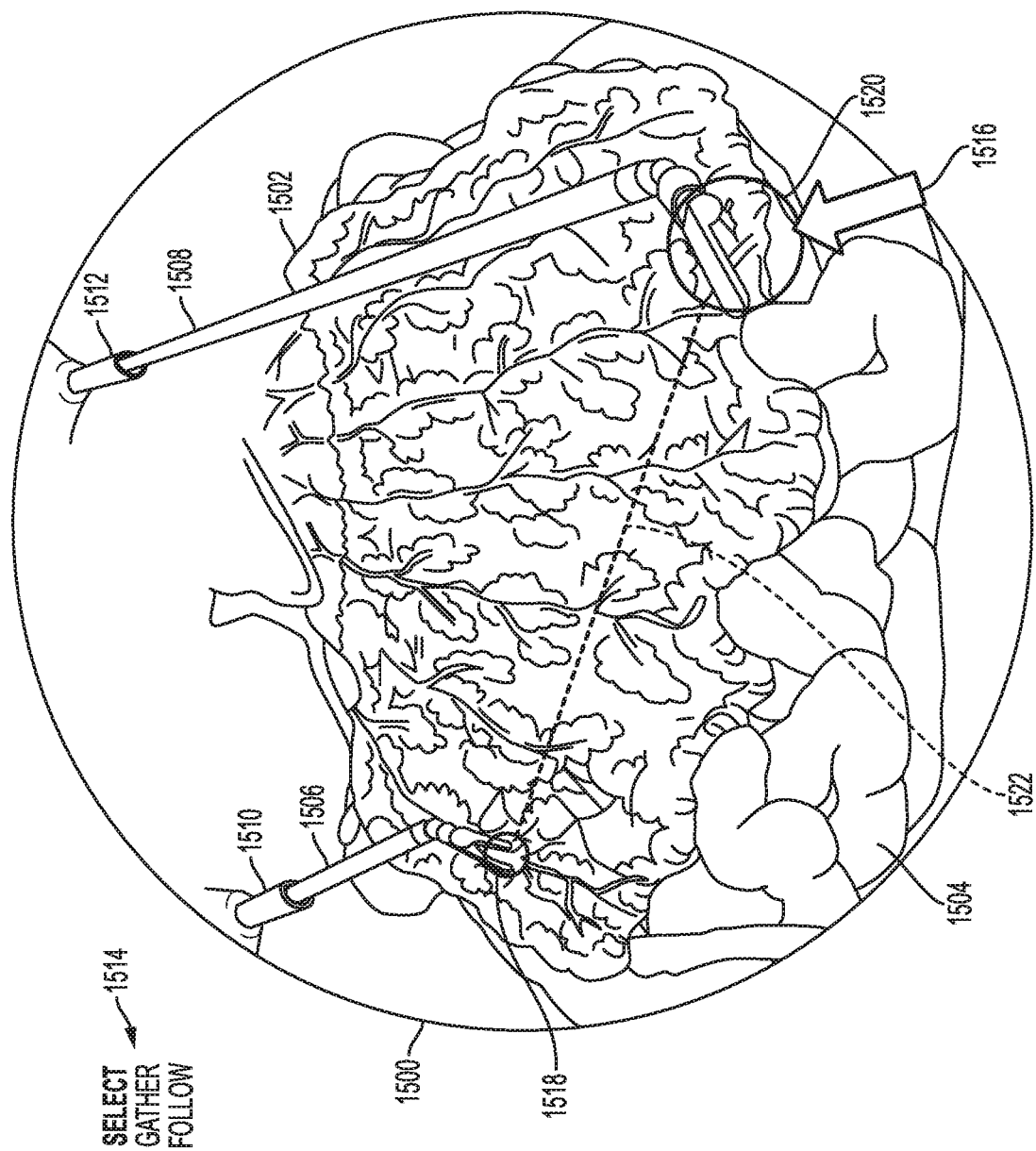
FIG. 29 is a schematic view of the display of FIG. 28 at a subsequent point in time.

FIG. 29 shows the display of FIG. 28 at a subsequent point in time. Select mode is still active, as indicated by the text "SELECT" still being bolded in the legend 1514. The first grasper 1506 has been selected as an instrument to move (e.g., indicated by the user similar to the indicating 1310 of FIG. 23), as indicated by the first marker 1518 still being displayed thereon. The user has moved the cursor 1516 to an unselected instrument, the second grasper 1508, which is suggested as an instrument to move by being marked with a second marker 1520. This suggestion generally corresponds to an iteration of the suggesting 1308 of FIG. 23. As in this illustrated embodiment, a connecting line 1522 can be shown on the display that connects the markers 1518, 1520. The connecting line 1522 may provide the user with a visual frame of reference. The connecting line 1522 is dashed on the display because the second grasper 1508 has not yet been indicated by the user as being a tool to move.

Figure 30:
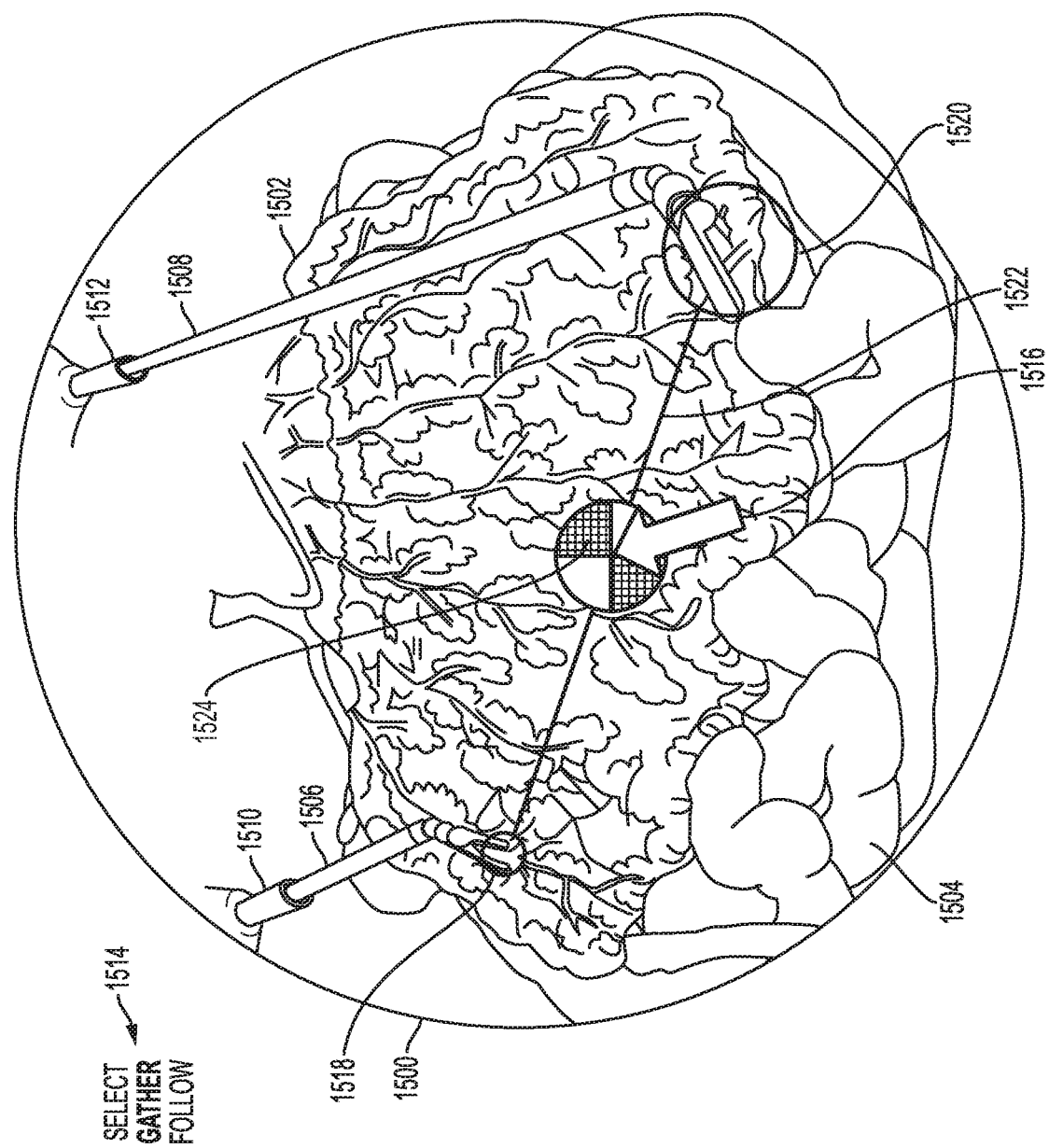
FIG. 30 is a schematic view of the display of FIG. 29 at a subsequent point in time.

FIG. 30 shows the display of FIG. 29 at a subsequent point in time. Gather mode is now active, as indicated by the text "GATHER" being bolded in the legend 1514. Gather mode generally reflects a mode for the user to identify what subsequent motion commands (e.g. by moving a user input device) should mean to the selected instruments. This identifying can include identifying one of the instruments as a master, with the others being slaves to follow the master according to some prescribed behavior such as "maintain the spatial relationship you now have," "maintain the relationship you have as seen in the present image," etc. The identifying can include identifying the centroid of the selected instruments as the master, or the center of the field of view. The user can choose the gather mode in any of a variety of ways, such as by positioning the cursor 1516 on the text "GATHER" and clicking thereon. In at least some embodiments, the robotic surgical system can automatically move from the select mode to the gather mode in response to the user indicating that no more tools are to be selected for movement, similar to the indicating 1316 of FIG. 23. The display in the gather mode has thereon a central marker 1524 positioned on the display at a center point of the markers 1518, 1520 of all the selected tools 1506, 1508, similar to the central marker 1422 of FIG. 26. The connecting line 1522 is solid on the display because the second grasper 1508 has been indicated by the user as being a tool to move such that there have been at least two instruments selected so that a central point can be calculated by the robotic surgical system (e.g., by the controller thereof). The cursor 1516 can be moved by the user indicating that the central marker 1524 is the element that will be controlled in the subsequent follow mode.

Figure 31:
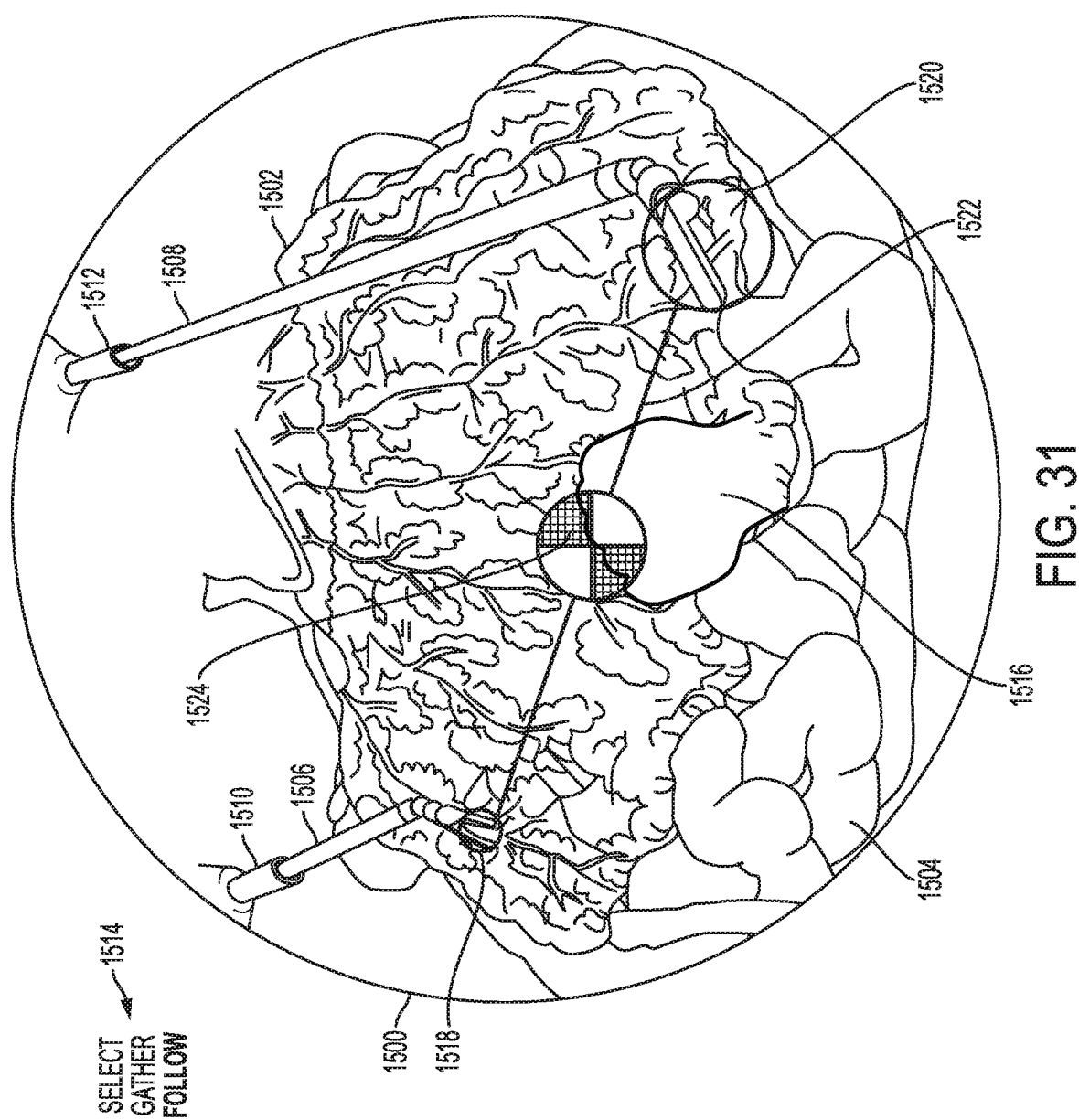
FIG. 31 is a schematic view of the display of FIG. 30 at a subsequent point in time.

FIG. 31 shows the display of FIG. 30 at a subsequent point in time. Follow mode is now active, as indicated by the text "FOLLOW" being bolded in the legend 1514. The user can choose the follow mode in any of a variety of ways, such as by positioning the cursor 1516 on the text "FOLLOW" and clicking thereon. In at least some embodiments, the robotic surgical system can automatically move from the gather mode to the follow mode in response to the user indicating that no more tools are to be selected for movement, similar to the choosing 1320 of FIG. 23. The cursor 1516 has a different appearance in the gather mode than its appearance in the select and follow modes, which may help signal to the user that the selected instruments 1506, 1508 are ready to be moved. The cursor's form may remind the user that both translational and rotational movements of the selected instruments will be made in response to user commands. Such movements may be advantageous in moving an organ to avoid its distortion or excess tension on its attachments. The central marker 1524 can serve as a tether that the user can manipulate to move the selected tools 1506, 1508, as indicated by the cursor 1516 being positioned at the central marker 1524. The selected tools 1506, 1508 in FIG. 31 have not yet been moved from their position in FIGS. 27-30.

Figure 32:
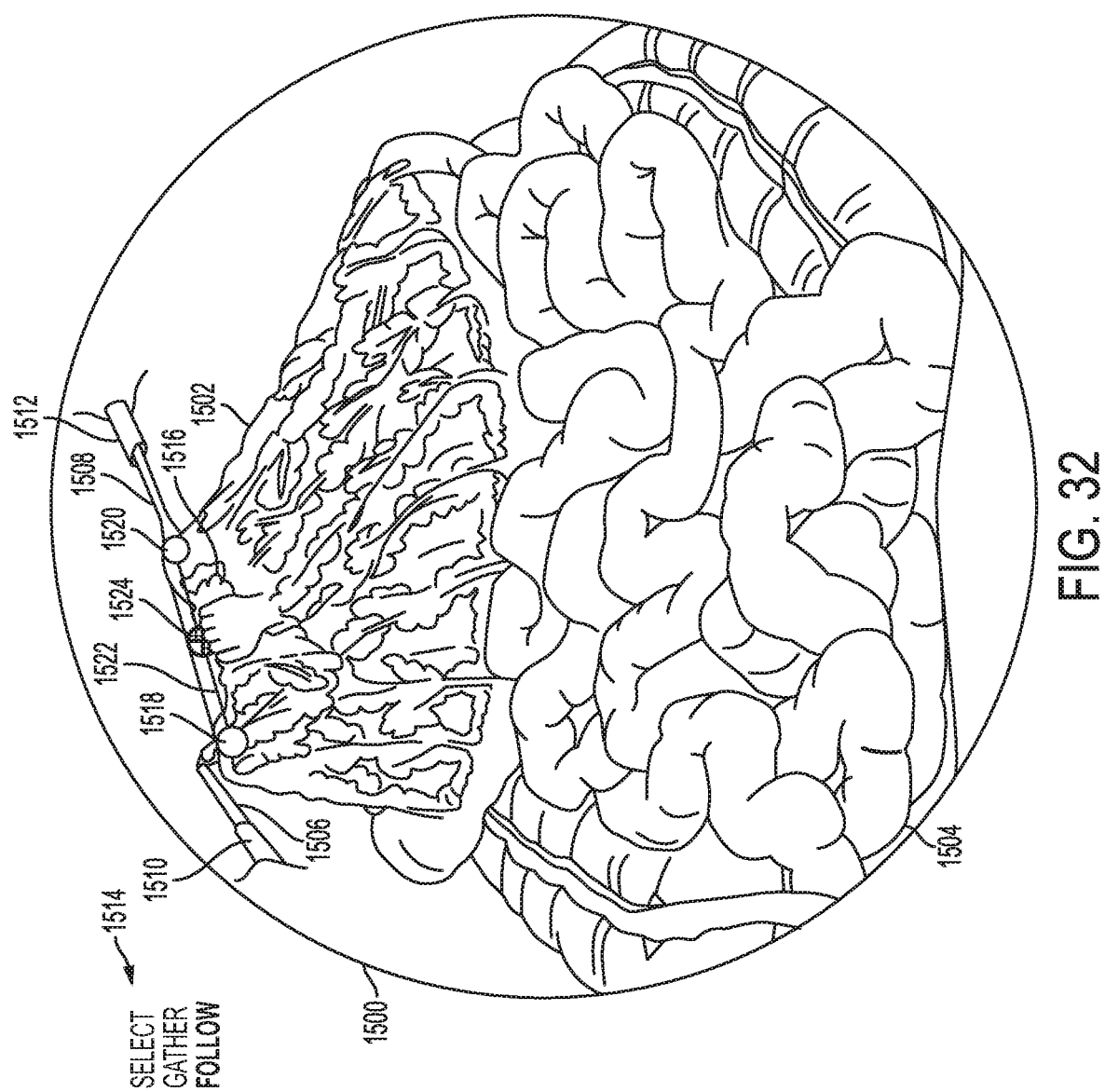
FIG. 32 is a schematic view of the display of FIG. 31 at a subsequent point in time.

FIG. 32 shows the display of FIG. 32 at a subsequent point in time. Follow mode is still active, as indicated by the text "FOLLOW" still being bolded in the legend 1514. The user has provided input to the system (e.g., via a user input device similar to the providing 1324 of FIG. 24), and the system in response to the input has moved the first and second graspers 1506, 1508 in coordination with each other, similar to the causing 1326 of FIG. 24. The first and second markers 1518, 1520 have traveled with their respective first and second graspers 1506, 1508, as has the connecting line 1522 and the central marker 1524. The traveling of the cursor 1516, as moved by the user, may help the user provide input to the system (e.g., via the user device) that moves the selected instruments 1506, 1508 in a way desired by the user since all graphical overlays (markers, lines, text, etc.) should still be congruent with the instruments if the robot surgical system has moved correctly without collisions or faults occurring. The movement of the first and second graspers 1506, 1508 is shown in real time on the display in this illustrated embodiment, and the first, second, and central markers 1518, 1520, 1524, the connecting line 1522, and the cursor 1516 can move on the display in real time with the movement of the selected instruments 1506, 1508, which may help the user move the selected instruments 1506, 1508 in a desired way and make any needed movement corrections in real time with the selected instruments' movement. After all movement of the selected instruments 1506, 1508 desired by the user has been accomplished, the user can deactivate the follow mode, such as by clicking on either the "GATHER" text or the "SELECT" text in the legend 1514. The deactivation can be similar to the ending 1330 of FIG. 24.

One example of movement using the reference point defined by the central marker 1524, whether its location is calculated by the system or selected by the user, is the user requesting rotation about a z axis, e.g., abduction. In response, the connecting line 1522 can rotate about a vertical axis extending through the central marker 1524 such that one of the instruments 1506, 1508 extends and the other of the instruments 1506, 1508 retracts while maintaining a same distance between the instruments 1506, 1508. The selected instruments can move in response to cursor 1516 movements, not the tool markers or connecting line 1522 in response to center marker 1524. The cursor 1516 that has moved has breadth, depth, and volume, so that rotating the cursor 1516 has visual significance to the user since it is virtually connected to the appropriate user input device. In contrast, rotating a point on a line is not visually apparent. In at least some embodiments, graphical objects on the display can be eliminated, once the select and gather phases are complete since they may no longer be needed. For another example of movement using the reference point defined by the central marker 1524, whether its location is calculated by the system or selected by the user, is the user requesting rotation about a y axis, e.g., supination. In response, the tool markers 1518, 1520 would move in a same direction along a circumference circle whose diameter is the connecting line 1522. For yet another example of movement using the reference point defined by the central marker 1524, whether its location is calculated by the system or selected by the user, is a camera tracking the central marker 1524 during movement of the selected instrument(s).

Figure 33:
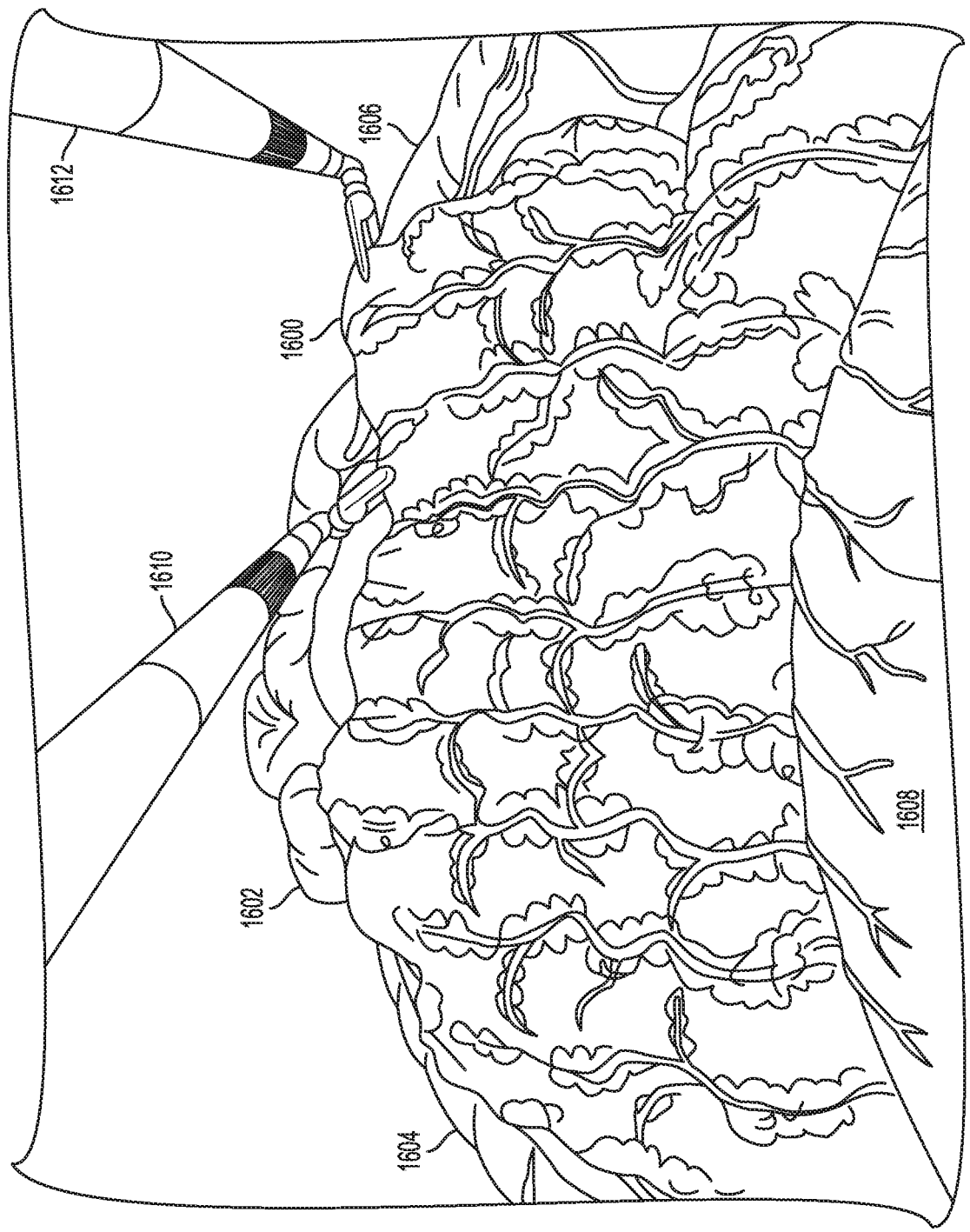
FIG. 33 is a schematic view of another embodiment of a display showing a visualized surgical space.

FIG. 33 illustrates yet another embodiment of a display that can be shown on a display screen of a robotic surgical system to facilitate movement of a surgical instrument between different anatomical quadrants. In this illustrated embodiment, a field of view of a camera (not shown) visualizing a patient has therein an omentum 1600 of the patient, a small intestine 1602 of the patient, a descending colon 1604 of the patient, an ascending colon 1606 of the patient, and a stomach 1608 of the patient. Two surgical instruments, a first grasper 1610 and a second grasper 1612, have been positioned relative to the patient and are also in the field of view.

Figure 34:
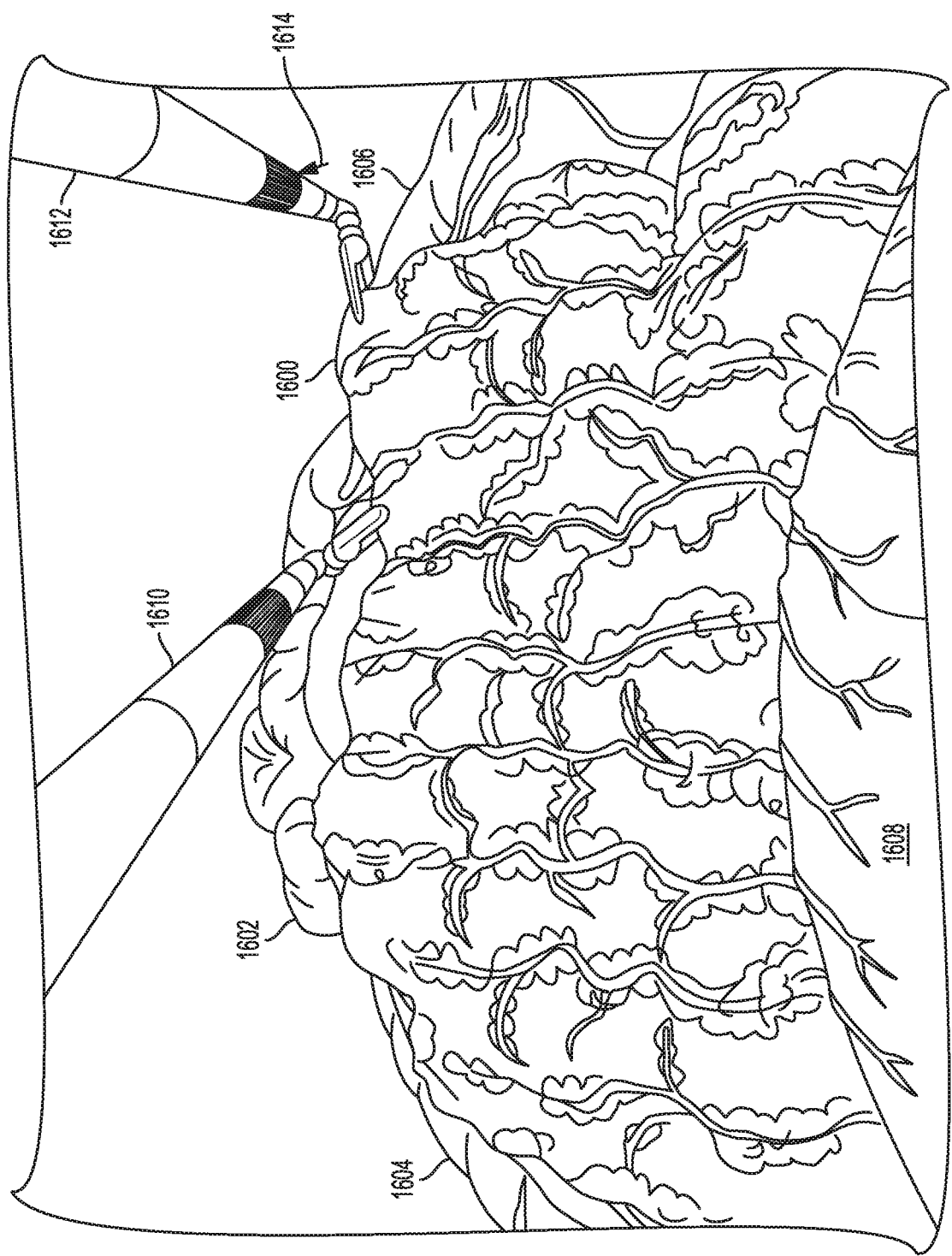
FIG. 34 is a schematic view of the display of FIG. 33 at a subsequent point in time.
Figure 35:
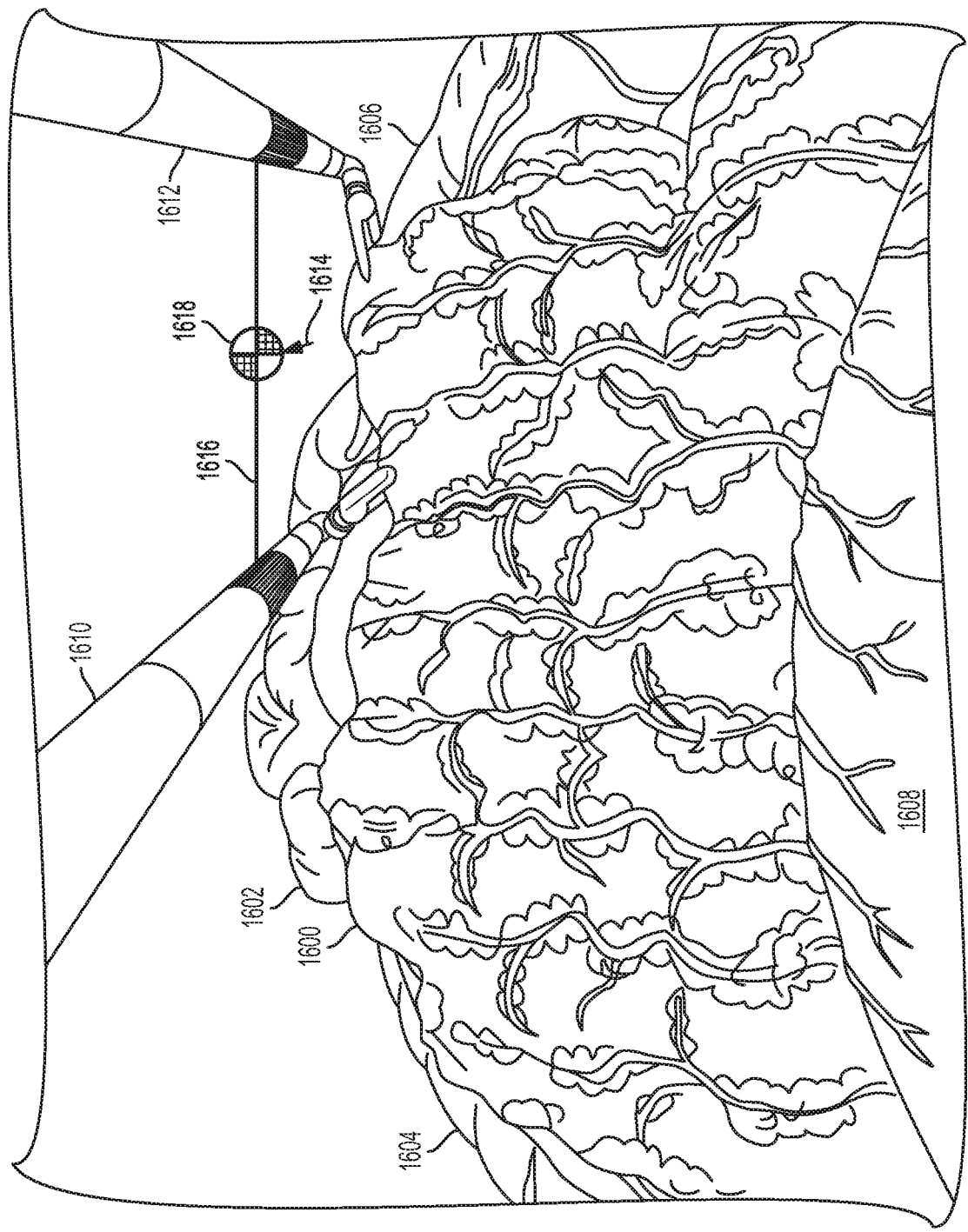
FIG. 35 is a schematic view of the display of FIG. 34 at a subsequent point in time.
Figure 36:
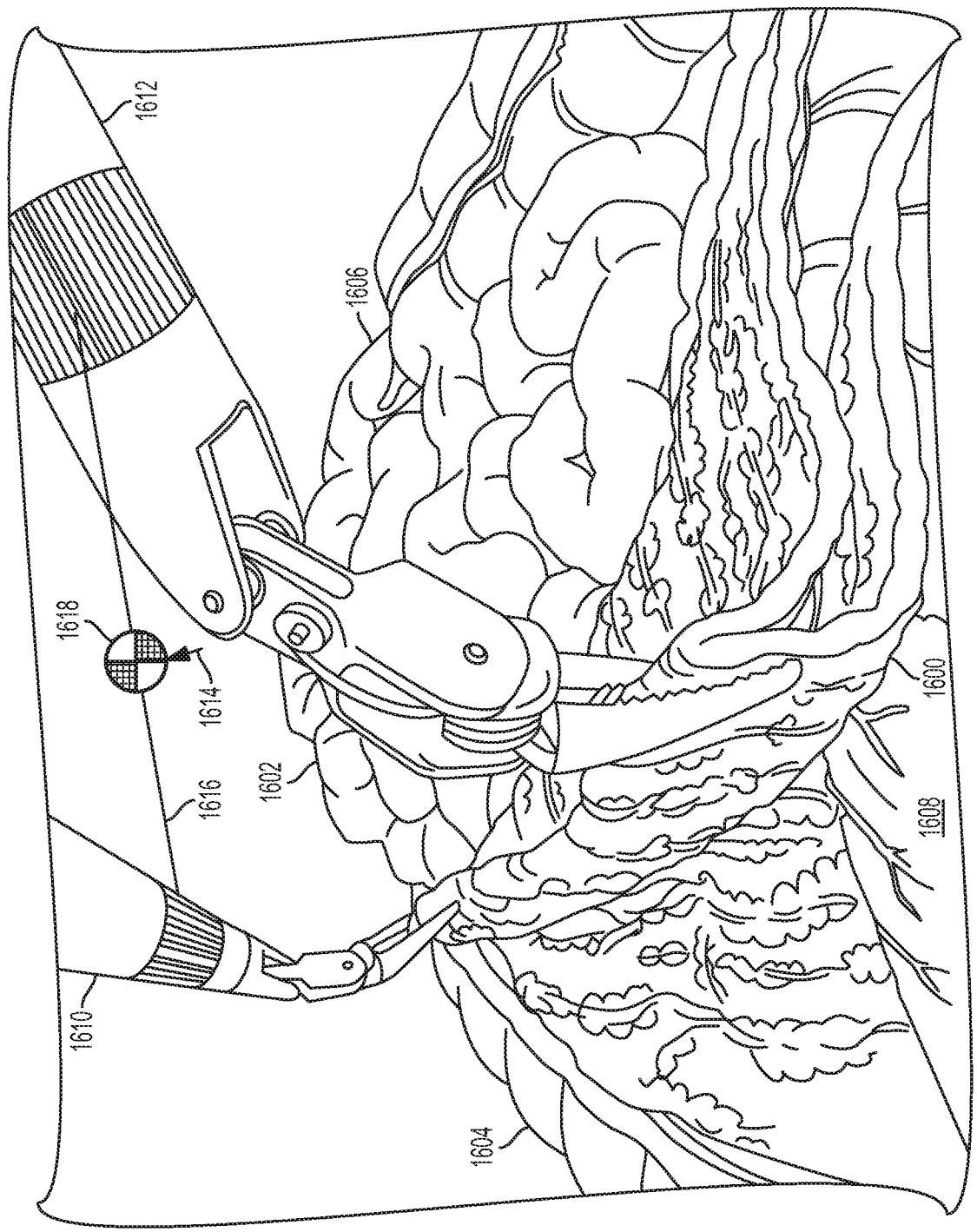
FIG. 36 is a schematic view of the display of FIG. 35 at a subsequent point in time.

FIG. 34 shows the display of FIG. 33 at a subsequent point in time. FIG. 34 shows a cursor 1614 on the display that the user has moved to the second grasper 1612. The cursor 1614 can, as mentioned herein, have other configurations, such as like the hand cursor 1516 of FIG. 31 that can depict to the user what user input device hand motions will achieve. FIG. 35 shows the display of FIG. 34 at a subsequent point in time. The user has selected the first and second graspers 1610, 1612 as instruments to move, as indicated by a solid connecting line 1616 extending therebetween and a central marker 1618 being on the line 1616. The selected instruments 1610, 1612 do not have markers thereon indicating that they have been selected, which may help reduce clutter on the display. The selected tools 1610, 1612 in FIG. 35 have not yet been moved from their position in FIGS. 33 and 34. FIG. 36 shows the display of FIG. 35 at a subsequent point in time. The user has provided input to the system (e.g., via a user input device similar to the providing 1324 of FIG. 24), and the system in response to the input has moved the first and second graspers 1610, 1612 in coordination with each other, similar to the causing 1326 of FIG. 24.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
   displaying on a display device an image of a surgical area visualized by a camera, the camera having a field of view defining a perimeter of the visualized surgical area;
   a robotic surgical system calculating a bearing error based on a current angular offset of a longitudinal axis of a surgical instrument from a reference point in the field of view, the surgical instrument being located outside the perimeter of the visualized surgical area, and the surgical instrument being coupled to an electromechanical arm of the robotic surgical system;
   the robotic surgical system causing a signal to be provided to a user of the robotic surgical system, the signal being indicative of the bearing error;
   with the surgical instrument still being outside the perimeter of the visualized surgical area, the robotic surgical system calculating a second bearing error based on a current angular offset of the longitudinal axis of the surgical instrument from the reference point in the field of view; and
   the robotic surgical system causing the signal to change in real time with movement of the electromechanical arm and the surgical instrument coupled thereto relative to the visualized surgical area based on the second bearing error.

2. The method of claim 1, further comprising the robotic surgical system causing the signal to stop in response to the surgical instrument moving to a location inside the perimeter of the visualized surgical area.

3. The method of claim 1, wherein the signal includes at least one of an audible sound, a visual signal shown on the display device, a visual signal shown on a second display device, a tactile signal palpable by a user of the robotic surgical system, and an illuminated light.

4. The method of claim 3, wherein the signal includes at least the audible sound, and changing the signal includes changing a pitch of the sound or changing an amplitude of the sound.

5. The method of claim 3, wherein the signal includes at least one of the visual signal shown on the display device and the visual signal shown on the second display device, and changing the signal includes changing an appearance of the at least one of the visual signal shown on the display device and the visual signal shown on the second display device.

6. The method of claim 3, wherein the signal includes at least the illuminated light, and changing the signal includes changing the light in at least one of brightness and color.

7. The method of claim 1, wherein a controller of the robotic surgical system calculates the bearing error, causes the signal to be provided, calculates the second bearing error, and causes the signal to change in real time with the movement of the electromechanical arm and the surgical instrument.

8. The method of claim 1, wherein the reference point in the field of view is a centerpoint of the field of view.

9. The method of claim 1, wherein the reference point in the field of view dynamically changes based on a location of a second surgical instrument present within the field of view.

10. The method of claim 1, wherein the reference point in the field of view is a centerpoint of a line joining a pair of surgical instrument working ends present within the field of view.

11. The method of claim 1, wherein the reference point in the field of view is a point along a trajectory of the surgical instrument that is defined by the longitudinal axis and that is nearest to a working end of any surgical instrument present within the field of view.

12. The method of claim 1, wherein the reference point in the field of view is a point of first intersection of the longitudinal axis with a surface within the field of view.

13. A surgical method, comprising:
   displaying on a display device an image of a surgical area visualized by a camera, the camera having a field of view defining a perimeter of the visualized surgical area;
   a robotic surgical system calculating a bearing error based on a current angular offset of a longitudinal axis of a trocar from a reference point in the field of view, a surgical instrument being positioned within the trocar, being located outside the perimeter of the visualized surgical area, and being coupled to an electromechanical arm of the robotic surgical system;

the robotic surgical system causing a signal to be provided to a user of the robotic surgical system, the signal being indicative of the bearing error;

with the surgical instrument still being outside the perimeter of the visualized surgical area, the robotic surgical system calculating a second bearing error based on a current angular offset of the longitudinal axis of the trocar from the reference point in the field of view; and the robotic surgical system causing the signal to change in real time with movement of the electromechanical arm and the surgical instrument coupled thereto relative to the visualized surgical area based on the second bearing error.

14. The method of claim 13, further comprising stopping the signal in response to the surgical instrument moving to a location inside the perimeter of the visualized surgical area.

15. The method of claim 13, wherein the signal includes at least one of an audible sound, a visual signal shown on the display device, a visual signal shown on a second display device, a tactile signal palpable by a user of the robotic surgical system, and an illuminated light.

16. The method of claim 13, wherein a controller of the robotic surgical system calculates the bearing error, causes the signal to be provided, calculates the second bearing error, and causes the signal to change in real time with the movement of the electromechanical arm and the surgical instrument.

17. The method of claim 13, wherein the reference point in the field of view is a centerpoint of the field of view.

18. The method of claim 13, wherein the reference point in the field of view dynamically changes based on a location of a second surgical instrument present within the field of view.

19. The method of claim 13, wherein the reference point in the field of view is a centerpoint of a line joining a pair of surgical instrument working ends present within the field of view.

20. The method of claim 13, wherein the reference point in the field of view is a point along a trajectory of the trocar that is defined by the longitudinal axis and that is nearest to a working end of any surgical instrument present within the field of view.

21. The method of claim 13, wherein the reference point in the field of view is a point of first intersection of the longitudinal axis with a surface within the field of view.

* * * * *